(12) United States Patent
Chen et al.

(10) Patent No.: US 9,040,718 B2
(45) Date of Patent: May 26, 2015

(54) HYBRID HOST MATERIALS FOR ELECTROPHOSPHORESCENT DEVICES

(75) Inventors: Shaw H. Chen, Rochester, NY (US); Lichang Zeng, Rochester, NY (US); Thomas Yung-Hsin Lee, Rochester, NY (US)

(73) Assignee: The University of Rochester, Rochester, NY (US)

( * ) Notice: Subject to any disclaimer, the term of this patent is extended or adjusted under 35 U.S.C. 154(b) by 657 days.

(21) Appl. No.: 12/692,462

(22) Filed: Jan. 22, 2010

(65) Prior Publication Data

US 2010/0184942 A1 Jul. 22, 2010

Related U.S. Application Data

(60) Provisional application No. 61/146,523, filed on Jan. 22, 2009, provisional application No. 61/253,259, filed on Oct. 20, 2009.

(51) Int. Cl.

| C08G 73/06 | (2006.01) |
|---|---|
| C07D 209/82 | (2006.01) |
| C07D 251/12 | (2006.01) |
| C07D 307/91 | (2006.01) |
| C07D 405/10 | (2006.01) |
| C07F 5/02 | (2006.01) |
| C07F 7/08 | (2006.01) |
| C07F 9/53 | (2006.01) |
| C08G 61/12 | (2006.01) |
| C08G 73/08 | (2006.01) |

(Continued)

(52) U.S. Cl.

CPC ............ *C07D 209/82* (2013.01); *C07D 251/12* (2013.01); *C07D 307/91* (2013.01); *C07D 405/10* (2013.01); *C07F 7/0818* (2013.01); *C07F 9/5325* (2013.01); *C08G 61/12* (2013.01); *C08G 61/122* (2013.01); *C08G 61/123* (2013.01); *C08G 61/124* (2013.01); *C08G 61/126* (2013.01); *C08G 73/0644* (2013.01); *C08G 73/0672* (2013.01); *C08G 73/08* (2013.01); *C08L 79/04* (2013.01); *C08L 79/06* (2013.01); *C08G 2261/3142* (2013.01); *C08G 2261/3221* (2013.01); *C08G 2261/3241* (2013.01); *C08G 2261/52* (2013.01); *C08G 2261/3424* (2013.01); *Y10S 428/917* (2013.01)

(58) Field of Classification Search

USPC .................... 252/301.35; 548/444; 544/180
See application file for complete search history.

(56) References Cited

U.S. PATENT DOCUMENTS

| 6,863,997 B2 | 3/2005 | Thompson et al. |
| 2005/0069729 A1* | 3/2005 | Ueda et al. .................. 428/690 |

(Continued)

OTHER PUBLICATIONS

Sudhakar et al (Phosphorescence Quenching by Conjugated Polymers, J. Am. Chem. Soc. 2003, 125, 7796-7797).*

(Continued)

*Primary Examiner* — Rachel Kahn
(74) *Attorney, Agent, or Firm* — Hodgson Russ LLP

(57) ABSTRACT

Compounds (including polymers) for use in hybrid host materials which can be used in electroluminescent devices. The compounds comprise at least one electron-transporting moiety and at least one hole-transporting moiety which are joined by a flexible linker. Hybrid host materials comprising the compounds exhibit stability against phase separation, elevated glass transition temperature, morphological stability against crystallization, and isolation of the electron transporting moiety and hole transporting moiety π-systems.

2 Claims, 22 Drawing Sheets

(51) Int. Cl.
*C08L 79/04* (2006.01)
*C08L 79/06* (2006.01)

(56) References Cited

U.S. PATENT DOCUMENTS

2006/0079647 A1    4/2006  Bazan et al.
2006/0093933 A1    5/2006  Michaleviciute et al.
2007/0111027 A1*   5/2007  Chen et al. .................. 428/690
2008/0026135 A1    1/2008  Bentsen et al.
2008/0211391 A1    9/2008  Burn et al.

OTHER PUBLICATIONS

Si et al (Synthesis, Structural Characterization, and Electrophosphorescent Properties of Rhenium(I) Complexes Containing Carrier-Transporting Groups, Inorg. Chem. 2007, 46, 6155-6163).*

* cited by examiner

HYBRID HOST MATERIALS FOR ELECTROPHOSPHORESCENT DEVICES

CROSS-REFERENCE TO RELATED APPLICATIONS

This application claims priority to U.S. provisional application No. 61/146,523, filed on Jan. 22, 2009, and U.S. provisional application No. 61/253,259, filed on Oct. 20, 2009, the disclosures of which are incorporated herein by reference.

FIELD OF THE INVENTION

The present invention relates to the preparation and use of hybrid compounds with bipolar charge-transport properties for use as host materials for electrophosphorescent organic light-emitting diodes.

BACKGROUND OF THE INVENTION

Since the invention of relatively efficient fluorescent organic light-emitting diodes (OLEDs), a new generation of flat-panel displays has emerged with a potential for capturing a substantial market share of consumable electronics, such as television sets and computer monitors. While full-color OLED displays require the emission of blue, green and red light, white OLEDs are potentially useful as efficient and inexpensive solid-state lighting and as backlights for liquid crystal displays. Compared to molecular materials that can be vacuum-deposited into thin films, solution processible materials, such as π-conjugated polymers and monodisperse π-conjugated oligomers, offer cost advantage and ease of scale-up to large-area thin films.

Fluorescence or phosphorescence is responsible for light emission from organic luminophores. Electrophosphorescence is superior to electrofluorescence in terms of internal quantum yield, 100 versus 25%. Despite the intensive efforts worldwide over the past decade, device efficiency and lifetime have remained major challenges to both types of OLED. For the fabrication of an efficient phosphorescent OLED, a triplet emitter (a guest) is typically doped in a host material with a higher triplet energy, $E_T$, to realize blue, green or red emission. To substantially improve device efficiency and lifetime, it is imperative that the electron and hole fluxes through fluorescent and phosphorescent OLED devices be balanced and to prevent the accumulation of charges and excitons at interfaces.

Normally, triplet host materials are capable of preferentially transporting holes or electrons. An electron- and/or a hole-transport layer is added to facilitate the injection and transport of deficient charge carriers into the emitter layer for efficient light emission. Nevertheless, with a unipolar host, charge recombination tends to occur close to the interface with the charge-transport layer for lack of bipolar-transport capability of emitter layer. Under the high current density associated with practical applications, confinement of excitons to the interfacial region could lead to fast triplet-triplet annihilation, resulting in efficiency roll-off. Furthermore, a narrow recombination zone is detrimental to operational stability because only a fraction of molecules contribute to charge transport, exciton formation, and light emission. Mixed hosts consisting of electron- and hole-transport molecules have been attempted to alleviate this problem. It has been demonstrated that mixed hosts can effectively decrease driving voltage while improving device efficiency sustainable at high current densities. A typical phosphorescent layer is comprised of a host mixed with a charge-transport component at 25 to 50 wt %, into which 1 to 10 wt % of triplet emitter is doped. The desired bipolar-transport capability requires a high concentration of the charge-transport additive, which may result in phase separation that can adversely affect long-term operational stability of OLEDs.

In general, the host materials should have a minimum $E_T$ level of 2.7, 2.5, and 2.0 eV to accommodate a blue-, green- and red-emitting guest, respectively. The HOMO/LUMO (highest occupied molecular orbital/lowest occupied molecular orbital) energy levels and charge-transport properties can be tuned by physically blending triplet hosts with appropriate materials at a risk of phase separation. Methods also exist for tuning $E_T$ by chemical modification assisted by computational chemistry. In principle, the host's $E_T$ level must be higher than the guest's to ensure host-to-guest energy transfer without the undesirable backward transfer, but close proximity of the two $E_T$ values is favorable to energy transfer because of the strong spectral overlap. The HOMO/LUMO levels can also be adjusted through chemical modification to facilitate the injection of holes and electrons.

A bipolar compound can be constructed by chemically bonding an electron- and a hole-transport moiety resulting in conjugated bipolar compounds. Conjugated bipolar compounds tend to be rigid and bulky, thus limiting solubility and the ability to form morphologically stable glassy films, which are essential to the fabrication of organic electronic devices for information display and solid-state lighting. Furthermore, as a result of the conjugation of the electron- and a hole-transport moieties, the $E_T$ of these moieties (triplet energy) are consistently diminished and LUMO/HOMO levels of these moieties are substantially modified in comparison to those of the two independent moieties, thus limiting the practical utility of conjugated hybrids.

Thus, based on the foregoing there exists an ongoing and unmet need for host materials with improved properties.

BRIEF SUMMARY OF THE INVENTION

The present invention provides compounds (which includes polymers), and compositions comprising the compounds, which can be used as host materials in electroluminescent devices.

The non-conjugated bipolar hybrids of the present invention have flexible linkages between ETMs and HTMs. The flexible linkages serve to increase entropy with enriched conformations, which is conducive to solubility in benign solvents for facile materials purification and solution processing. The increased entropy also presents a higher free energy barrier to crystallization from glassy state, thereby improving morphological stability against crystallization over relatively rigid conjugated and non-conjugated bipolar hybrids in prior arts. In the absence of π-conjugation, the triplet energies of the bipolar hybrids embodied herein are imported from those of ETMs and HTMs without constraint by the hybrids' electrochemical energy gaps.

In one embodiment, the compounds have the following general structures:

or

The compounds comprise at least one electron-transporting moiety (ETM) (A) and at least one hole-transporting moiety (HTM) (B) connected by a linker moiety (L). The number of possible HTMs (x) per E™, or the number of possible ETMs (y) per HTM is dependant on the structure of the ETM and HTM in the hybrid molecule, typically ranging from 1 to 10. Both the ETMs and HTMs are semiconducting with an electron and a hole mobility, respectively, in the range from $10^{-7}$ to $10^{-2}$ cm$^2$/V·s.

The compounds of the present invention involve chemically bonding electron-transporting and hole-transporting moieties via a linker resulting in interruption of π-conjugation of the individual moieties to produce compounds which are useful as hybrid materials. The use of a linker to bind the ETM and the HTM moieties allows both the moieties to retain their individual HOMO/LUMO levels and $E_T$ in the hybrid material and imparts bipolar-transport capability to the hybrid materials. For example, injection of electrons and holes are determined primarily by the LUMO and HOMO levels, respectively. The hybrid molecule's energy levels receptive to charge injection are furnished by its ETM and HTM moieties. Further, charge-transport properties are determined by these two energy levels as well as the overlap of molecular orbitals and reorganization energy, both affected by film morphology.

In another embodiment, the compounds of the present invention are bipolar polymers and compositions comprising the bipolar polymers, which can be used as host materials in electroluminescent devices. The bipolar polymers have the following general structures:

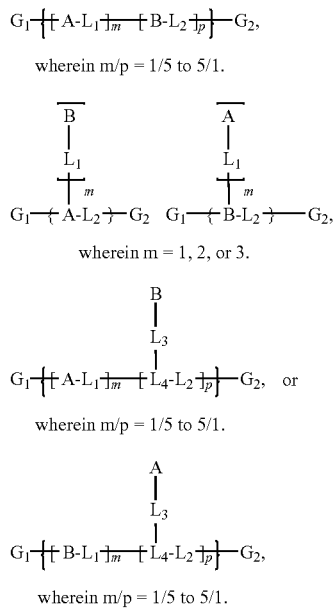

A is an ETM as described herein. B is a HTM as described herein. $L_1$, $L_2$ and $L_3$ are flexible linker moieties as described herein. $L_4$ is a branching unit moiety (BUM) to which two or more flexible linker moieties can be attached. Examples of suitable BUMs include a 1,3,5-trisubstituted phenyl ring (1) and a trisubstituted cyclohexyl ring (2) which are shown below. $G_1$ and $G_2$ are end groups which terminate (cap) the polymer. Suitable G groups include, but are not limited to, groups such as H, alkyl (e.g., 1 to 6 carbon branched/unbranched, substituted/unsubstituted alkyl groups), aryl (e.g., 5 or 6 carbon substituted/unsubstituted aryl rings), and the like.

The compounds of the present invention form amorphous (also referred to herein as isotropic) materials, including amorphous films, which are useful as bipolar charge-transport host materials. Formation of the compounds via chemical modification as described herein represents a viable solution to circumvent the phase-separation problem associated with physical mixing of charge-transport (electron/hole) materials. The hybrid materials of the present invention exhibit elevated $T_g$ and increased stability against crystallization compared to the ETMs and HTMs as separate entities.

The hybrid host materials comprising compounds of the present invention exhibit stability against phase separation, elevated glass transition temperature ($T_g$ from 50 to 200° C.), morphological stability against crystallization, and isolation of the π-systems. They are designed to spread out excitons across the emitter layer by balancing electron and hole fluxes so that the OLED device efficiency and lifetime can be substantially improved. These are improved properties relative to those obtained by physical blending and other chemical modification approaches directed to tunable charge injection and transport properties and prevention of charge and exciton accumulations at interfaces.

DETAILED DESCRIPTION OF THE INVENTION

Figure 1:
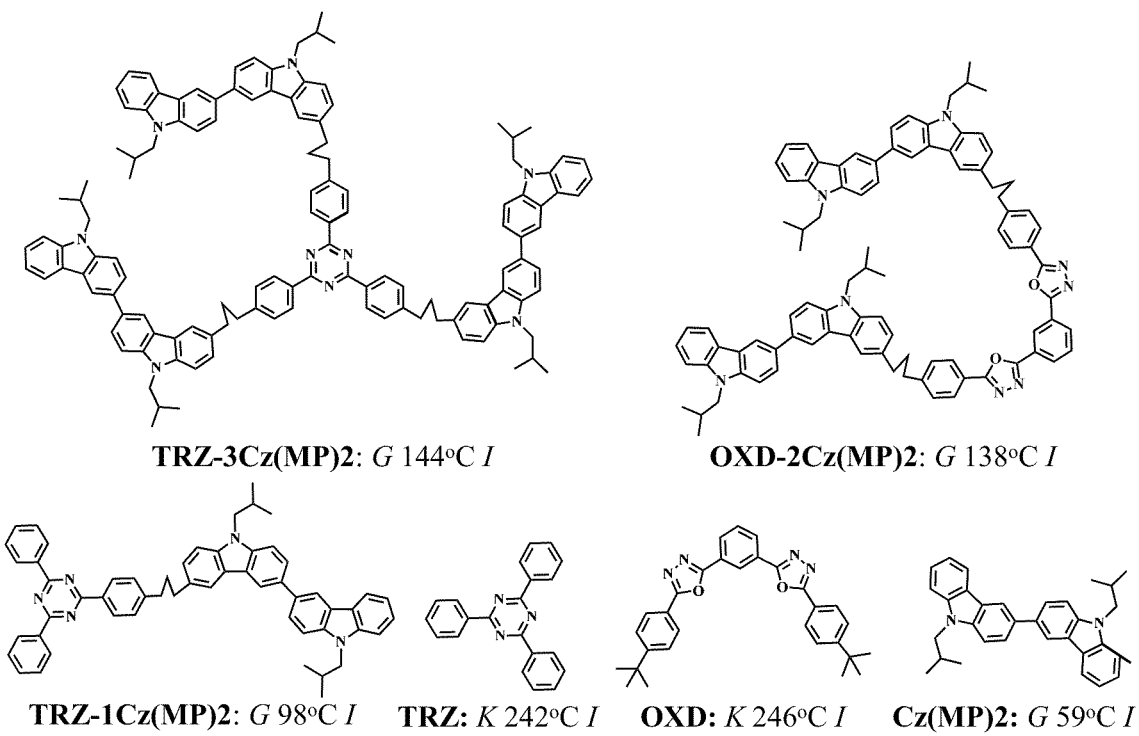
FIG. 1. Representative non-conjugated bipolar compounds as well as independent electron- and hole-transport moieties with their thermal transition temperatures determined by DSC heating scans shown in FIG. 3. Symbols: G, glassy; K, crystalline; I, isotropic.

The present invention provides compounds (which includes polymers), and compositions comprising the compounds, which can be used as host materials in electroluminescent devices. In one embodiment, the compounds have the following general structures:

or

The compounds comprise at least one electron-transporting moiety (ETM) (A) and at least one hole-transporting moiety (HTM) (B) connected by a linker moiety (L). The number of possible HTMs (x) per ETM, or the number of possible ETMs (y) per HTM is dependant on the structure of the ETM and HTM in the hybrid molecule, typically ranging from 1 to 10. Both the ETMs and HTMs are semiconducting with an electron and a hole mobility, respectively, in the range from $10^{-7}$ to $10^{-2}$ cm$^2$/V·s.

The term "electron-transporting moiety" as used herein means electron-deficient and electron-accepting moieties with LUMO levels suitable for injection of electrons from common cathodes. For example, LUMO levels of −2.0 to −3.5 eV are suitable. Suitable ETMs can be found in compounds belonging to, for example, the following general classes: triazine, triazole, oxadiazole, benzimidazole, phenathroline, pyridine, pyrazine, triphenylborane, triarylphosphine oxide, tetraarylsilane, and the like. Examples of ETMs with suitable $E_T$ (in eV) (for example, minimum $E_T$ is 2.7 eV for blue emission, 2.5 eV for green emission, and 2.0 eV for red emission) include, but are not limited to, the following moieties, where the dotted lines illustrate, but are not intended to limit, the potential linking sites.

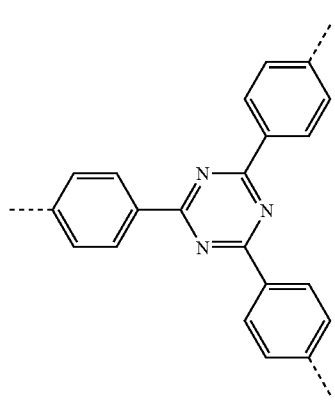

E-1

$E_T = 3.05$ eV

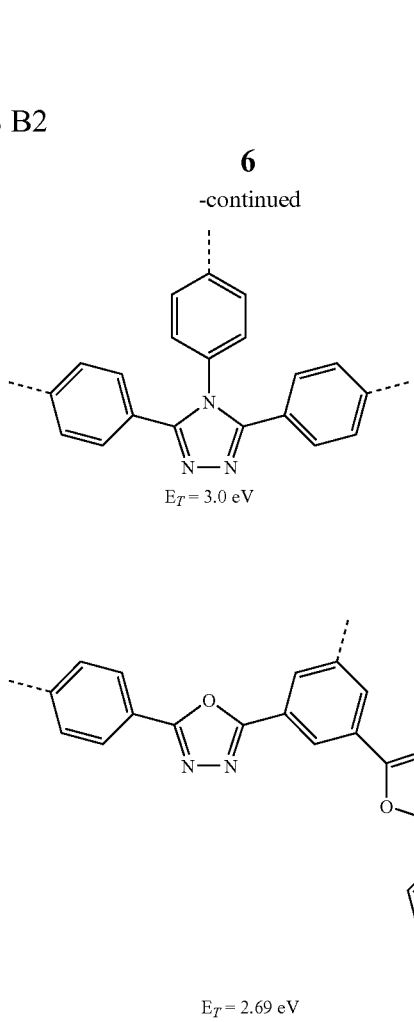

E-2

$E_T = 3.0$ eV

E-3

$E_T = 2.69$ eV

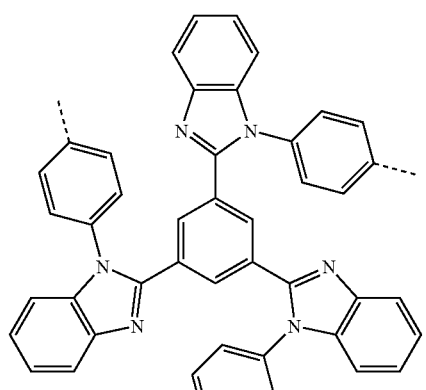

E-4

$E_T = 2.74$ eV

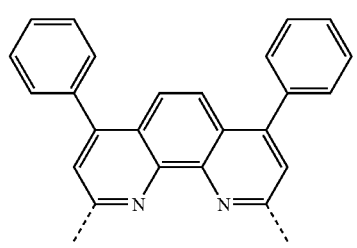

E-5

$E_T = 2.59$ eV

E-6
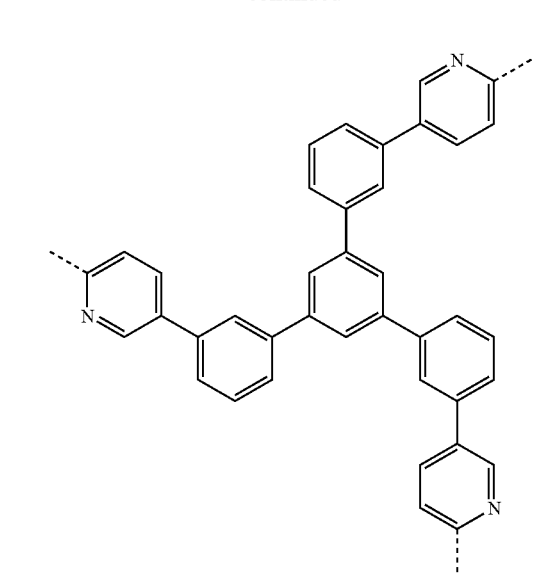
$E_T = 2.78$ eV
E-7
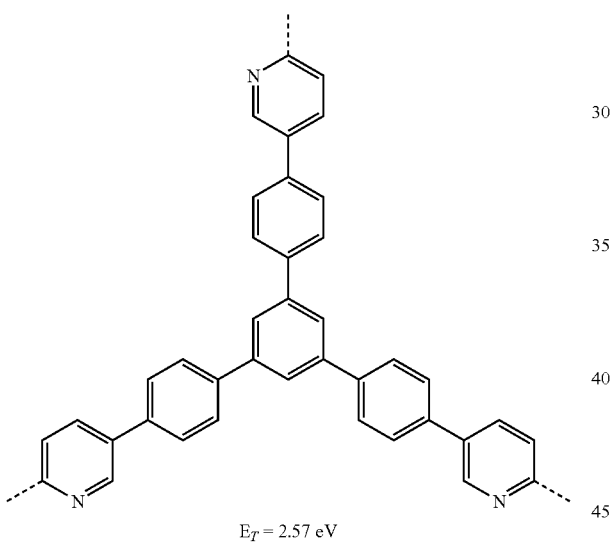
$E_T = 2.57$ eV
E-8
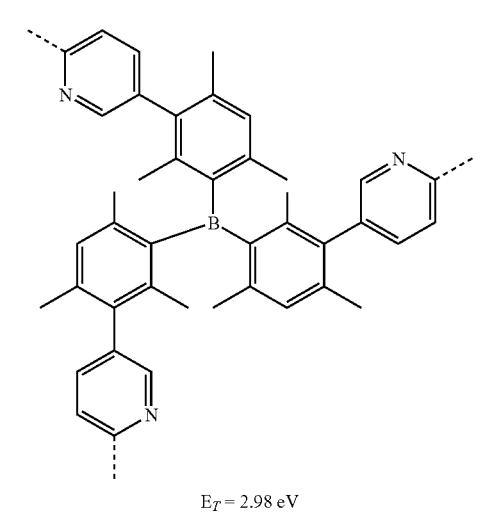
$E_T = 2.98$ eV
E-9
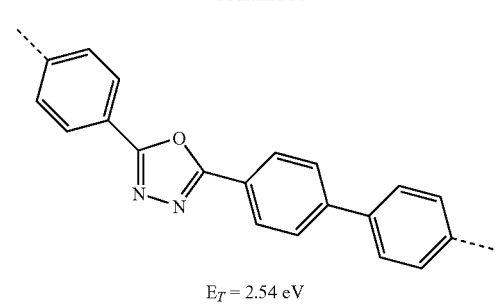
$E_T = 2.54$ eV
E-10
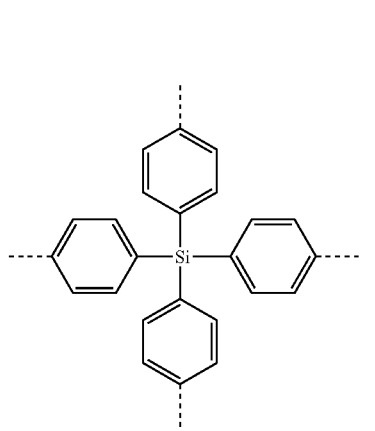
$E_T = 2.76$ eV
E-11
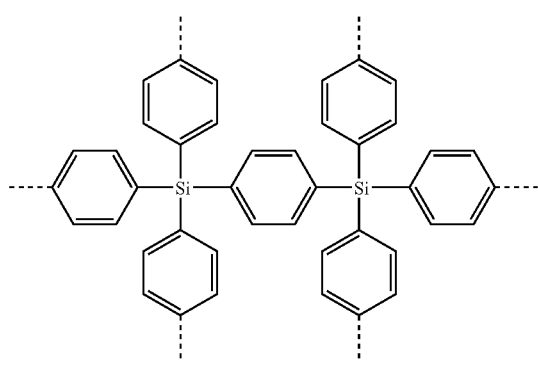
$E_T = 3.5$ eV
E-12
$E_T = 3.5$ eV E-13
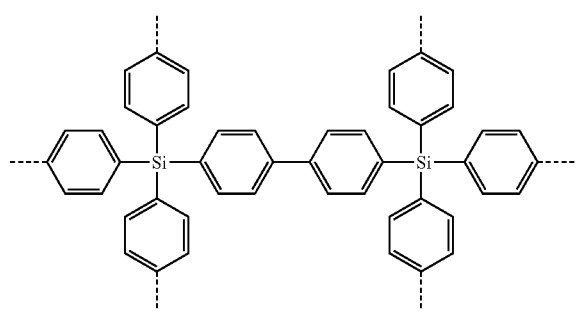
$E_T = 2.76$ eV
E-14
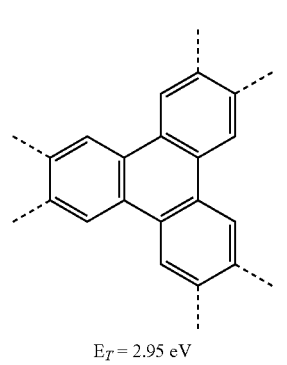
$E_T = 2.95$ eV
E-15
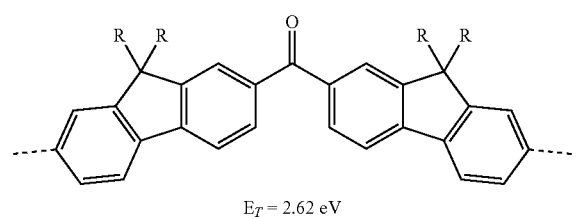
$E_T = 2.62$ eV
E-16
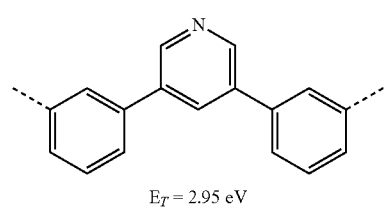
$E_T = 2.95$ eV
E-17
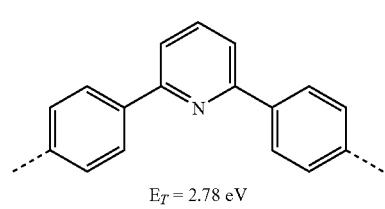
$E_T = 2.78$ eV
E-18
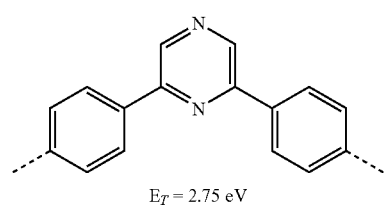
$E_T = 2.75$ eV
E-19
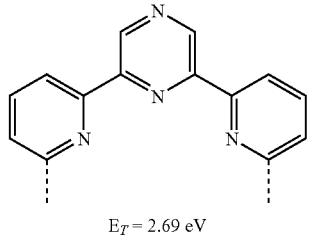
$E_T = 2.69$ eV
E-20
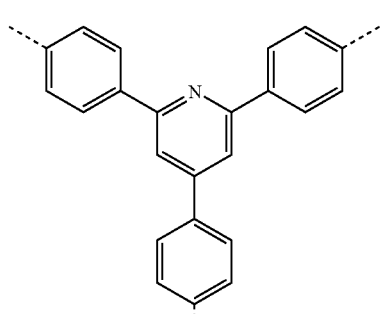
$E_T = 2.75$ eV
E-21
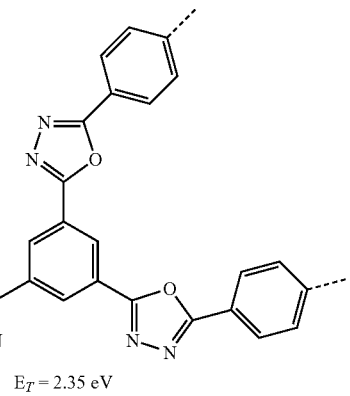
$E_T = 2.35$ eV
E-22
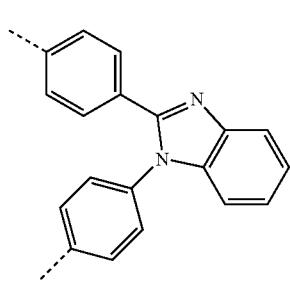
$E_T = 2.79$ eV
E-23
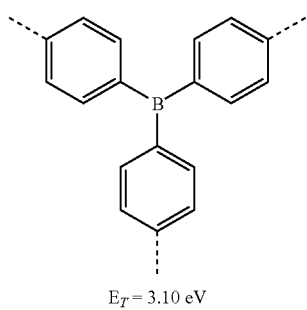
$E_T = 3.10$ eV

E-24

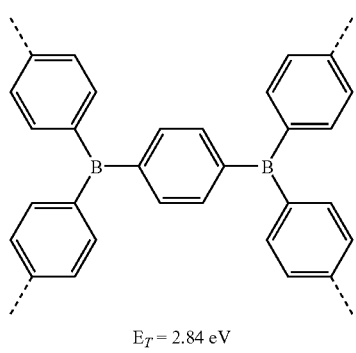

$E_T = 2.84$ eV

E-25

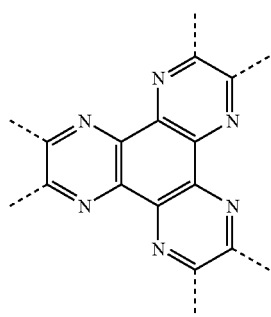

$E_T = 2.68$ eV

E-26

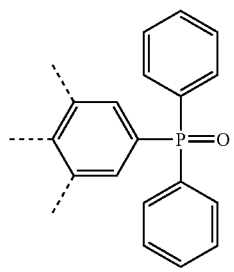

$E_T = 3.43$ eV

E-27

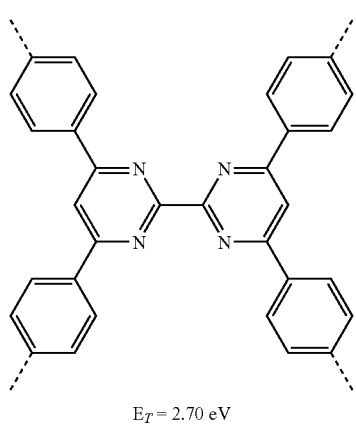

$E_T = 2.70$ eV

E-28

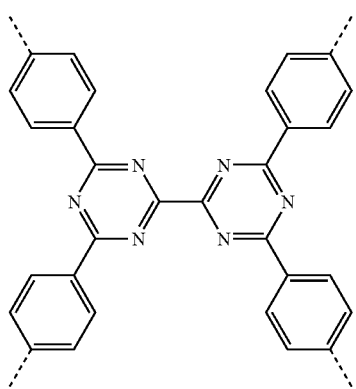

$E_T = 2.74$ eV

The triplet energies of E-1 through E-15 were experimentally determined. The triplet energies of E-16 through E-28 were calculated using the Gaussian 2003 software package.

The term "hole-transporting moiety" as used herein means electron-rich and electron-donating moieties with HOMO energy levels suitable for efficient injection of holes into them from common anodes. For example, HOMO levels of −4.5 to −6.0 eV are suitable. Suitable HTMs can be found in compounds belonging to, for example, the following general classes: pyrrole, furan, carbazole, dibenzofuran, dibenzothiophene, dibenzoselenophene, dibenzosilole, dithienopyrrole, dithienothiophene, triphenylamine, triphenylphosphine, phenoxazine, thianthrene, dibenzodioxin, fluorene, and the like. Examples of HTMs with suitable $E_T$ (in eV) (for example, minimum $E_T$ is 2.7 eV for blue emission, 2.5 eV for green emission, and 2.0 eV for red emission) include, but are not limited to, the following moieties, where the dotted lines illustrate, but are not intended to limit, the potential linking sites. Accordingly, a potential binding site can be present at any chemical bonding site on an ETM or HTM.

H-1

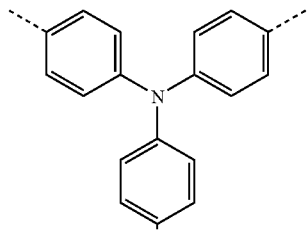

$E_T = 3.03$ eV

H-2

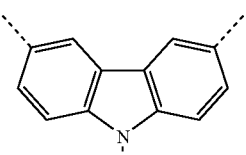

$E_T = 3.04$ eV

-continued
H-3
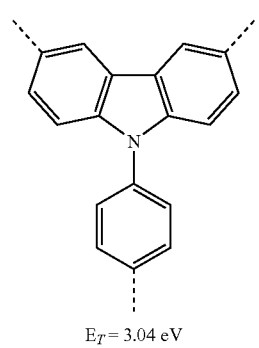
$E_T = 3.04$ eV
H-4
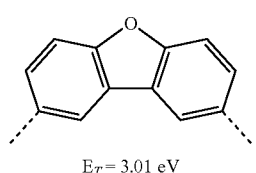
$E_T = 3.01$ eV
H-5
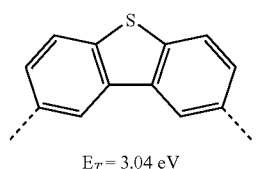
$E_T = 3.04$ eV
H-6
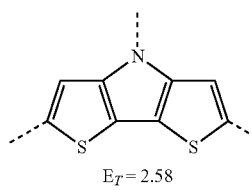
$E_T = 2.58$
H-7
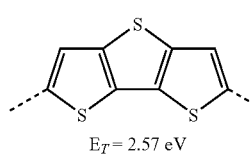
$E_T = 2.57$ eV
H-8
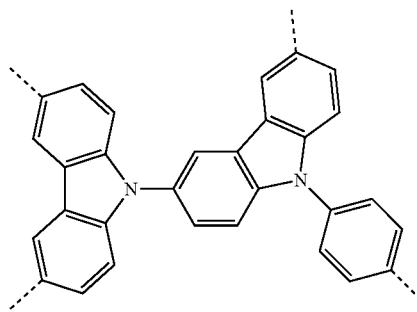
$E_T = 2.99$ eV
-continued
H-9
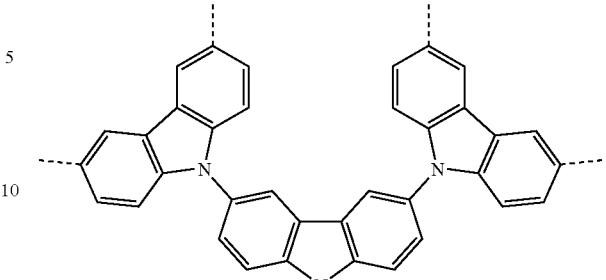
$E_T = 2.94$ eV
H-10
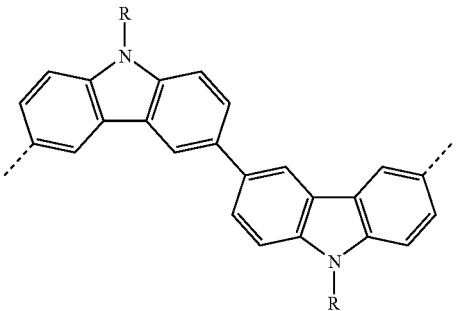
$E_T = 2.75$ eV
H-11
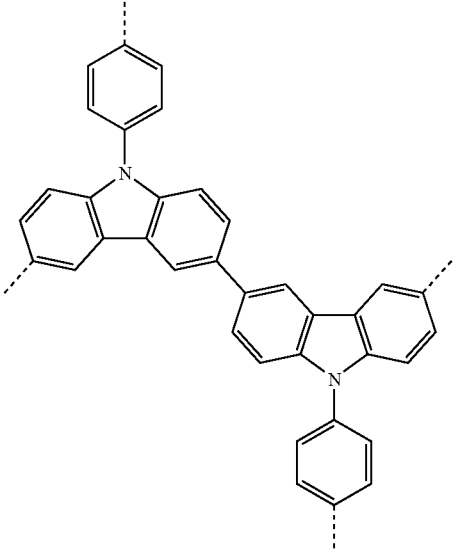
$E_T = 2.75$ eV -continued
H-12
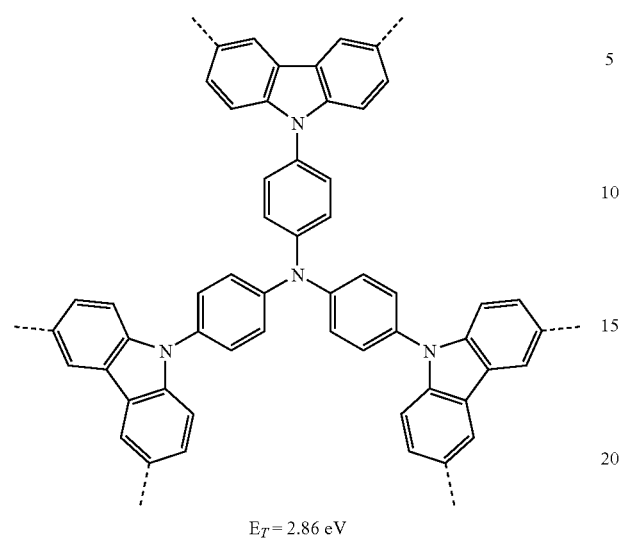
$E_T = 2.86$ eV
H-13
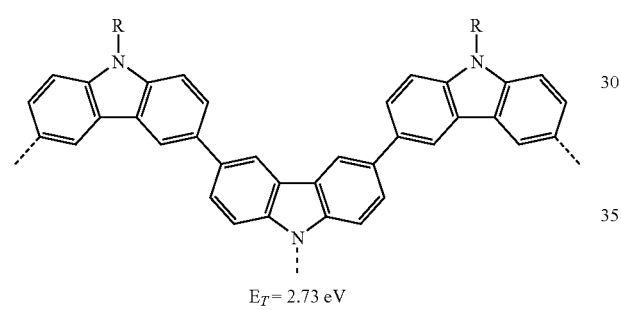
$E_T = 2.73$ eV
H-14
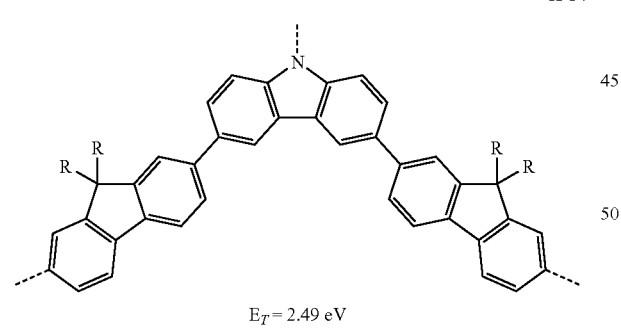
$E_T = 2.49$ eV
H-15
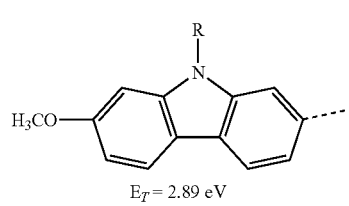
$E_T = 2.89$ eV
-continued
H-16
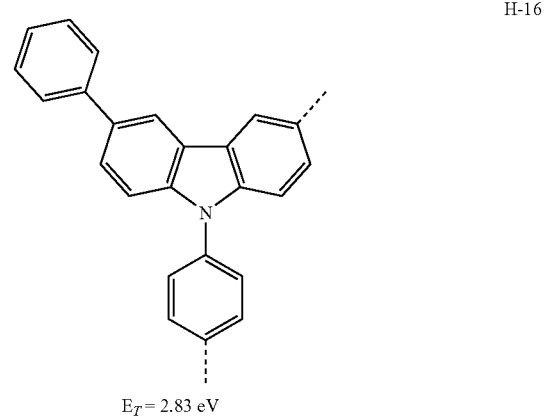
$E_T = 2.83$ eV
H-17
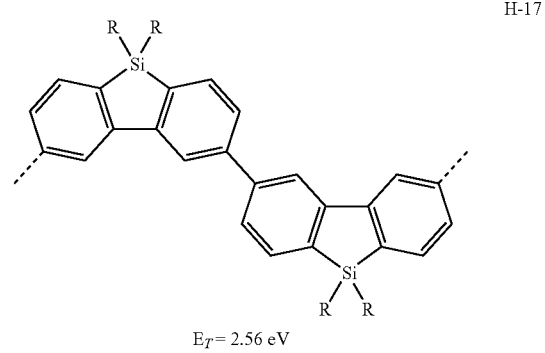
$E_T = 2.56$ eV
H-18
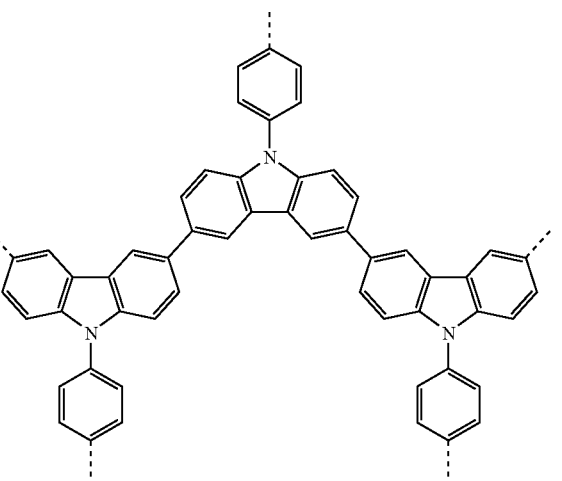
$E_T = 2.73$ eV
H-19
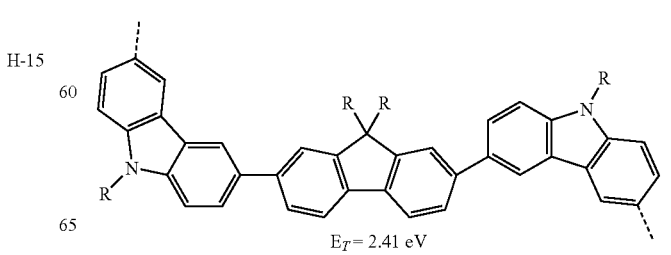
$E_T = 2.41$ eV

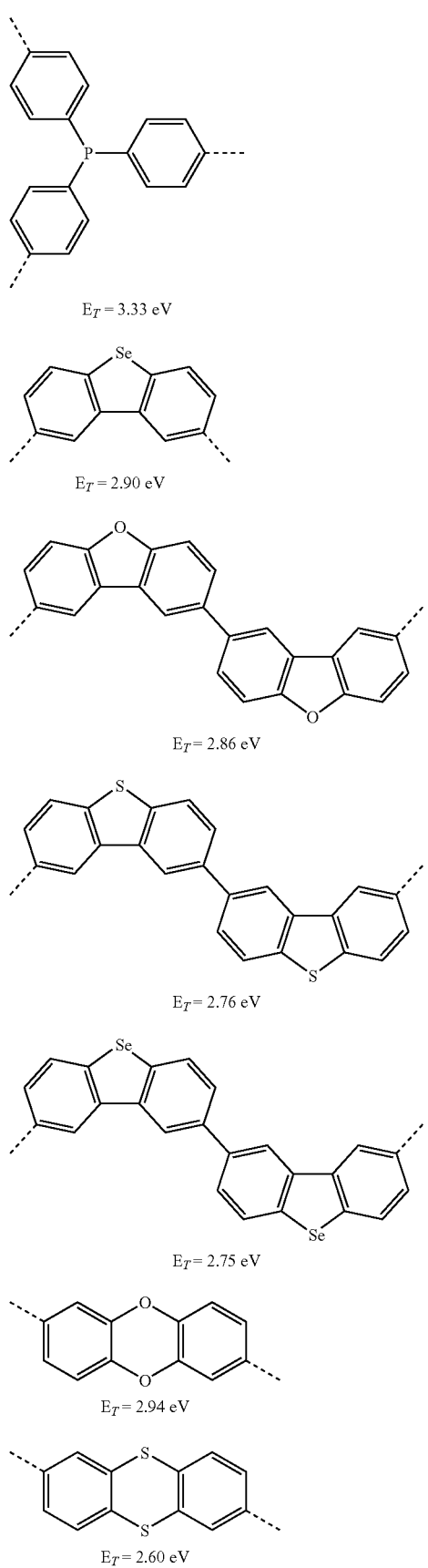

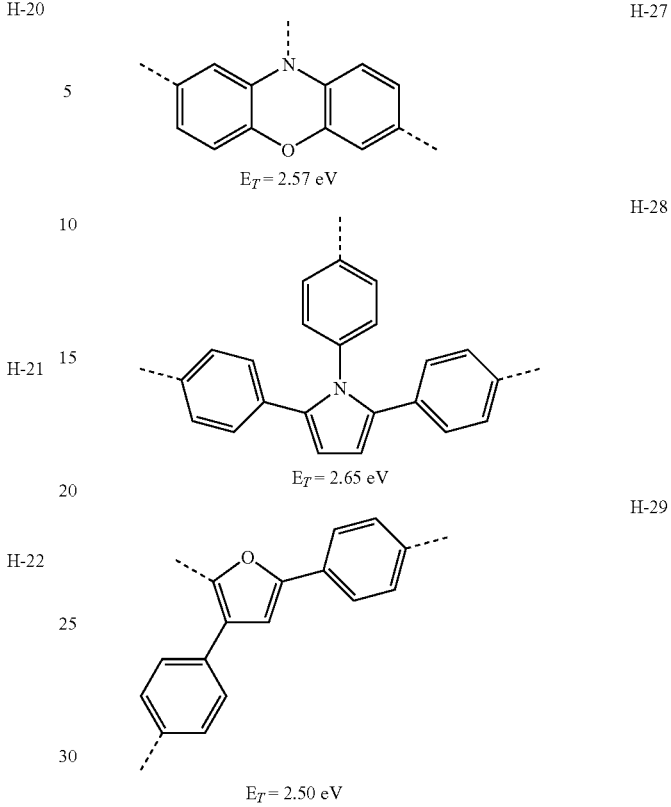

The triplet energies of H-1 through H-14 were experimentally determined. The triplet energies of H-15 through H-29 were calculated using the Gaussian 2003 software package. The substituent groups denoted as R in H-10, H-13, H-14, H-15, H-17 and H-19 are independently alkyl (e.g., 1 to 6 carbon branched/unbranched, substituted/unsubstituted alkyl groups), or aryl (e.g., 5 or 6 carbon substituted/unsubstituted aryl rings) groups.

The term "linker" as used herein means a moiety which is a flexible chain consisting of a series of σ-bonds, such as poly(methylene), poly(methyleneoxide), poly(ethyleneoxide), and poly(dialkylsiloxane). A linker moiety is used to connect (by formation of chemical bonds) the ETM and HTM moieties. An ETM and a HTM are each chemically bonded to one of the ends of a linker. The linker electronically decouples the two π-systems of the ETM and HTM, thereby allowing the structural elements to retain their individual electronic characteristics, such as HOMO/LUMO energy and $E_T$. The linker also influences the morphology of the compounds. For example, the linker aids in preventing crystallization. In addition to precluding phase separation, the flexible linkages serve to increase entropy because of the more abundant conformations, which is conducive to solubility in benign solvents to facilitate materials purification and solution processing. Examples of linker moieties useful in the present invention include, but are not limited to, the following:

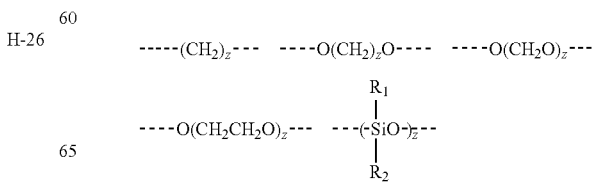

(The dotted lines represent, but are not intended to limit, potential linking sites on the linker moieties.)

In one embodiment, z is any integer from 1-10. In another embodiment, z is any integer from 3-7. In both embodiments, R1 and R2 are, independently, alkyl groups.

The compounds of the present invention involve chemically bonding electron-transporting and hole-transporting moieties via a linker resulting in interruption of π-conjugation of the individual moieties to produce compounds which are useful as hybrid materials. The use of a linker to bind the ETM and the HTM moieties allows both the moieties to retain their individual HOMO/LUMO levels and $E_T$ in the hybrid material and imparts bipolar-transport capability to the hybrid materials. For example, injection of electrons and holes are determined primarily by the LUMO and HOMO levels, respectively. The hybrid molecule's energy levels receptive to charge injection are furnished by its ETM and HTM moieties. Further, charge-transport properties are determined by these two energy levels as well as the overlap of molecular orbitals and reorganization energy, both affected by film morphology.

In one embodiment, the compound has one of the following structural formulas:

  (i)

or

  (ii)

In these general structures, A is an electron-transporting moiety comprising from 1 to 20, and all integers and ranges from 1 to 20, conjugated 5 or 6 member hydrocarbon or heterocyclic rings and has a lowest unoccupied molecular orbital energy of from −2.0 to −3.5 eV, including all values to 0.1 eV and ranges therebetween, and triplet energy of from 2.0 to 3.5 eV, including all values to 0.1 eV and ranges therebetween. B is a hole-transporting moiety, comprising from 1 to 20, and all integers and ranges from 1 to 20, conjugated 5 or 6 member hydrocarbon or heterocyclic rings, and has a highest occupied molecular orbital energy of from −4.5 to −6.0 eV, including all values to 0.1 eV and ranges therebetween, and triplet energy of from 2.0 to 3.5 eV, including all values to 0.1 eV and ranges therebetween. L is a flexible linker moiety connecting the A and B moieties comprising from 1 to 10, and all integers and ranges from 1 to 10, repeating units of methylene, methyleneoxide, ethyleneoxide, or dialkylsiloxane, and combinations thereof. The linker prevents conjugation of the A and B moieties. The values of x and y are any integers from 1 to 10, including all integers therebetween. The compound exhibits an amorphous phase which is stable for at least 6 months. In another embodiment, the present invention provides a host material composition comprising a compound (or a combination of the compounds) described in this embodiment.

In one embodiment, A is an electron-transporting moiety comprising from 2 to 10 conjugated 5 or 6 member hydrocarbon or heterocyclic rings, and the electron-transporting moiety has a lowest unoccupied molecular orbital energy of from −2.4 to −3.0 eV and triplet energy of from 2.0 to 3.5 eV. B is a hole-transporting moiety comprising from 2 to 10 conjugated 5 or 6 member hydrocarbon or heterocylic rings, and the hole-transporting moiety has a highest occupied molecular orbital energy of from −5.0 to −5.8 eV and triplet energy of 2.0 to 3.5 eV. L is a flexible linker moiety connecting the A and B moieties, and the linker moiety comprises from 2 to 6 repeating units of methylene, methyleneoxide, ethyleneoxide, or dialkylsiloxane units. The linker prevents conjugation of the A and B moieties. The values of x and y are any integers from 1 to 5. The compound exhibits an amorphous phase which is stable for at least 6 months.

In another embodiment, the compound is selected from the group consisting of 2,4,6-tris(4-(3-(6-(9-(2-methylpropyl)carbazol-3-yl)-9-(2-methylpropyl)carbazol-3-yl)propyl)phenyl)-1,3,5-triazine (TRZ-3Cz(MP)2), 2-(4-(3-(6-(9-(2-methylpropyl)carbazol-3-yl)-9-(2-methylpropyl)carbazol-3-yl)propyl)phenyl)-4,6-diphenyl-1,3,5-triazine (TRZ-1Cz(MP)2); Tris(4-(3-(6-(9-(2-methylpropyl)carbazol-3-yl)-9-(2-methylpropyl) carbazol-3-yl)propyl)phenyl)amine (TPA-3Cz(MP)2); 1,3,5-tris(4-(3-(6-(9-(2-methylpropyl)carbazol-3-yl)-9-(2-methylpropyl) carbazol-3-yl)propyl)phenyl)benzene (TPB-3Cz(MP)2); 2,4,6-tris(4-(3-(3,6-bis(9-(2-methylpropyl)carbazol-3-yl)carbazol-9-yl)propyl)phenyl)-1,3,5-triazine (TRZ-3Cz(N)Cz(MP)2); 2,4,6-tris(4-(3-(6-(7-(9-(2-methylpropyl)carbazol-3-yl)-9,9-bis(2-methylpropyl)fluoren-2-yl)-9-(2-methylpropyl)carbazol-3-yl)propyl)phenyl)-1,3,5-triazine (TRZ-3Cz(MP)2F(MP)); 2,4,6-tris(4-(3-(7-methoxy-1-9-methylcarbazol-2-yl)propyl)phenyl)-1,3,5-triazine (TRZ-3Cz(Me)OMe); 1,3-bis(5-(4-(3-(6-(9-(2-methylpropyl)carbazol-3-yl)-9-(2-methylpropyl)carbazol-3-yl)propyl)phenyl)-1,3,4-oxadiazol-2-yl)benzene (OXD-2Cz(MP)2); 1,3-bis(5-(4-(3-(3,6-bis(carbazol-9-yl)carbazol-9-yl)propyl)phenyl)-1,3,4-oxadiazol-2-yl)benzene (OXD-2Cz3); 2-(4-(3-(dibenzofuran-2-yl)propyl)phenyl)-4,6-diphenyl-1,3,5-triazine (TRZ-1DBF1); 2,4,6-Tris(4-(3-(dibenzofuran-2-yl)propyl)phenyl)-1,3,5-triazine (TRZ-3DBF1); 2-(4-(3-(8-(dibenzofuran-2-yl)dibenzofuran-2-yl)propyl)phenyl)-4,6-diphenyl-1,3,5-triazine (TRZ-1DBF2); 2,4,6-tris(4-(3-(8-(dibenzofuran-2-yl)dibenzofuran-2-yl)propyl)phenyl)-1,3,5-triazine (TRZ-3DBF2); 3,5-Bis(4-(3-(8-(dibenzofuran-2-yl)dibenzofuran-2-yl)propyl)phenyl)-4-phenyl-1,2,5-triazole (TAZ-2DBF2); and 1,3-Bis(4-(3-(8-(dibenzofuran-2-yl)dibenzofuran-2-yl)propyl)phenyl)-1,3,4-oxadiazol-2-yl)benzene (OXD-2DBF2).

In one embodiment, the compound is present as one of the compounds described herein or a combination thereof.

In another embodiment, the compounds of the present invention are bipolar polymers and compositions comprising the bipolar polymers, which can be used as host materials in electroluminescent devices. The bipolar polymers have the following general structures:

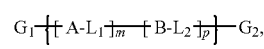  i wherein m/p = 1/5 to 5/1.

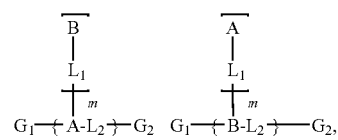  ii wherein m = 1, 2, or 3.

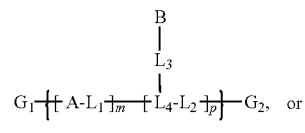  iii wherein m/p = 1/5 to 5/1.

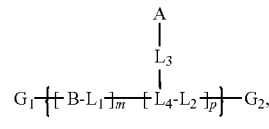  iv wherein m/p = 1/5 to 5/1.

A is an ETM as described herein. B is a HTM as described herein. $L_1$, $L_2$ and $L_3$ are flexible linker moieties as described herein. $L_4$ is a branching unit moiety (BUM) to which two or more flexible linker moieties can be attached. Examples of suitable BUMs include a 1,3,5-trisubstituted phenyl ring (1) and a trisubstituted cyclohexyl ring (2) which are shown below. $G_1$ and $G_2$ are end groups which terminate (cap) the polymer. Suitable G groups include, but are not limited to, groups such as H, alkyl (e.g., 1 to 6 carbon branched/unbranched, substituted/unsubstituted alkyl groups), aryl (e.g., 5 or 6 carbon substituted/unsubstituted aryl rings), and the like.

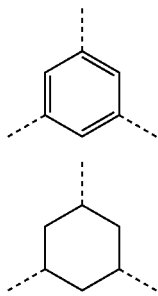

In one embodiment, the present invention provides a polymer having one of the structural formulas (i, ii, iii, or iv) represented above. A is an electron-transporting moiety comprising from 1 to 20, including all integers and ranges from 1 to 20, conjugated 5 or 6 member hydrocarbon or heterocyclic rings, and has a lowest unoccupied molecular orbital energy of from −2.0 to −3.5 eV, including all values to 0.1 eV and ranges therebetween, and triplet energy of from 2.0 to 3.5 eV, including all values to 0.1 eV and ranges therebetween. B is a hole-transporting moiety, comprising from 1 to 20, including all integers and ranges from 1 and 20, conjugated 5 or 6 member hydrocarbon or heterocyclic rings, and has a highest occupied molecular orbital energy of from −4.5 to −6.0 eV, including all values to 0.1 eV and ranges therebetween, and triplet energy from of 2.0 to 3.5 eV, including all values to 0.1 eV and ranges therebetween. $L_1$, $L_2$, and $L_3$ are flexible linker moieties connecting the A and/or B and/or G moieties, and, independently, comprise from 1 to 10, including all integers and ranges therebetween, repeating units of methylene, methyleneoxide, ethyleneoxide, or dialkylsiloxane units, and combinations thereof. The flexible linker moieties prevent conjugation of the A and B moieties. $L_4$ is a branching unit moiety, and comprises a 5 or 6 member ring which can be saturated or unsaturated. $G_1$ and $G_2$ are end groups which terminate the polymer, which are independently selected from the group consisting of H, alkyl, and aryl groups. The polymer exhibits an amorphous phase which is stable for at least 6 months.

In another embodiment, A is an electron-transporting moiety comprising from 2 to 10 conjugated 5 or 6 member hydrocarbon or heterocyclic rings, and the electron-transporting moiety has a lowest unoccupied molecular orbital energy of from −2.4 to −3.0 eV and triplet energy of from 2.0 to 3.5 eV. B is a hole-transporting moiety, comprising from 2 to 10 conjugated 5 or 6 member hydrocarbon or heterocylic rings, and the hole-transporting moiety has a highest occupied molecular orbital energy of from −5.0 to −5.8 eV and triplet energy of from 2.0 to 3.5 eV. $L_1$, $L_2$ and $L_3$ are flexible linker moieties connecting the A and/or B and/or G moieties, and the linker moieties comprises from 2 to 6 repeating units of methylene, methyleneoxide, ethyleneoxide, or dialkylsiloxane and prevents conjugation of the A and B moieties. $L_4$ is a branching unit moiety, wherein the branching unit moiety is a 5 or 6 member ring which can be saturated or unsaturated. $G_1$ and $G_2$ are end groups which terminate the polymer, and the end groups are independently selected from the group consisting of H, alkyl, or aryl groups. The polymer exhibits an amorphous phase which is stable for at least 6 months.

In another embodiment, the polymer is selected from the group consisting of Polymer 1 (poly(iso-butylcarbazole-co-biphenylpyridine)), Polymer 2 (poly(carbazolylphenylene-co-biphenylpyridine)), and Polymer 3 (poly(triazinylcarbazole)). Polymer 1, Polymer 2 and Polymer 3 are described in Example 1.

Examples of compounds of the present invention include, but are not limited to, the following:

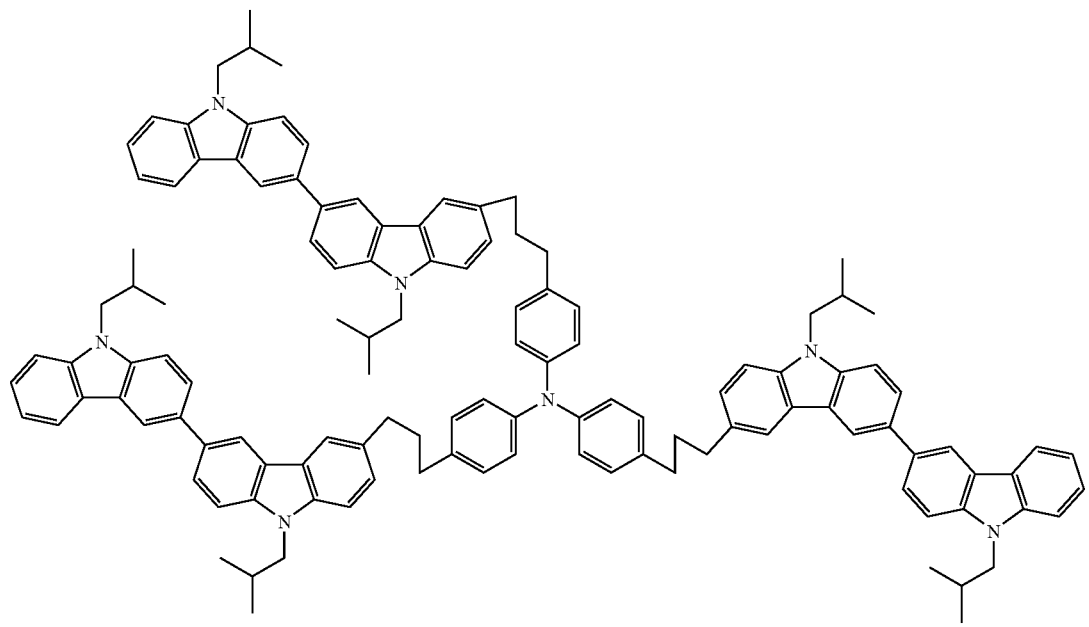

TPA-3Cz(MP)2: $T_g$ = 135° C., $E_T$ = 2.76 eV

-continued
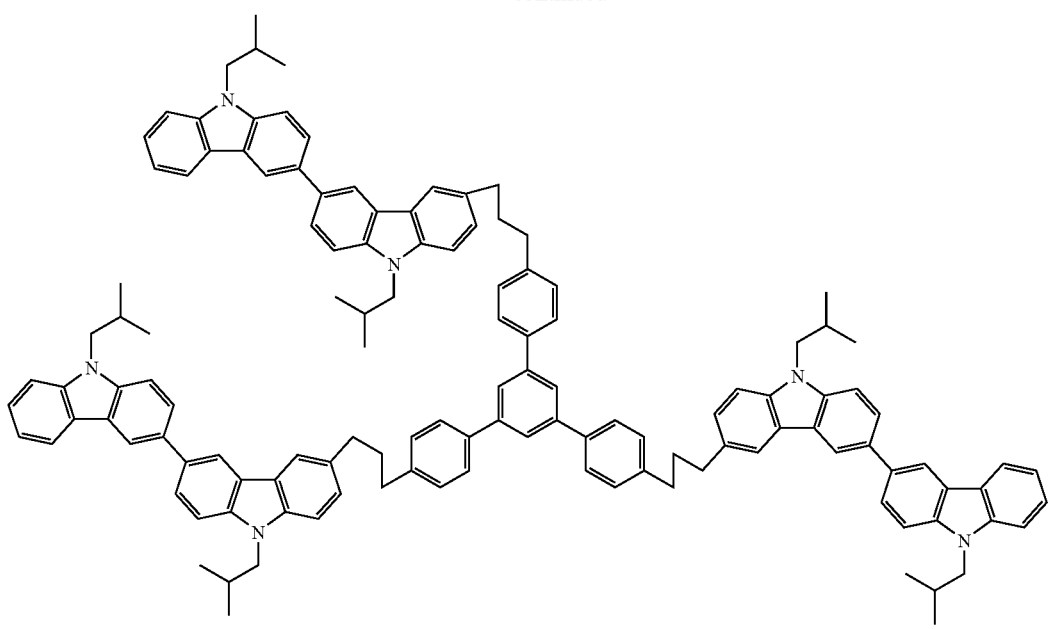
TPB-3Cz(MP)2: $T_g = 140°$ C., $E_T = 2.76$ eV
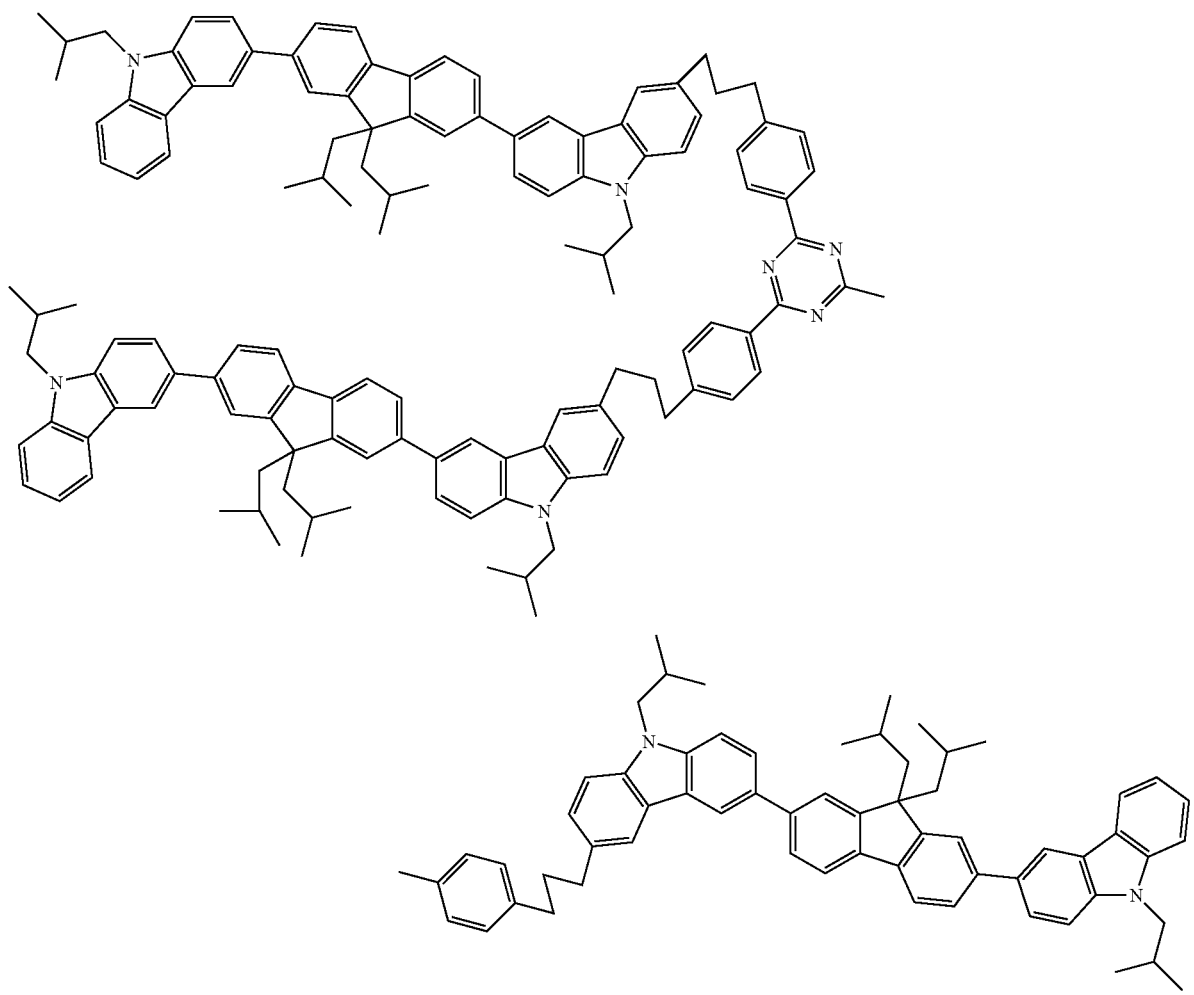
TRZ-3Cz(MP)2F(MP): $T_g = 155°$ C., $E_T = 2.41$ eV -continued
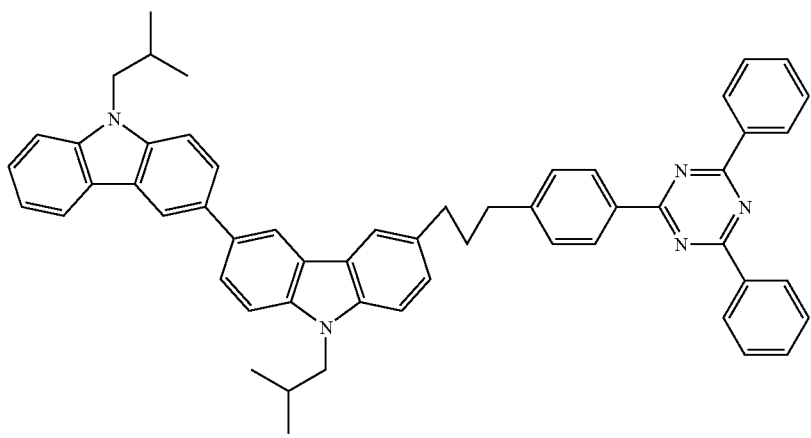
TRZ-1Cz(MP)2: $T_g$ = 98° C., $E_T$ = 2.76 eV
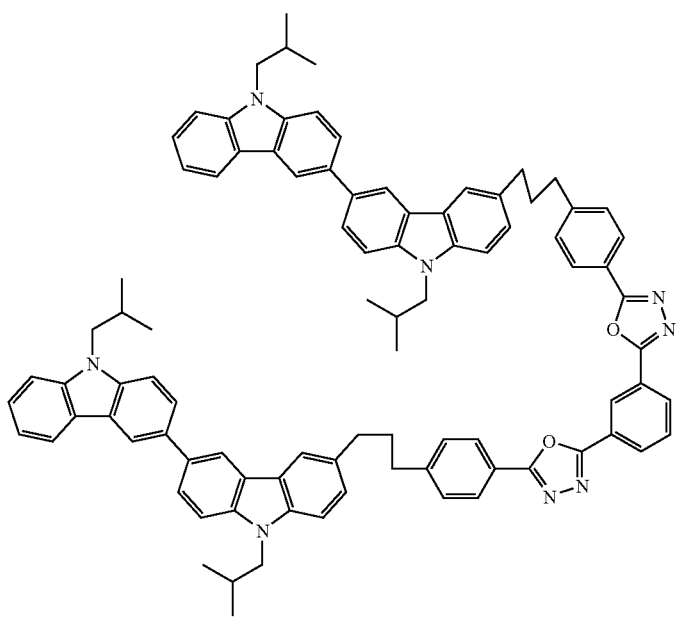
OXD-2Cz(MP)2: $T_g$ = 138° C., $E_T$ = 2.71 eV -continued
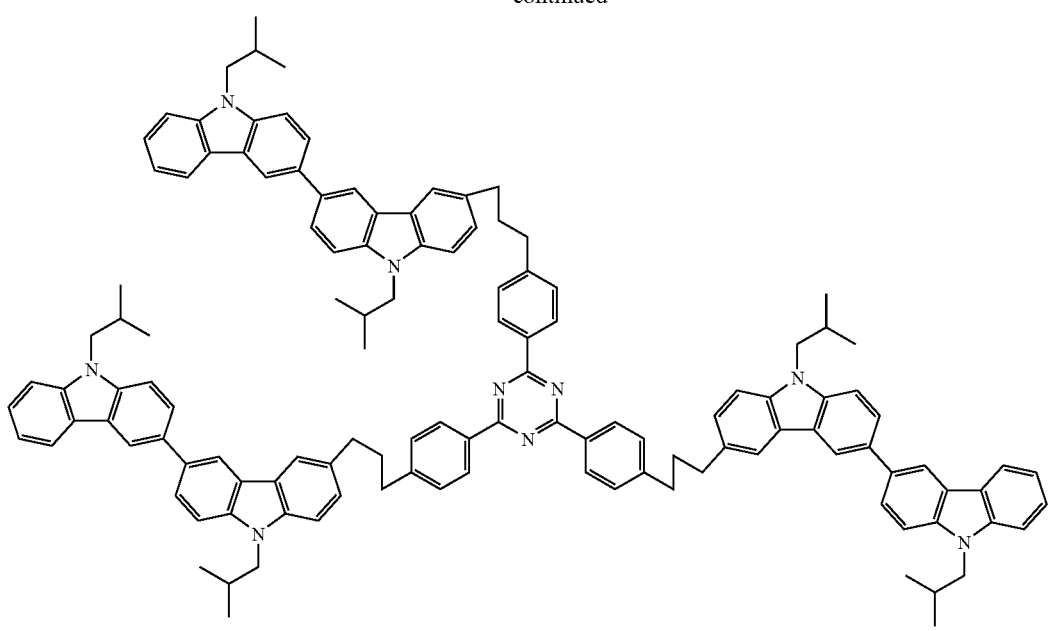
TRZ-3Cz(MP): $T_g$ = 144° C., $E_T$ = 2.74 eV
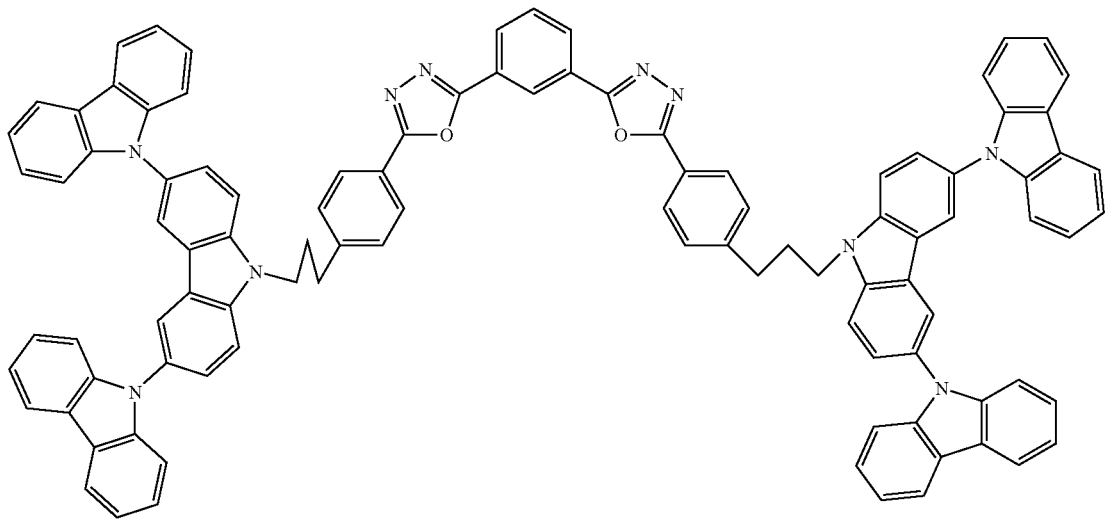
OXD-2Cz3: $T_g$ = 198° C., $E_T$ = 2.69 eV -continued
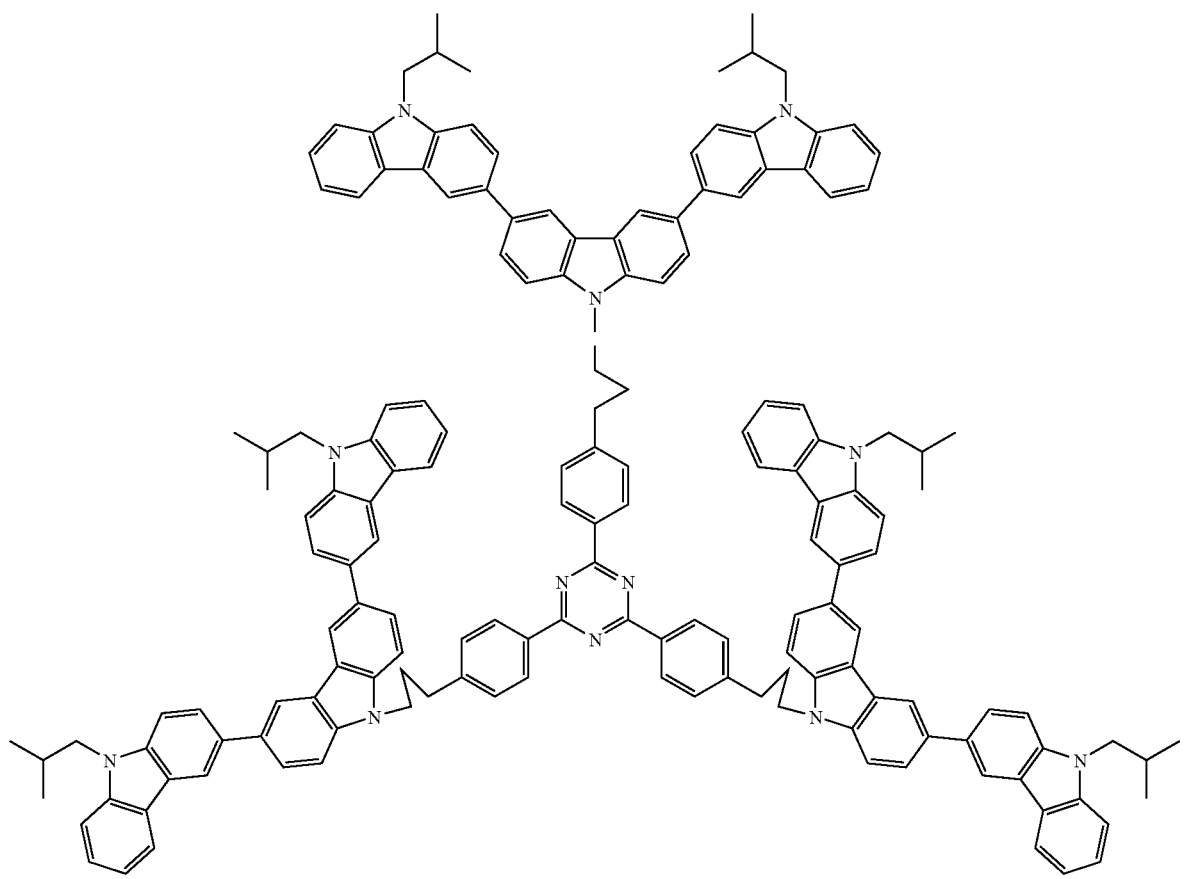
TRZ-3Cz(N)Cz(MP)2: $T_g$ = 190° C., $E_T$ = 2.73 eV
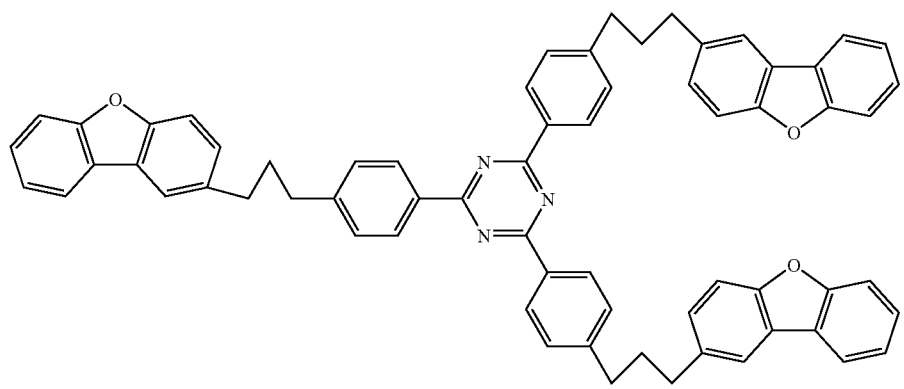
TRZ-3DBF1: $T_g$ = 43° C., $E_T$ = 3.01 eV
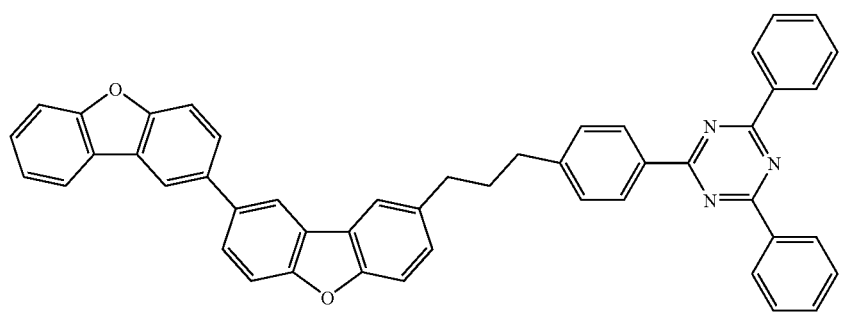
TRZ-1DBF2: $T_g$ = 84° C., $E_T$ = 2.86 eV -continued
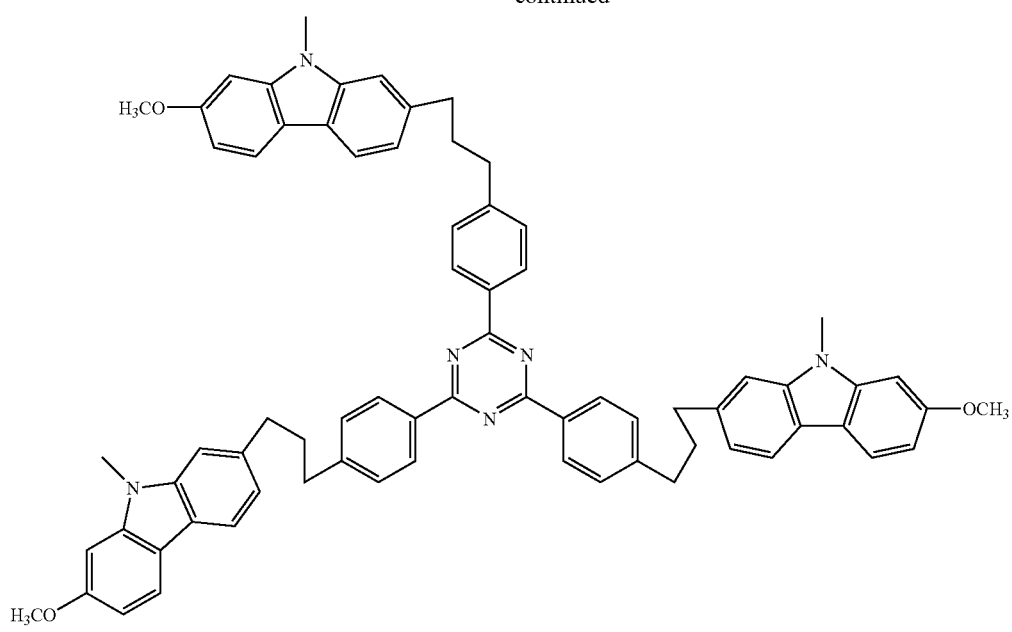
TRZ-3Cz(Me)OMe: $T_g$ = 76° C., $E_T$ = 2.89 eV
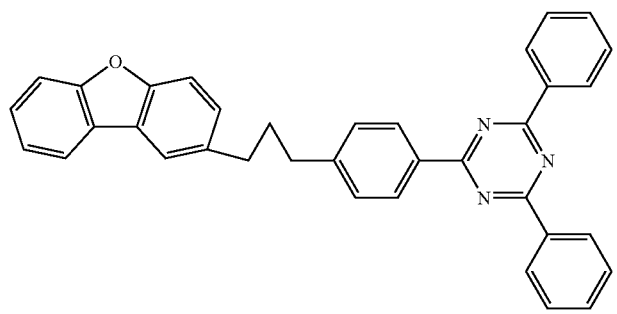
TRZ-1DBF1: Tg = 37° C., $E_T$ = 3.01 eV
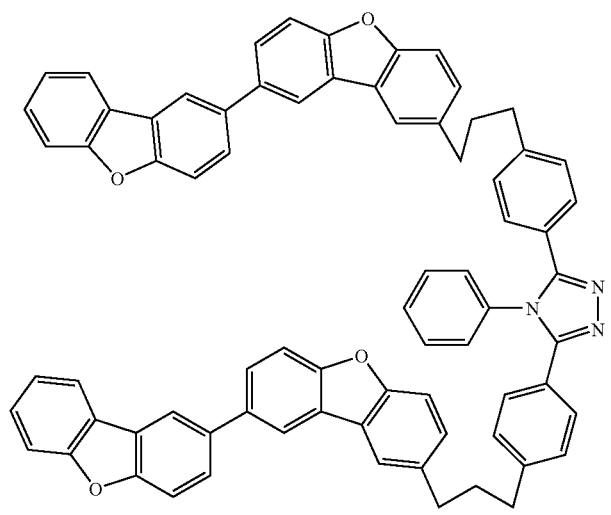
TAZ-2DBF2: Tg = 118° C., $E_T$ = 2.86 eV -continued
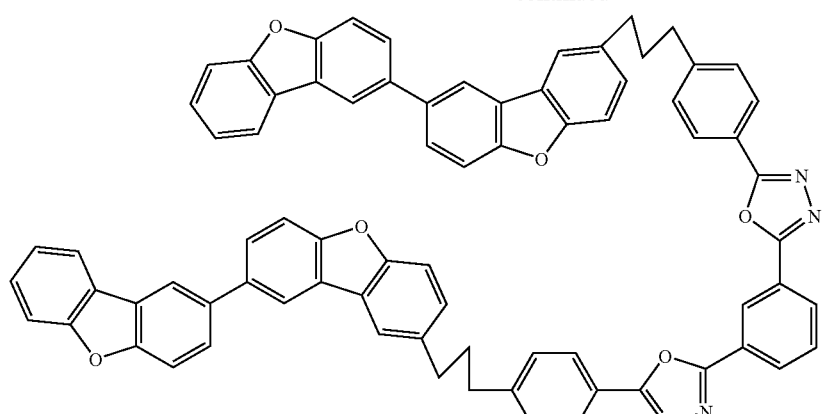
OXD-2DBF2: Tg = 124° C., $E_T$ = 2.69 eV
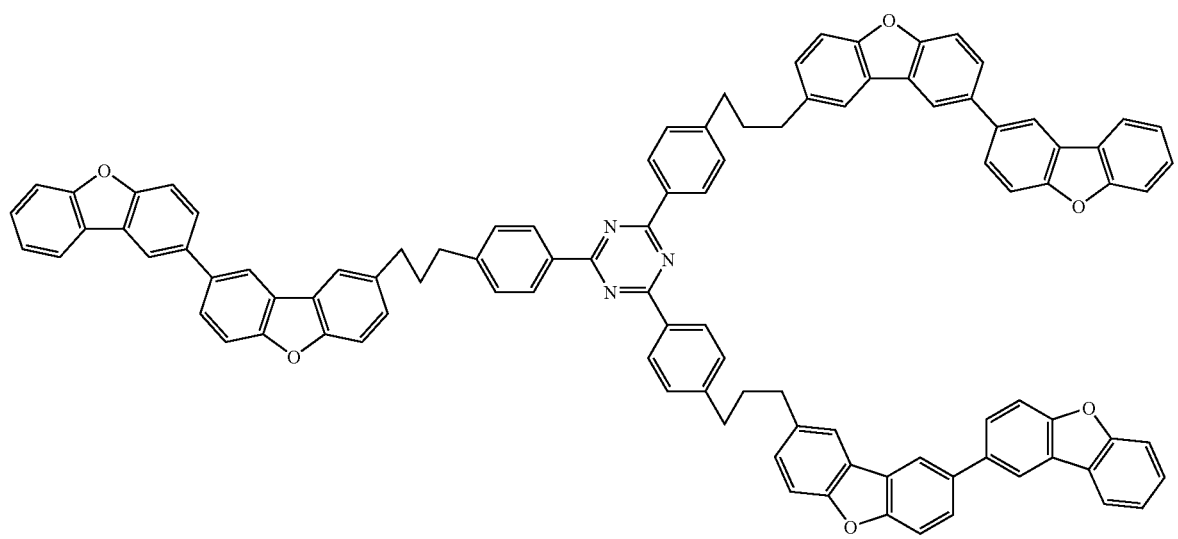
TRZ-3DBF2: Tg = 122° C., $E_T$ = 2.86 eV
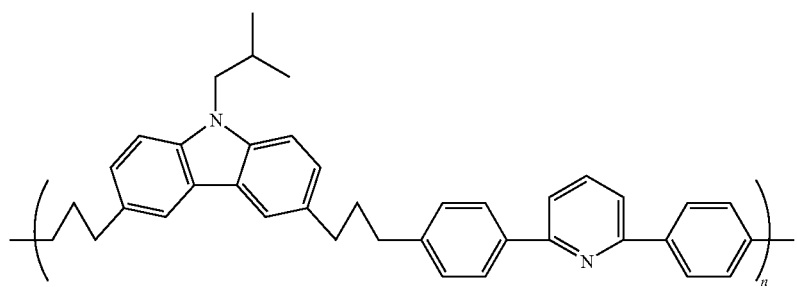
Polymer 1: $M_w$ = 80.1K, $M_n$ = 21.9K
Tg = 137° C., $E_T$ = 2.78 eV -continued
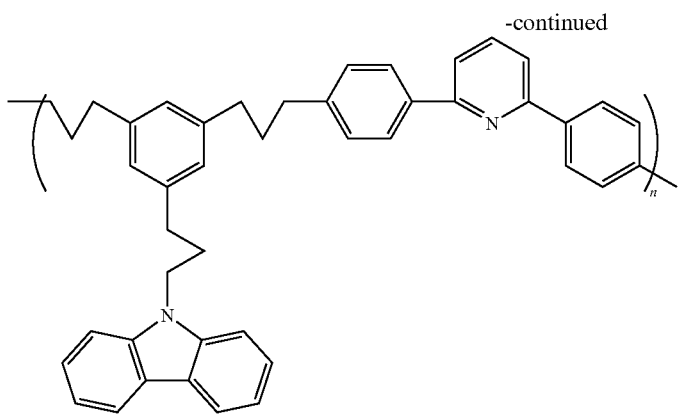
Polymer 2: $M_w = 26.8K$, $M_n = 8.41K$
$T_g = 94°$ C., $E_T = 2.78$ eV
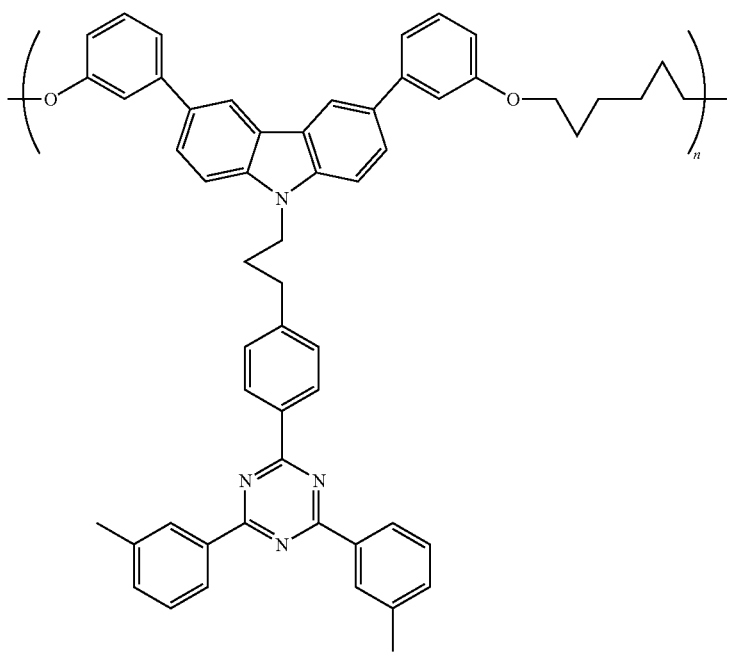
Polymer 3: $M_w = 38.3K$, $M_n = 11.9K$
$T_g = 137°$ C., $E_T = 2.81$ eV -continued
C-1
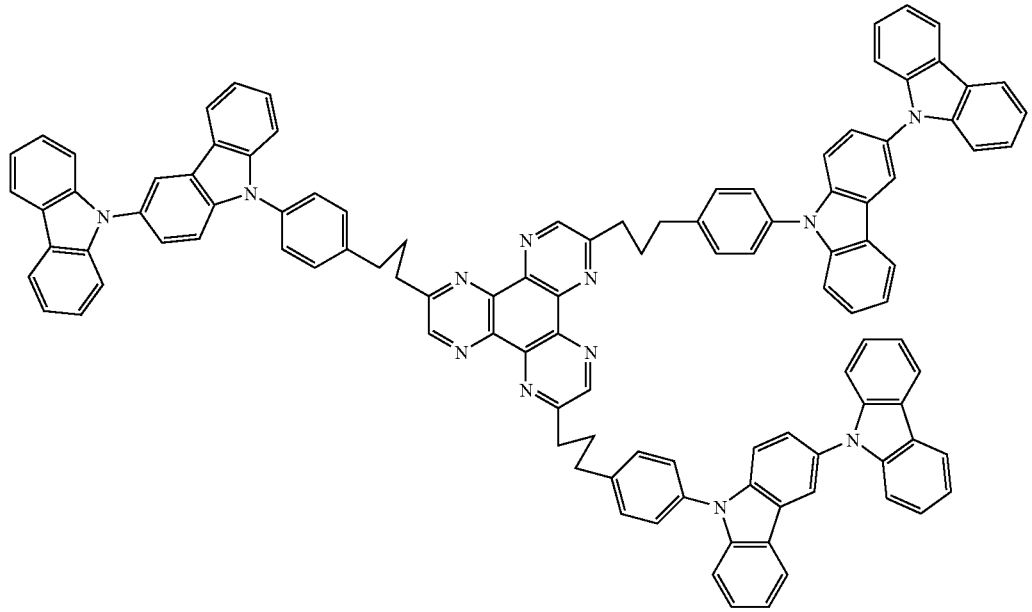
$E_T$ = 2.68 eV
C-2
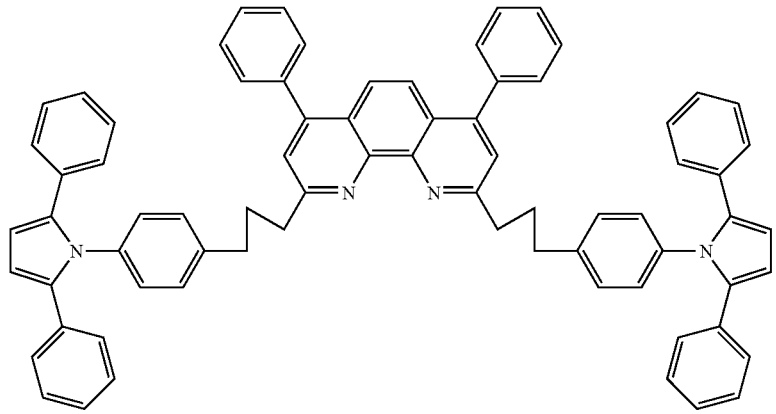
$E_T$ = 2.59 eV C-3
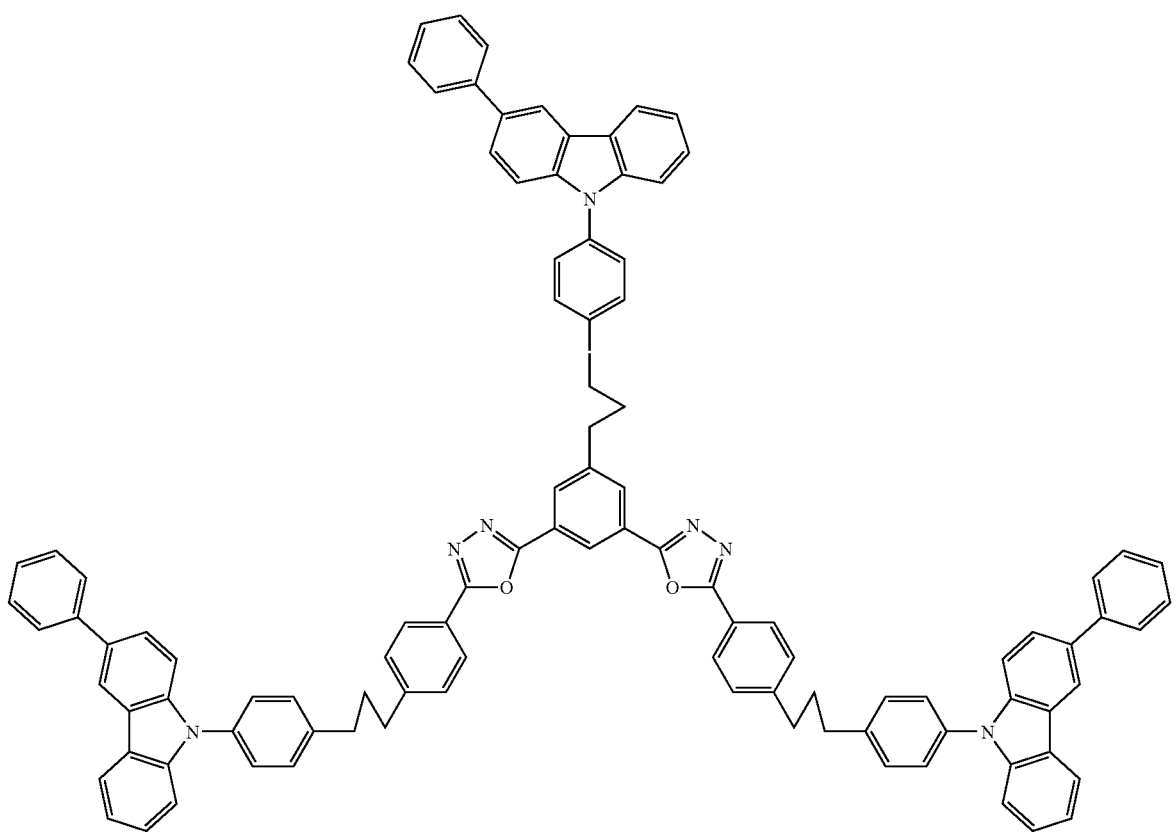
$E_T = 2.69$ eV
C-4
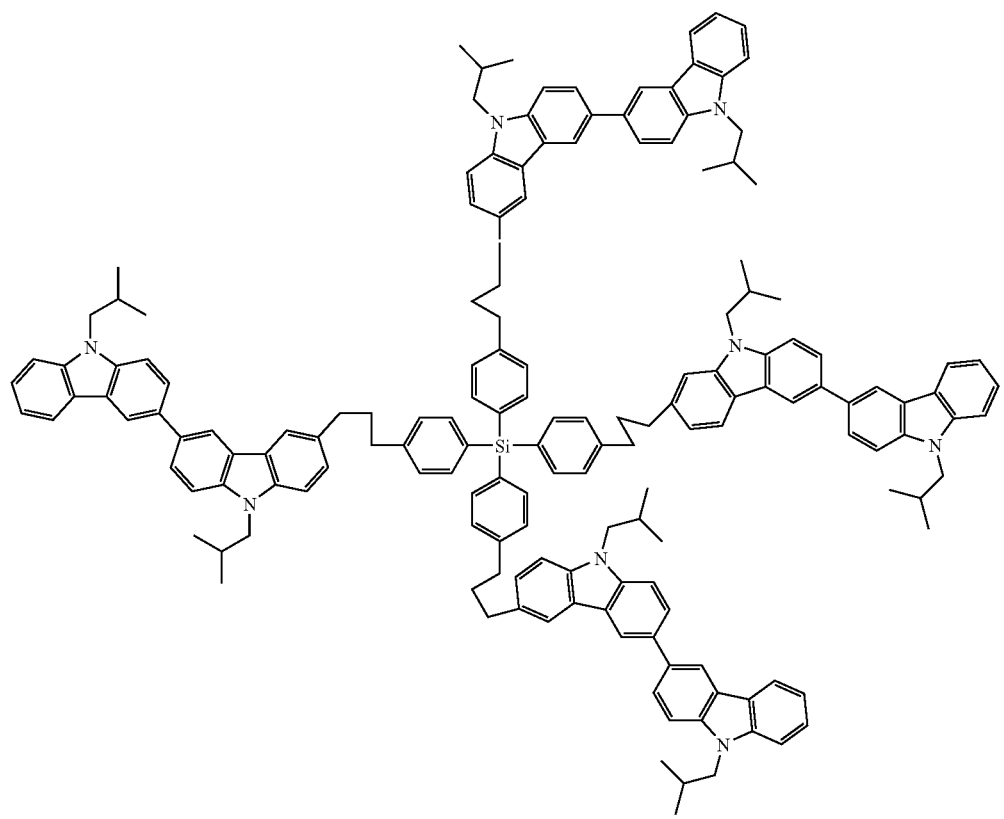
$E_T = 2.76$ eV C-5
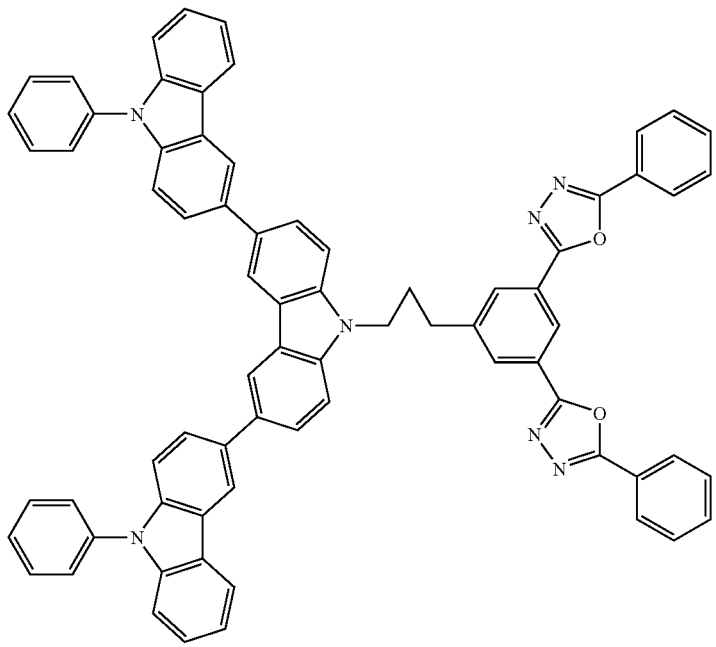
$E_T$ = 2.69 eV
C-6
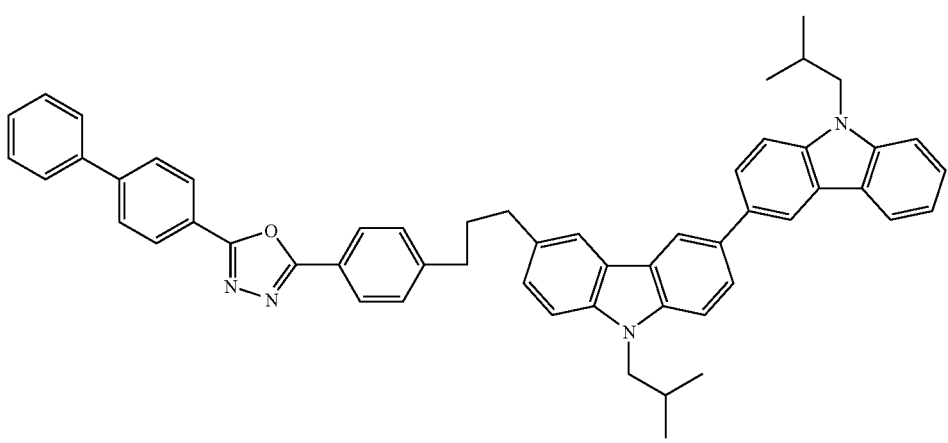
$E_T$ = 2.54 eV
C-7        C-8
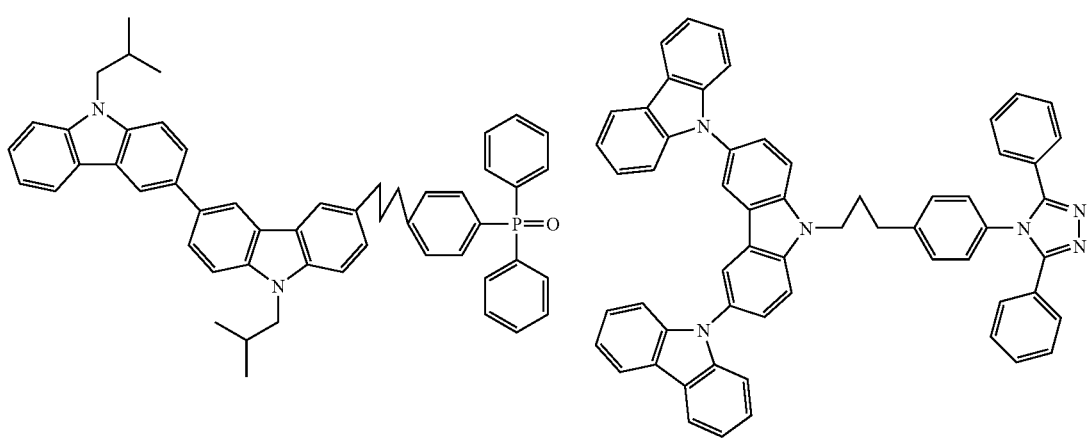
$E_T$ = 2.76 eV        $E_T$ = 2.94 eV -continued
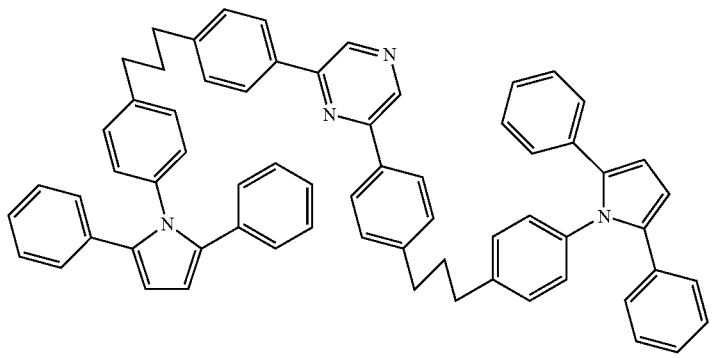
C-9
$E_T$ = 2.65 eV
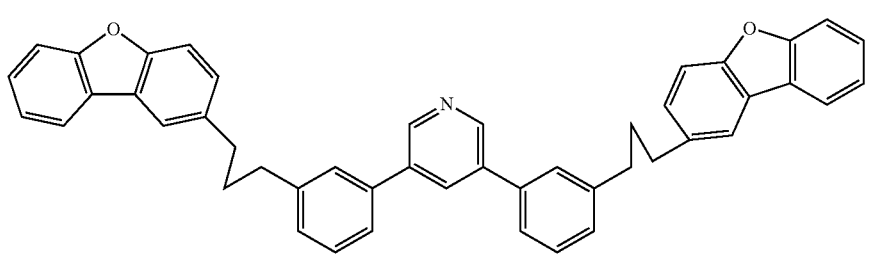
C-10
$E_T$ = 2.95 eV
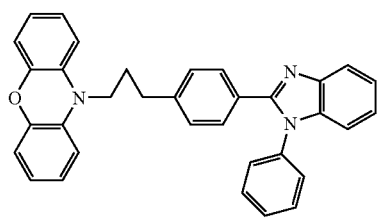
C-11
$E_T$ = 2.57 eV
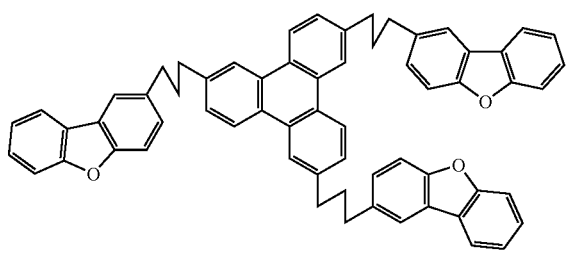
C-12
$E_T$ = 2.95 eV
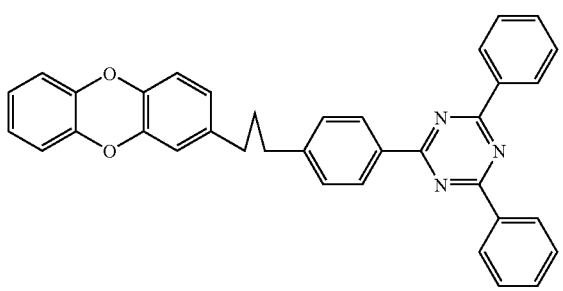
C-13
$E_T$ = 2.94 eV
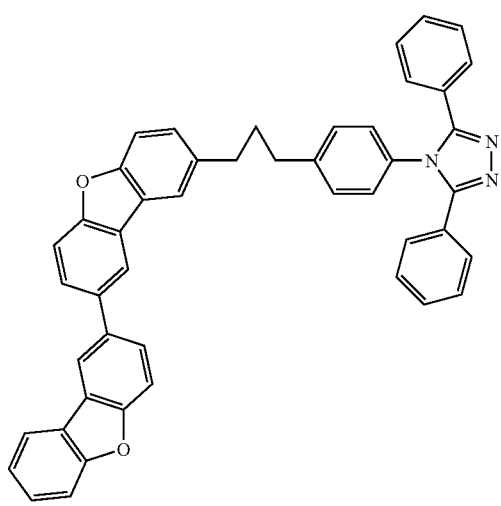
C-14
$E_T$ = 2.86 eV C-15
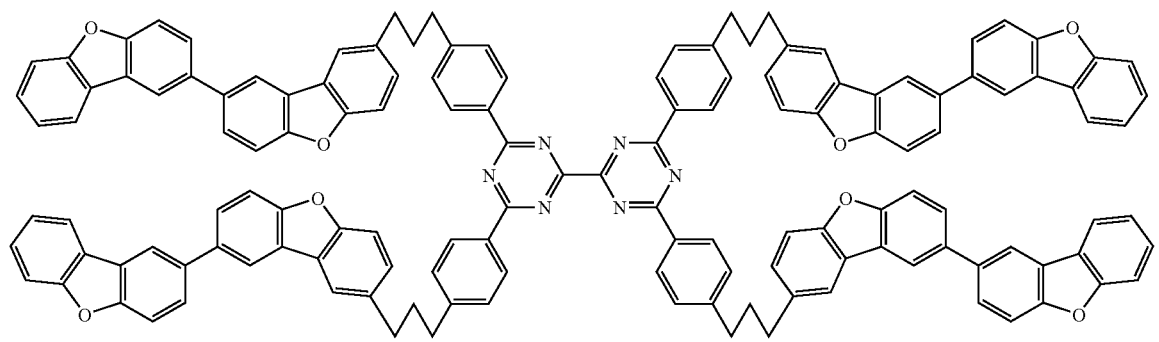
$E_T = 2.74$ eV
C-16
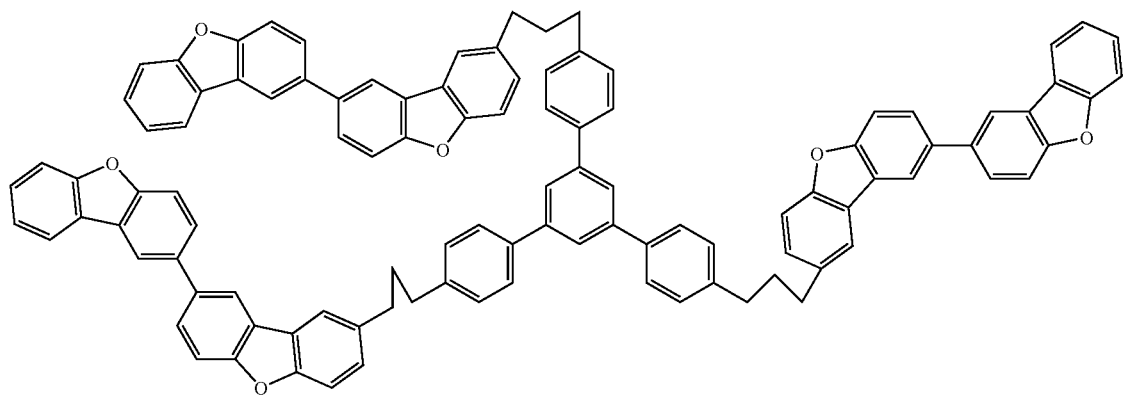
$E_T = 2.76$ eV
C-17
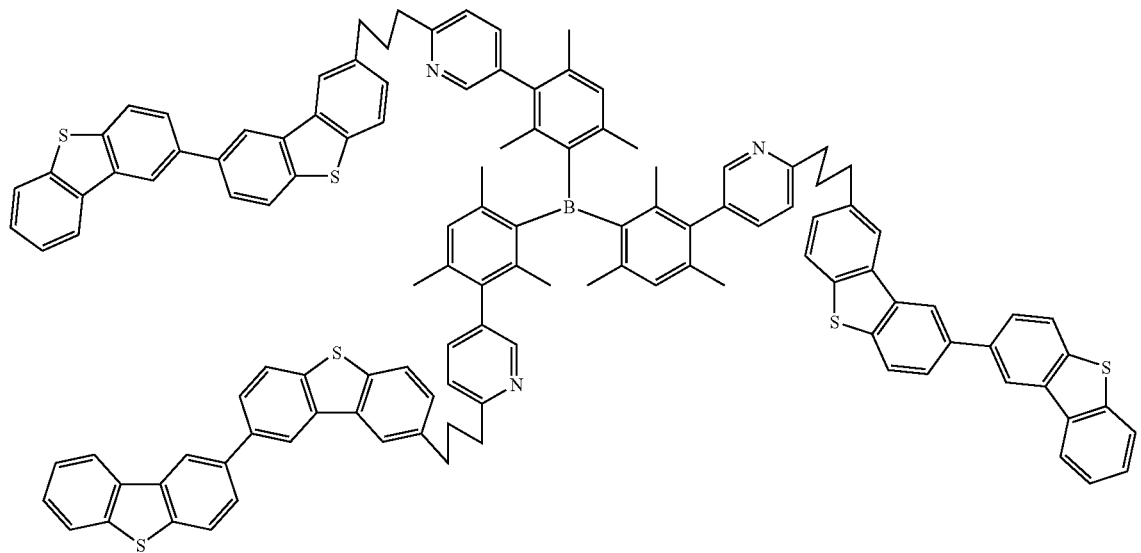
$E_T = 2.75$ eV -continued
C-18
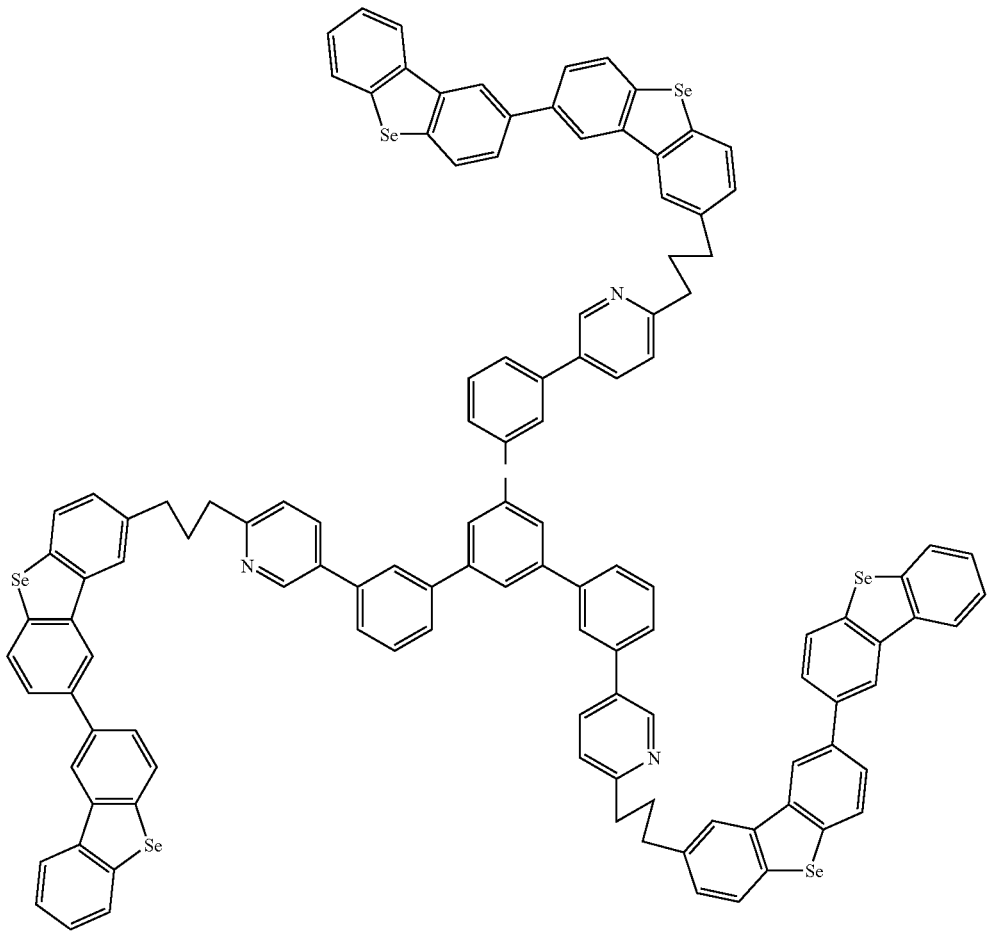
$E_T = 2.78$ eV
C-19
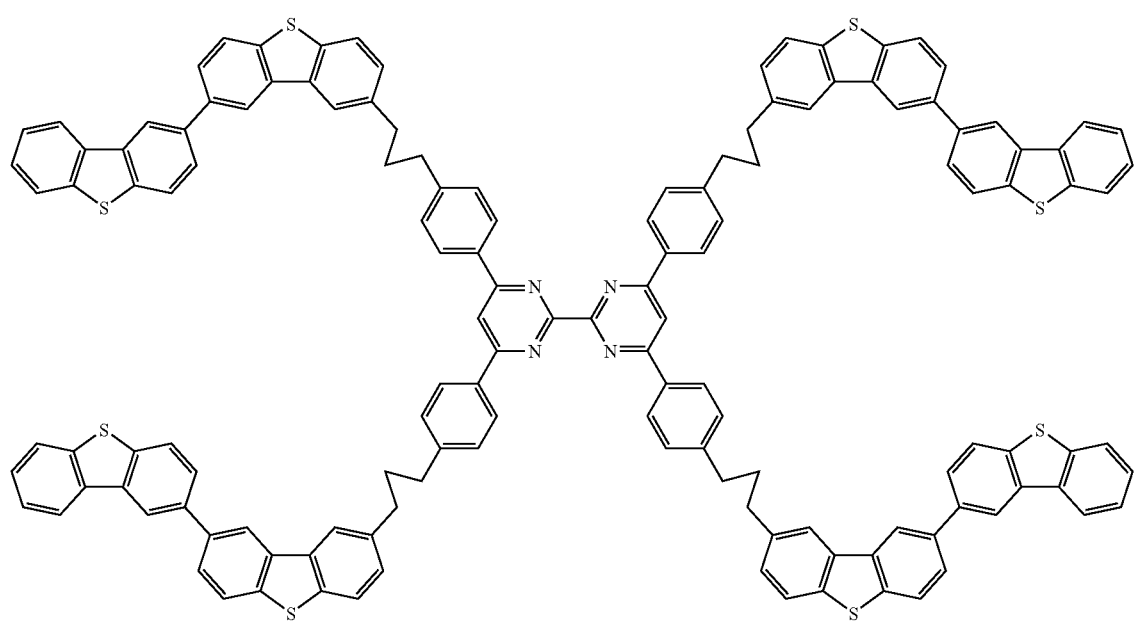
$E_T = 2.70$ eV -continued
C-20
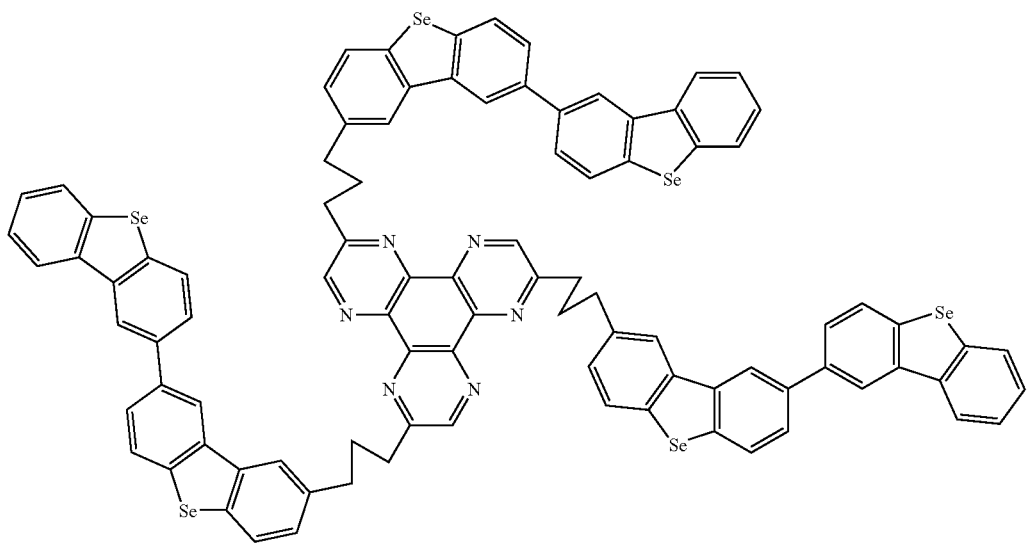
$E_T = 2.68$ eV
C-21
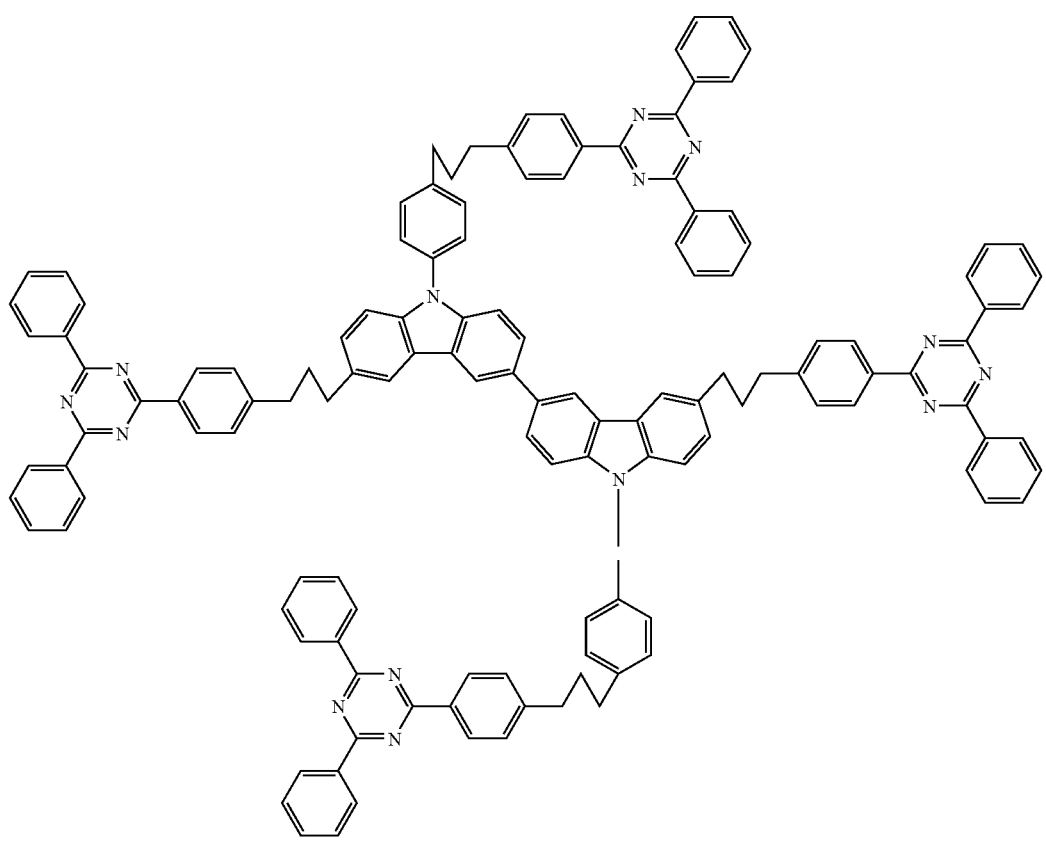
$E_T = 2.76$ eV -continued
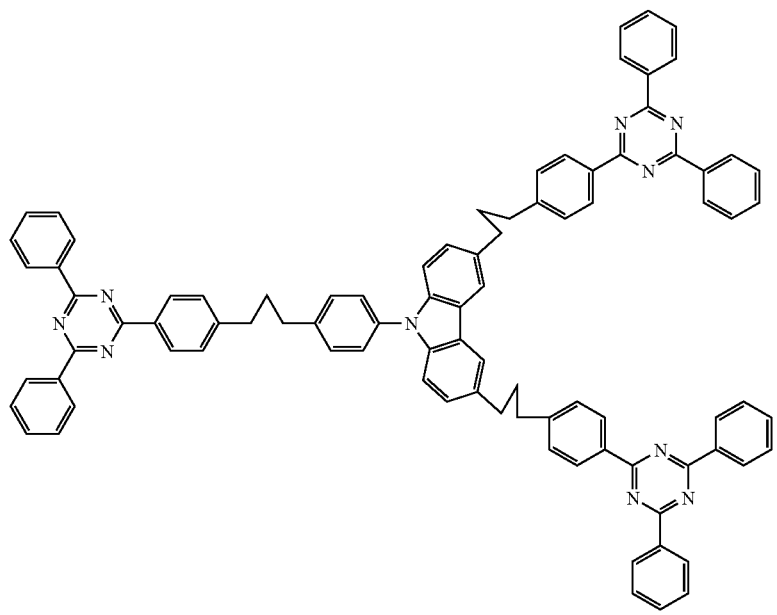
C-22
$E_T = 3.04$ eV
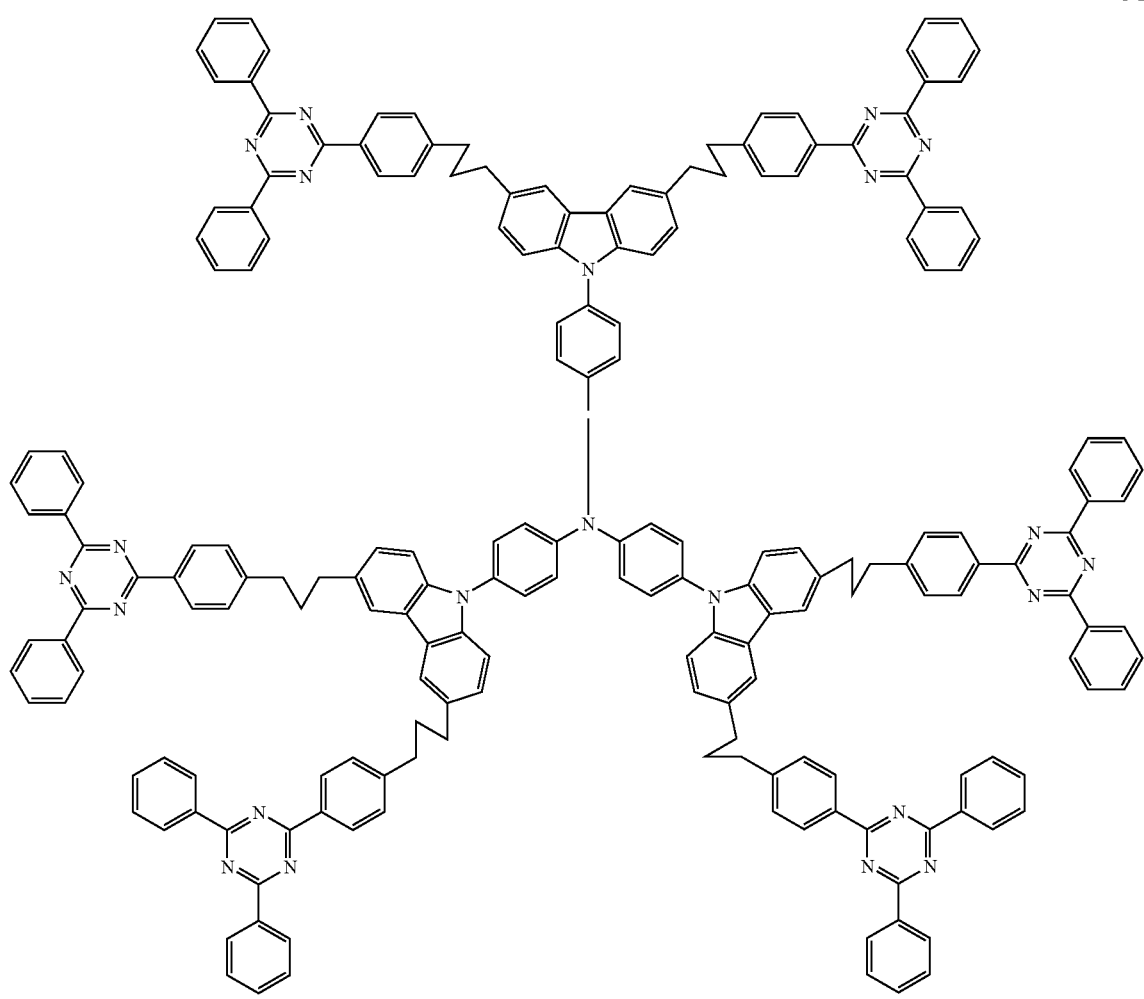
C-23
$E_T = 2.86$ eV -continued
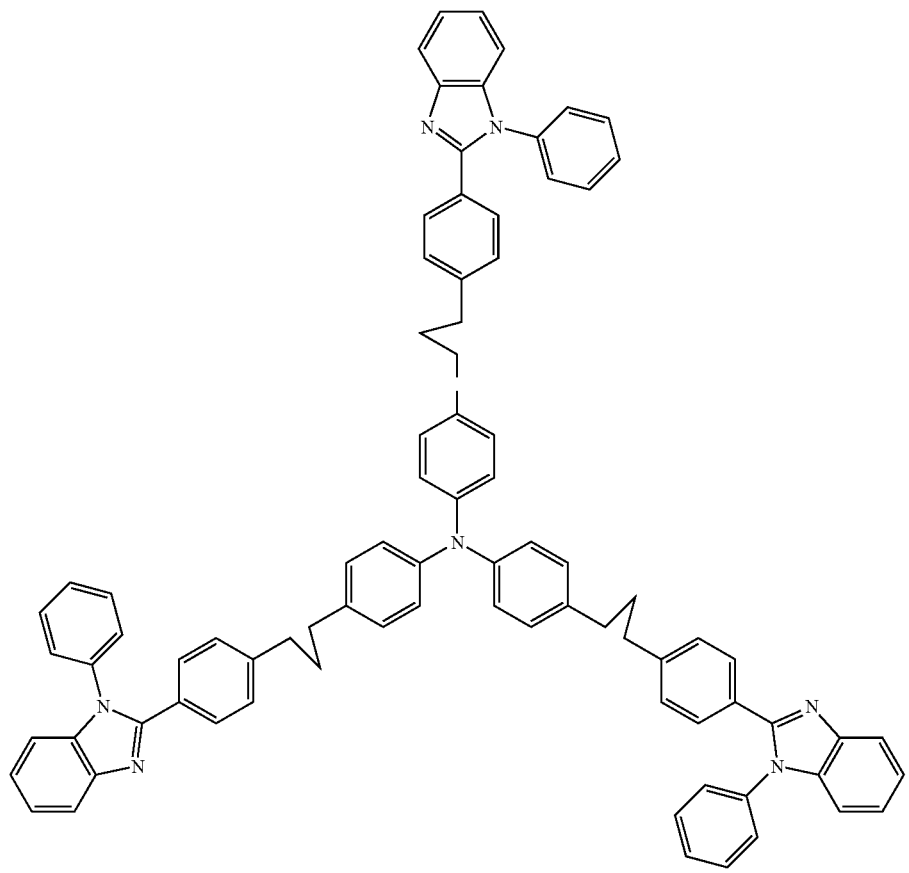
$E_T$ = 2.79 eV
C-24
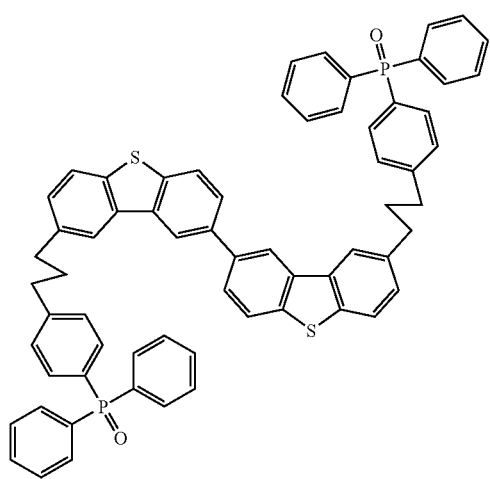
$E_T$ = 2.76 eV
C-25
$E_T$ = 2.78 eV
C-26

C-27
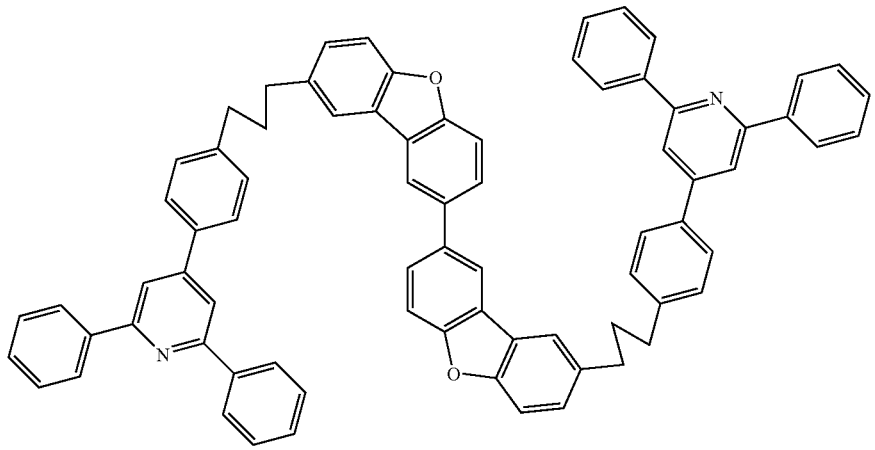
$E_T = 2.75$ eV
C-28
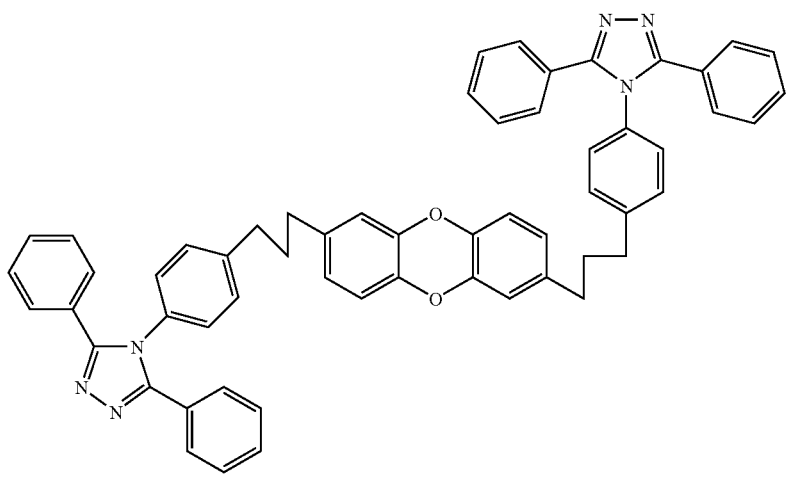
$E_T = 2.94$ eV
C-29
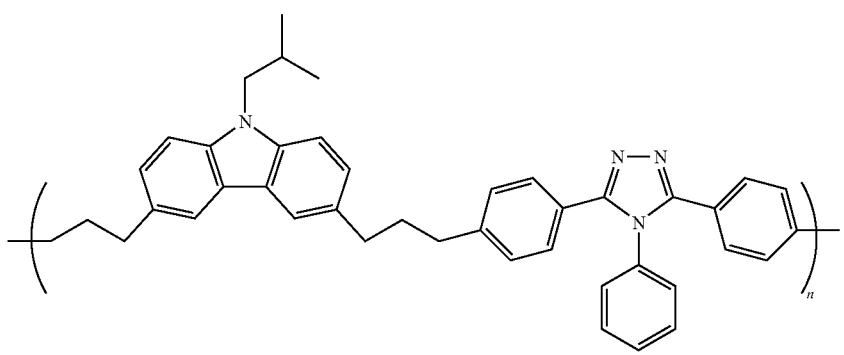
$E_T = 3.0$ eV -continued

C-30

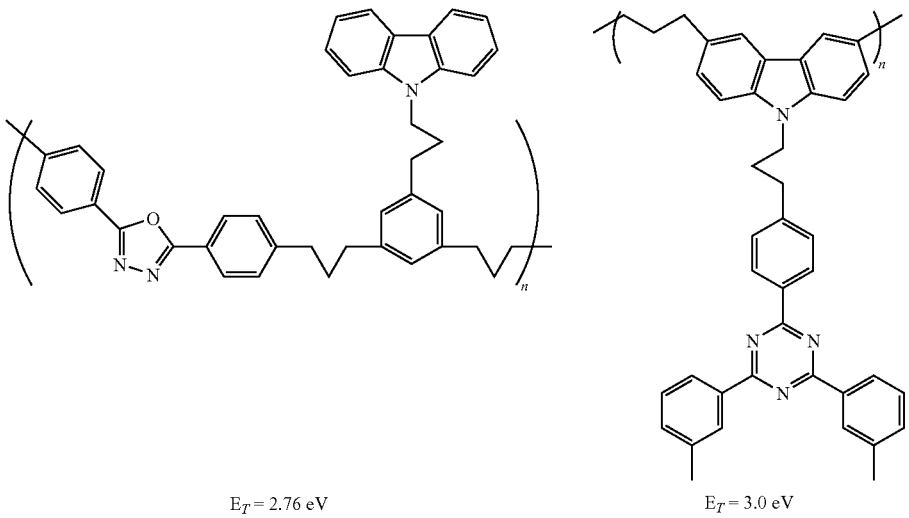

$E_T = 2.76$ eV

C-31

$E_T = 3.0$ eV

C-32

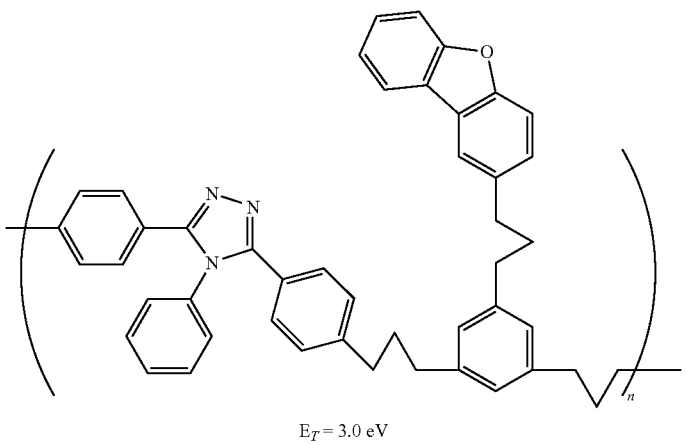

$E_T = 3.0$ eV

Figure 10:
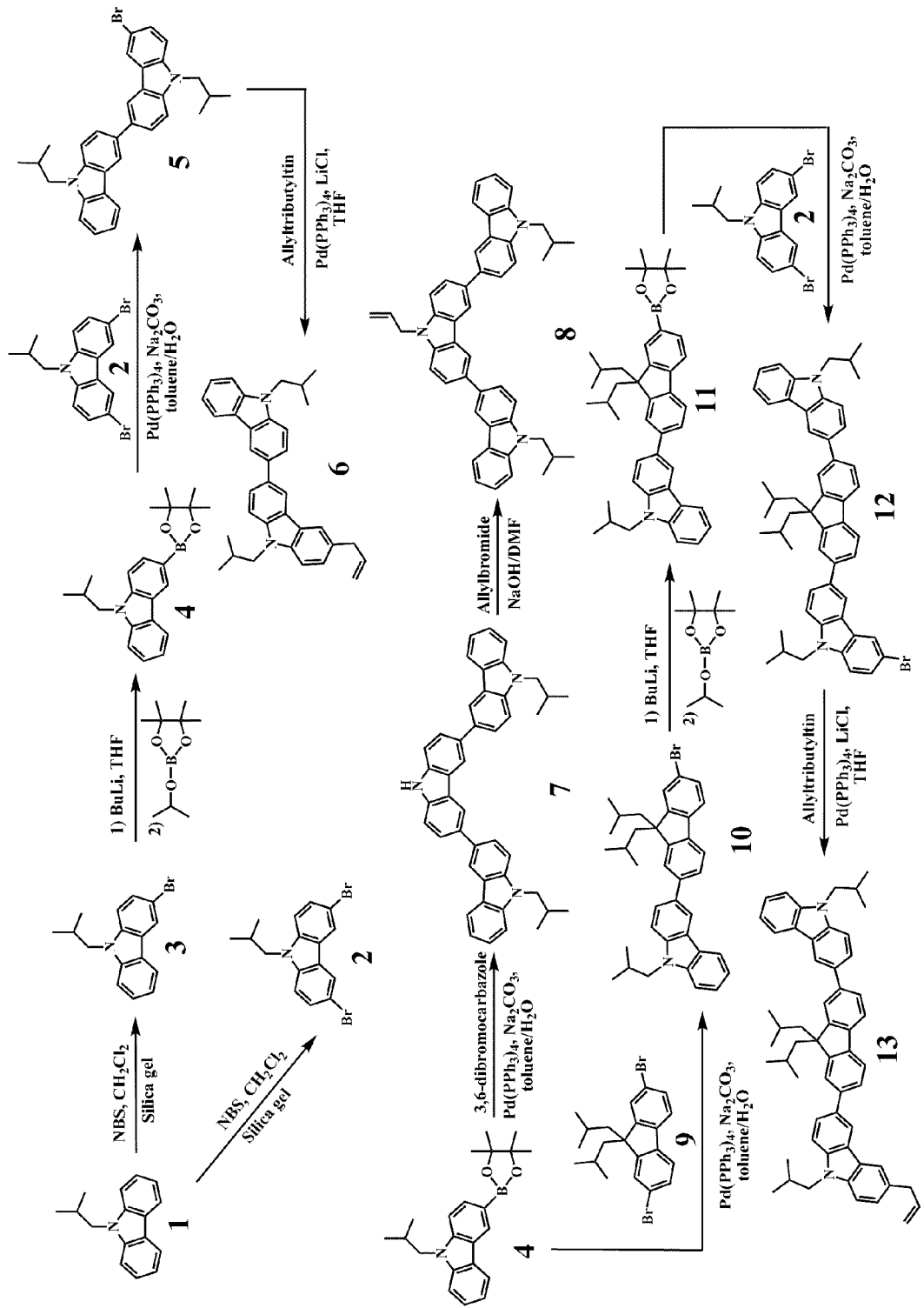
FIG. 10. Graphical depiction of reaction scheme for preparation of examples of compounds and polymers of the present invention.
Figure 10:
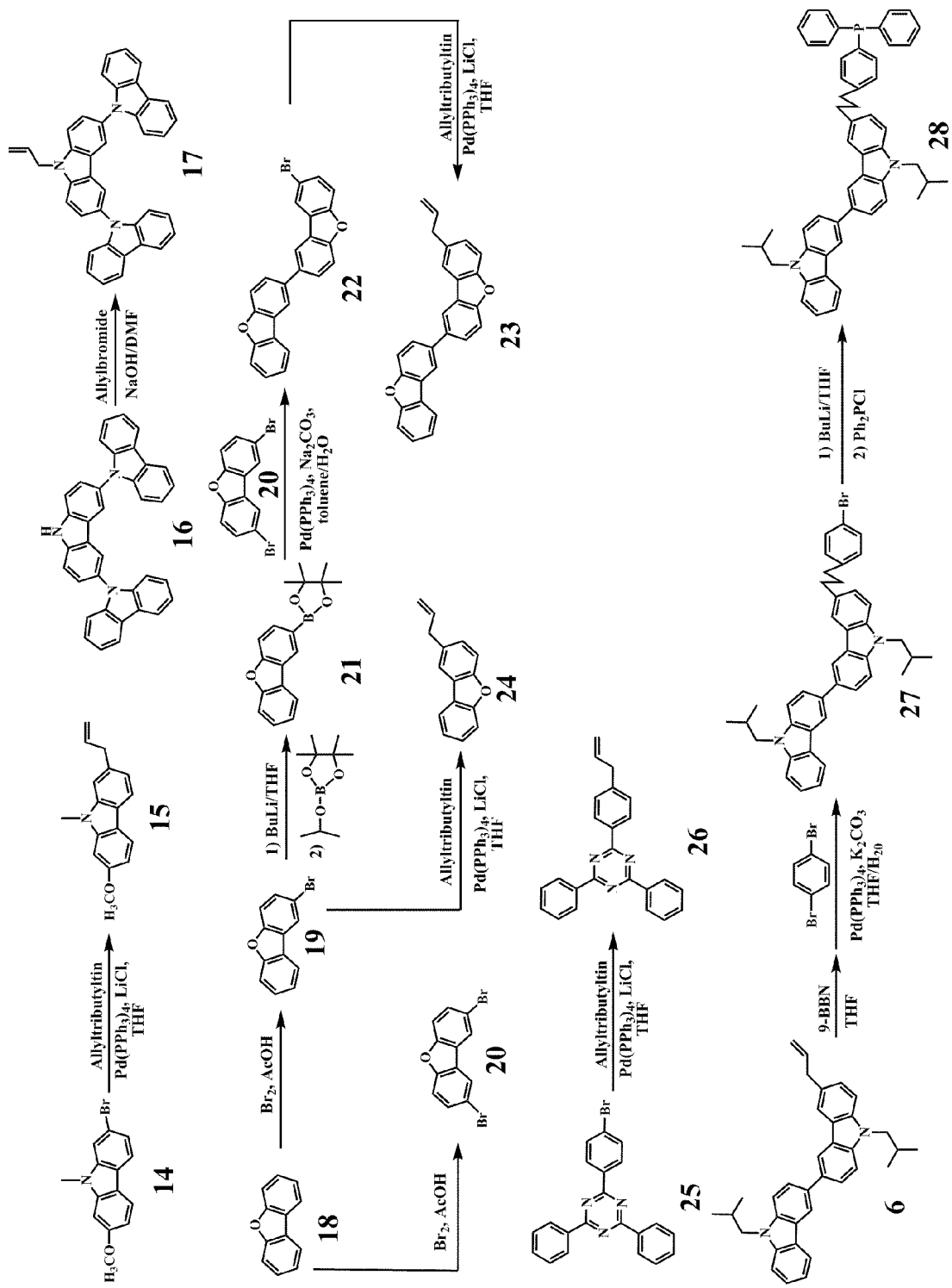
Figure 10:
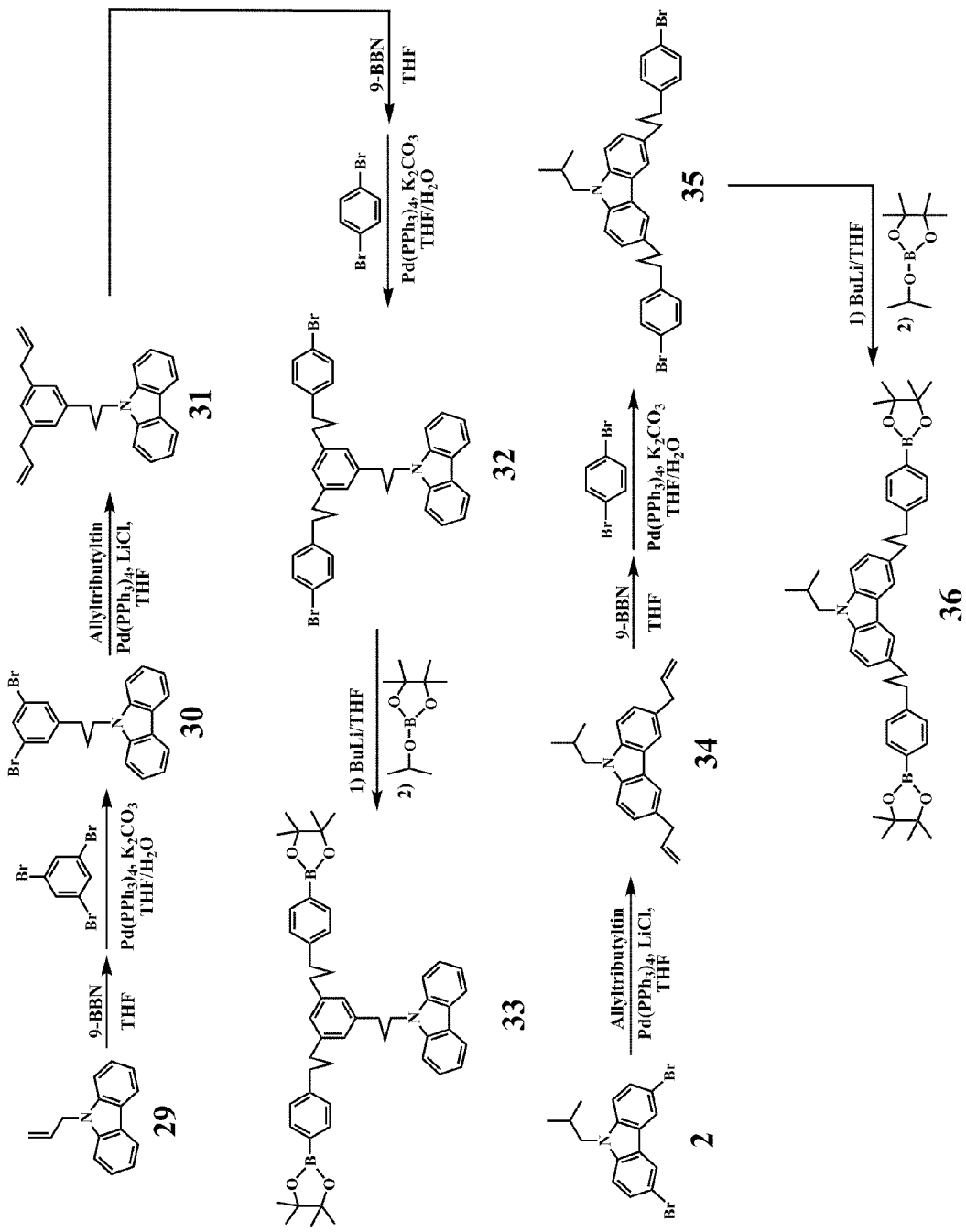
Figure 10:
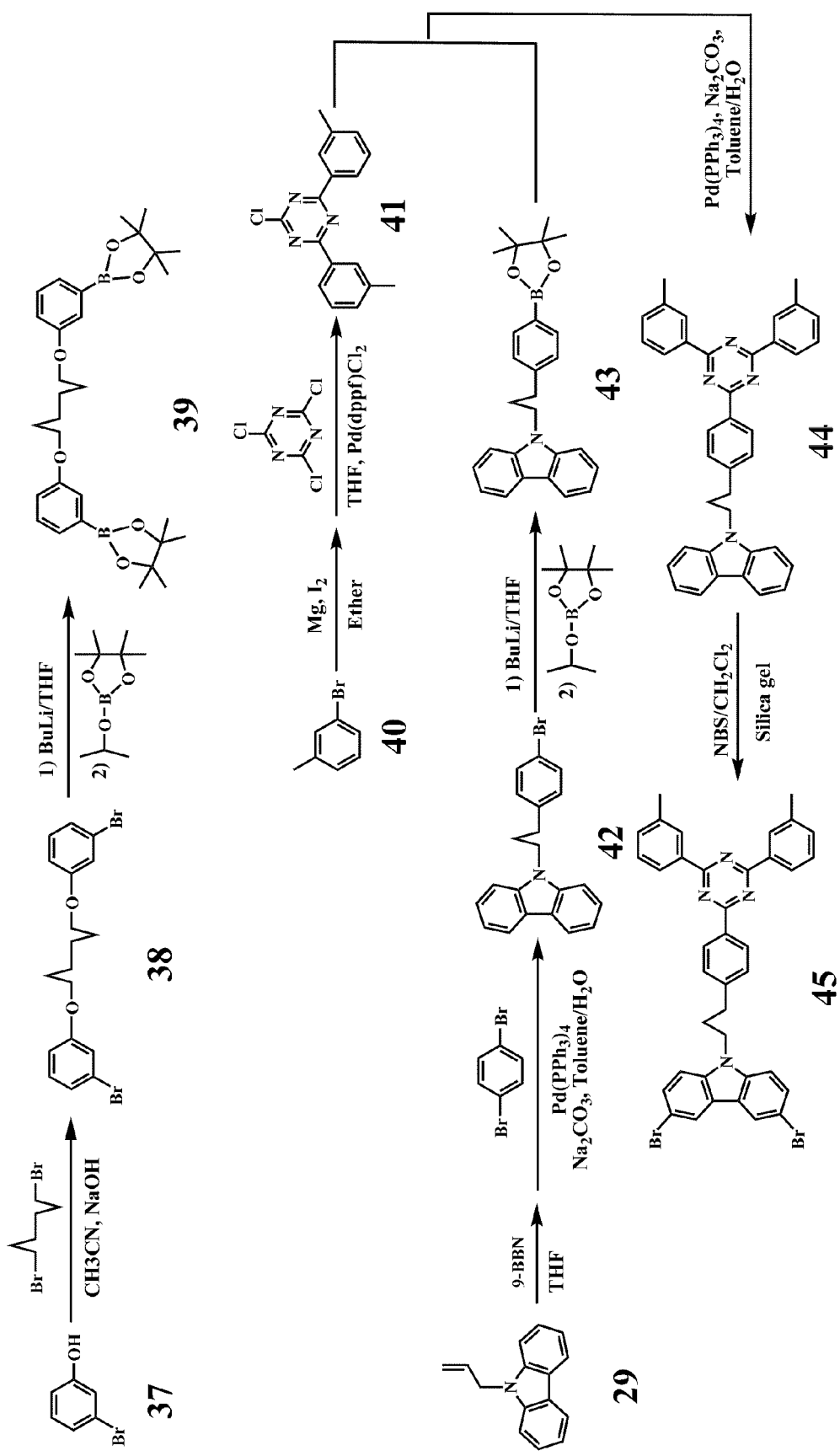
Figure 10:
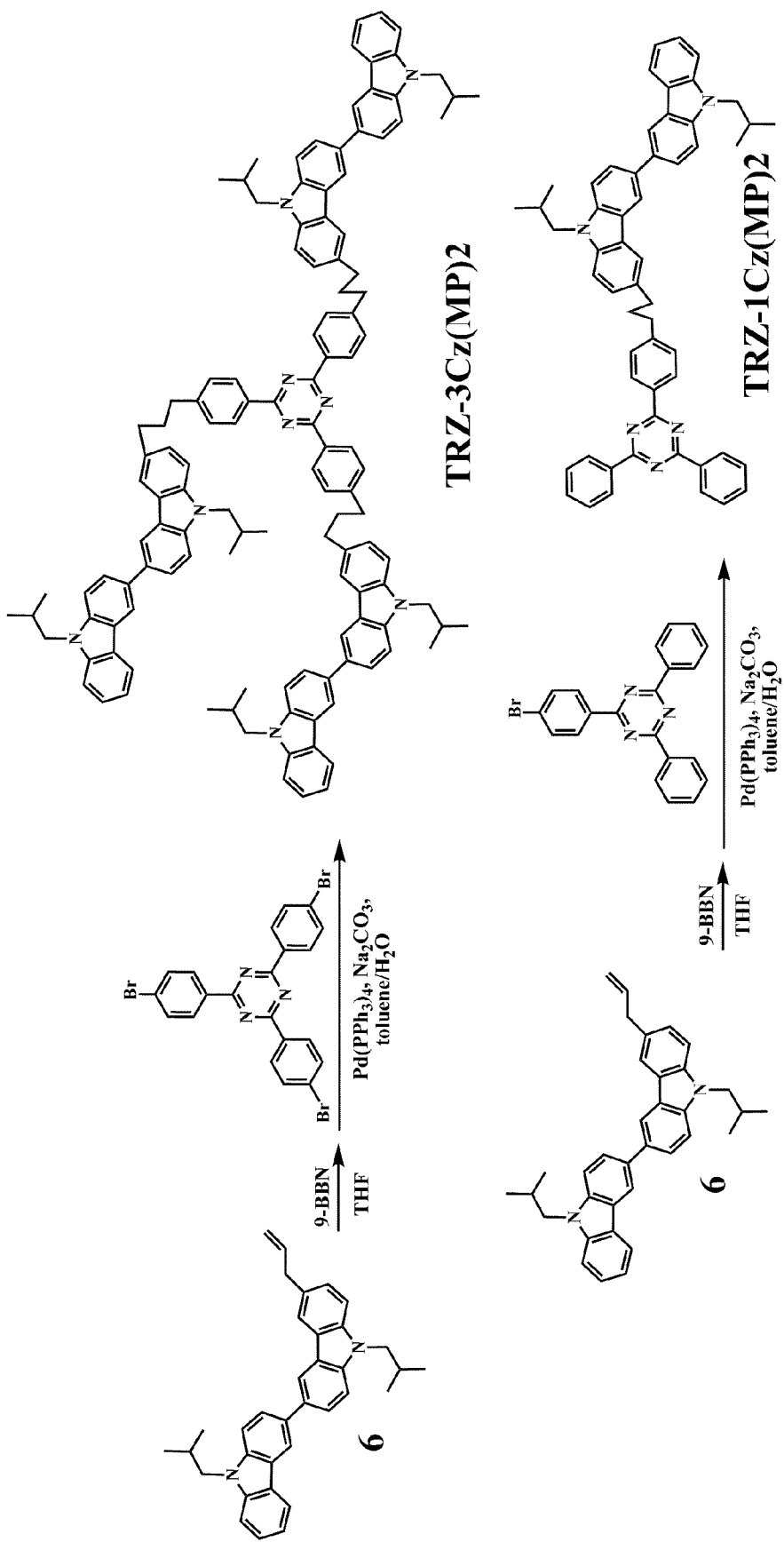
Figure 10:
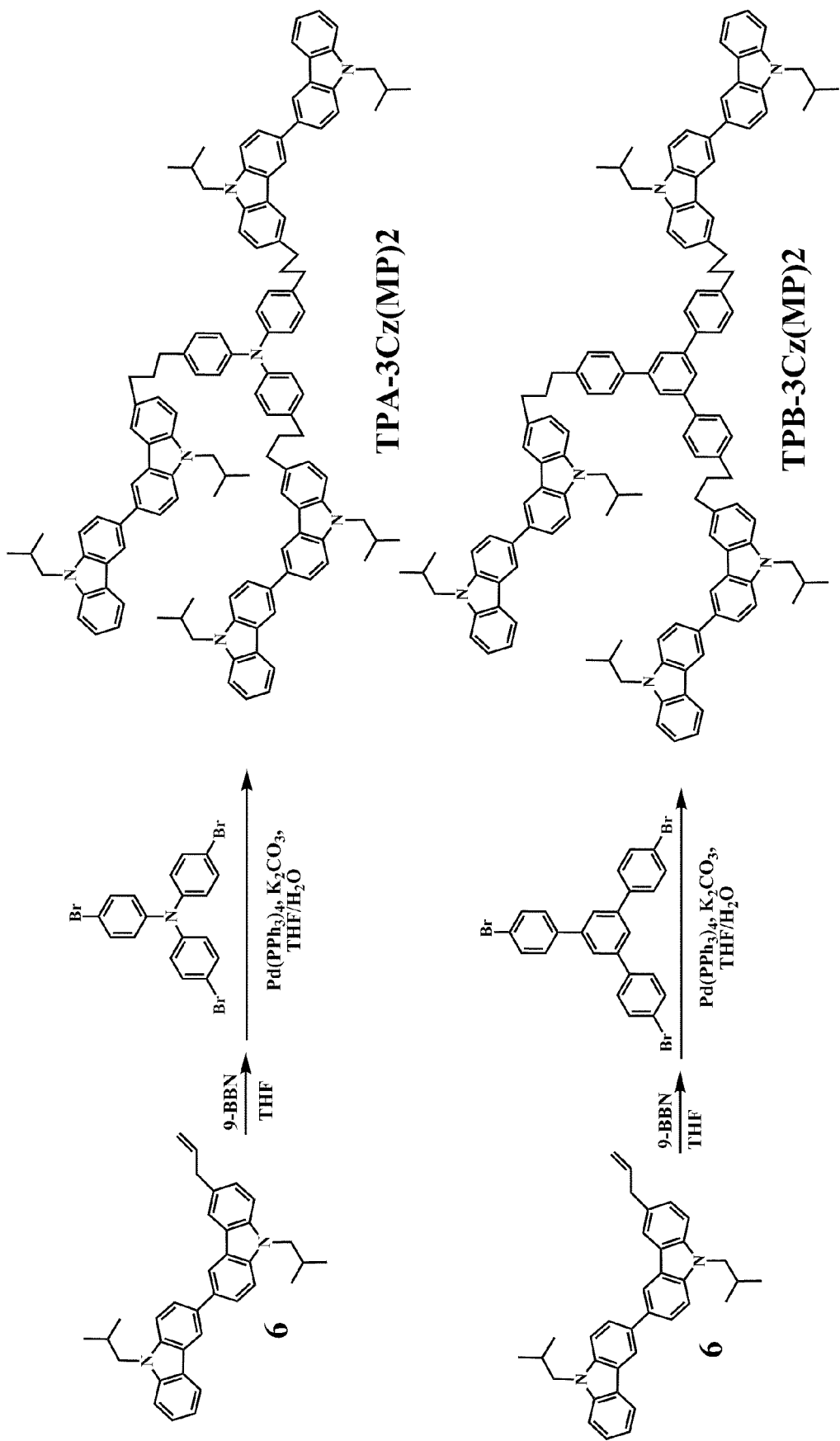
Figure 10:
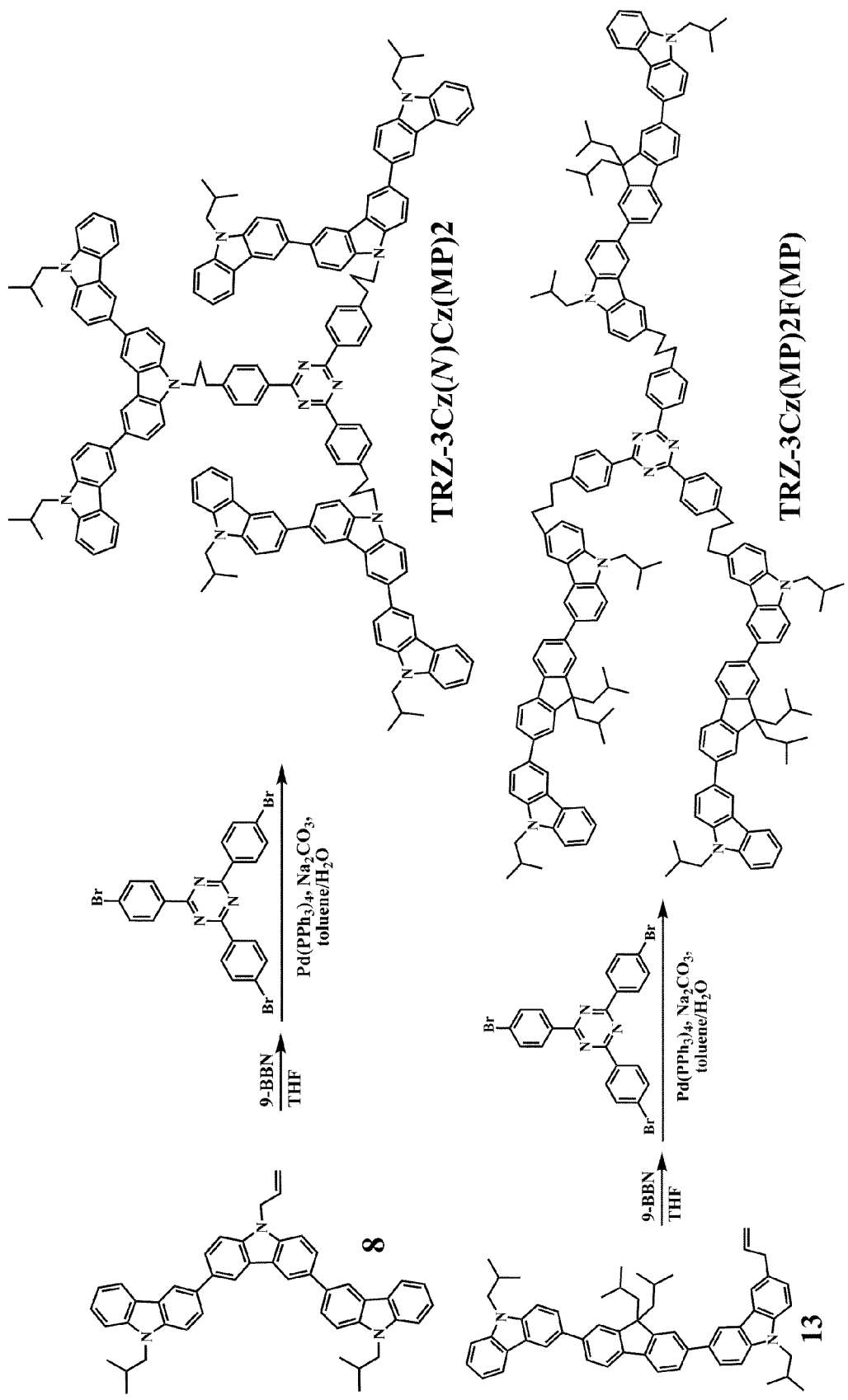
Figure 10:
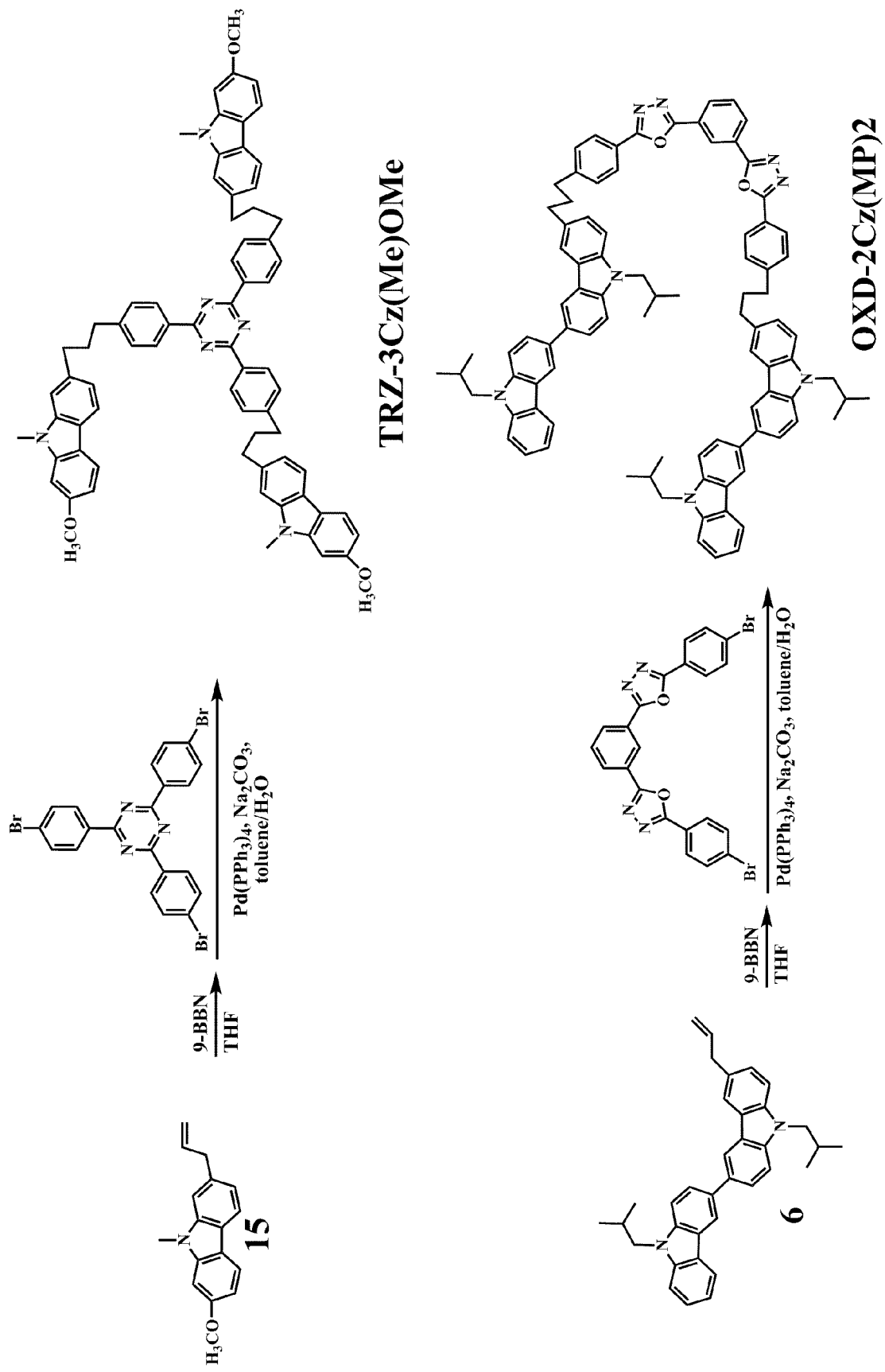
Figure 10:
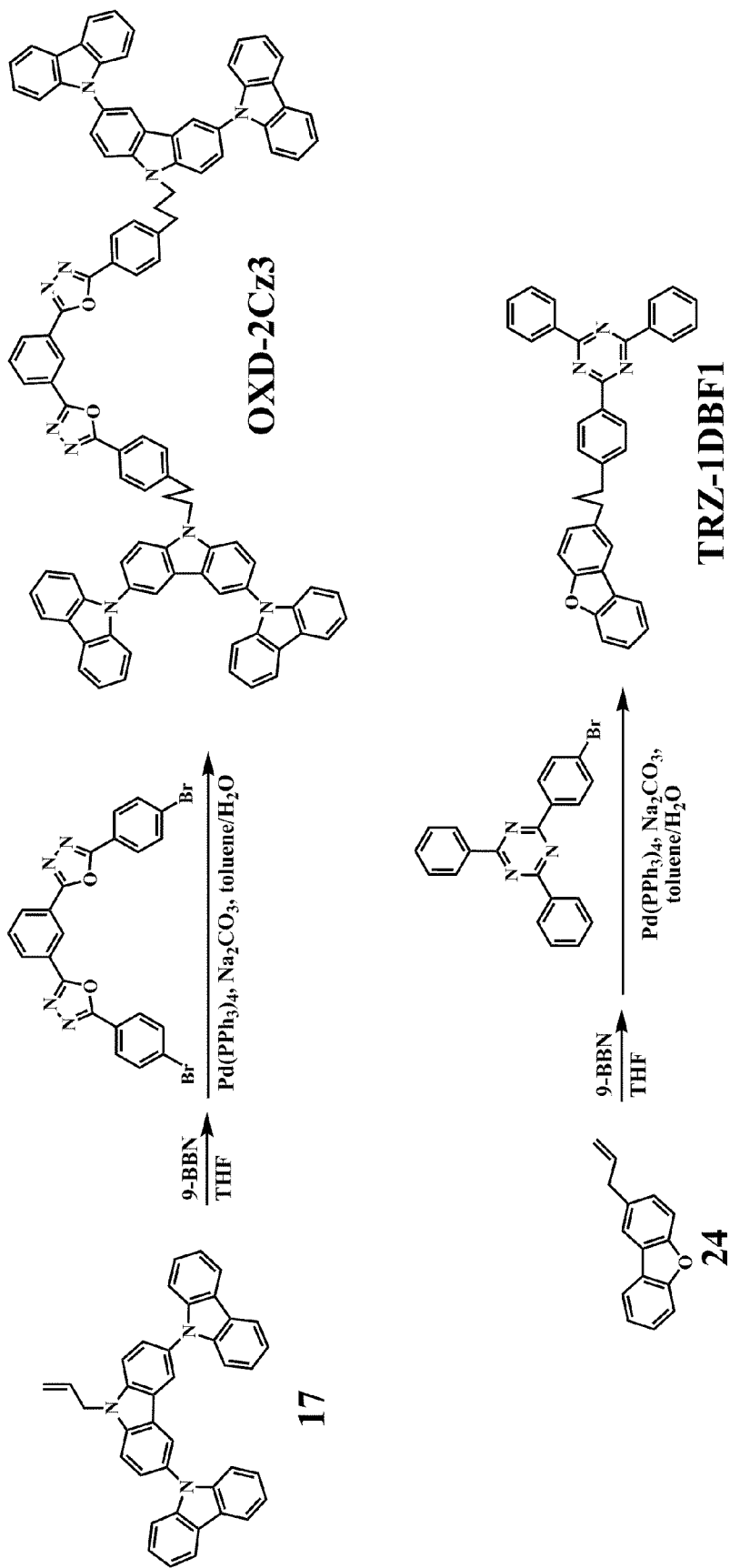
Figure 10:
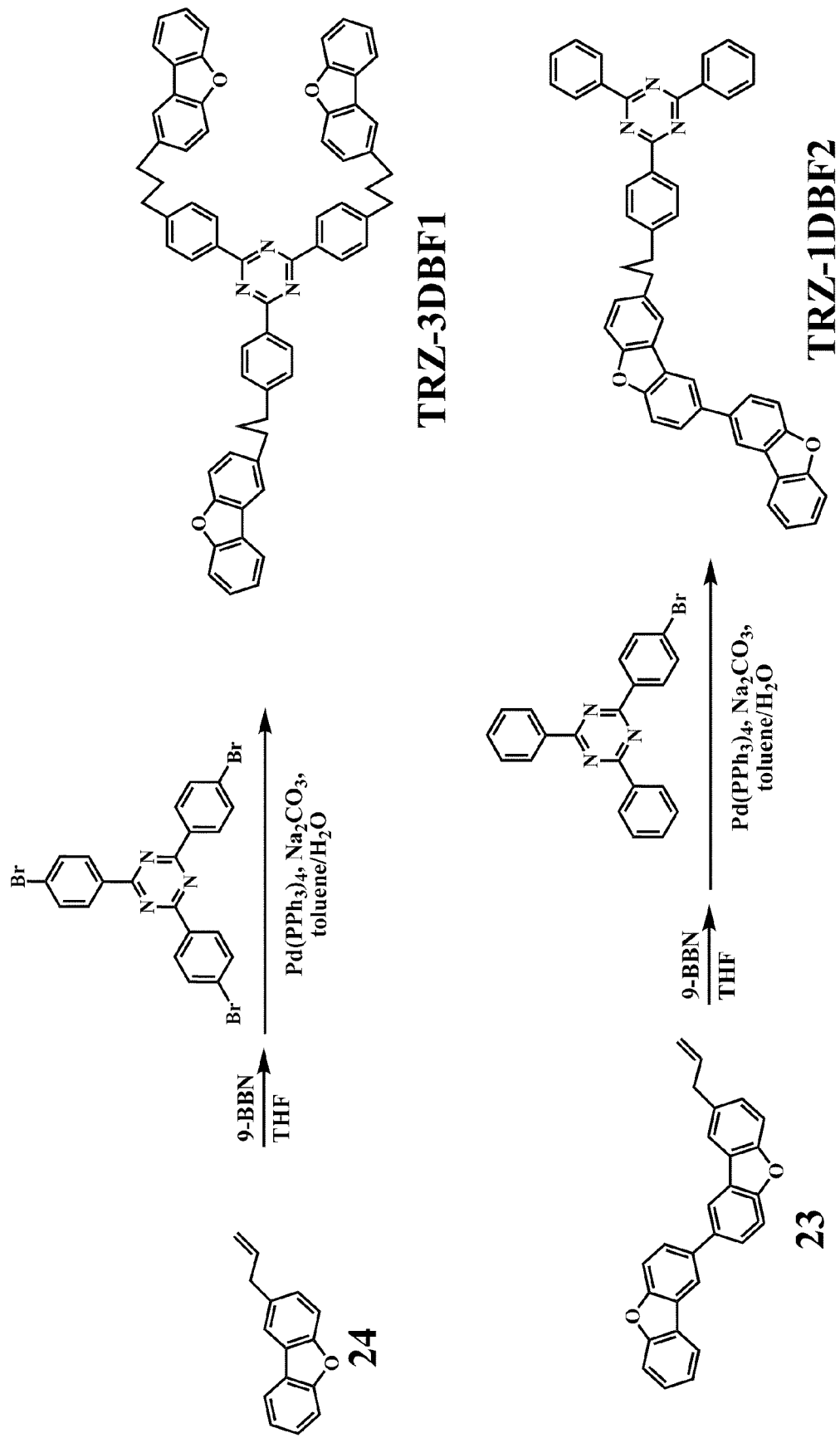
Figure 10:
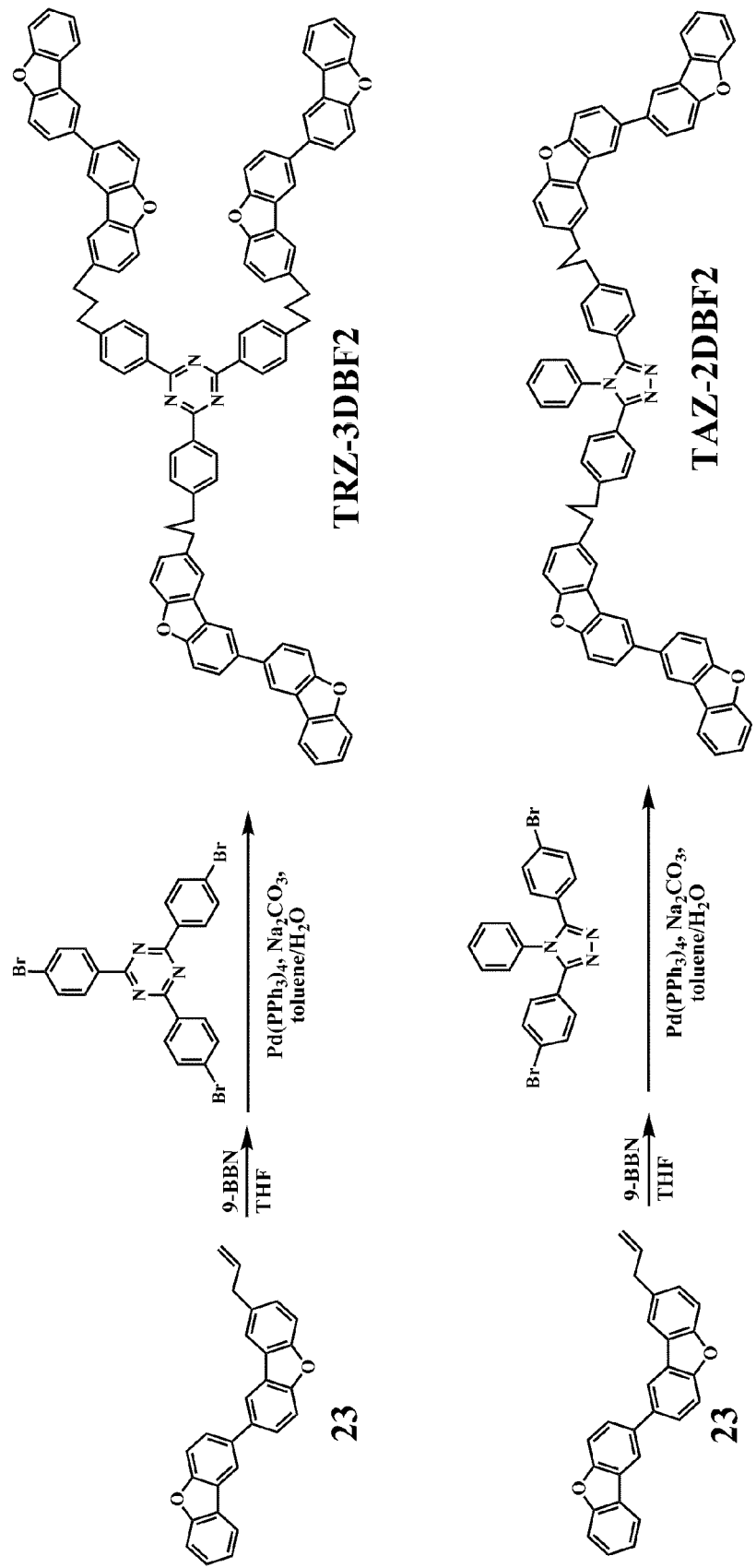
Figure 10:
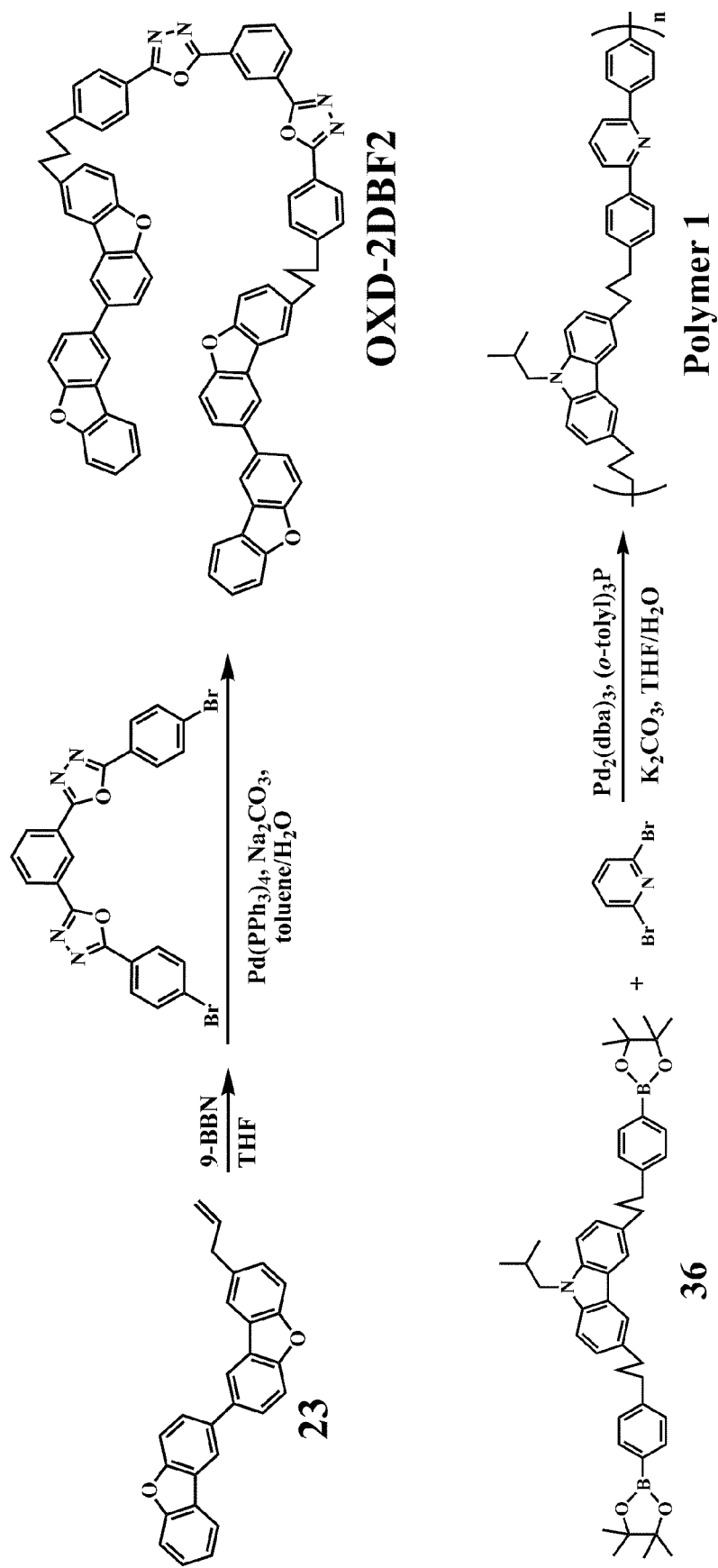
Figure 10:
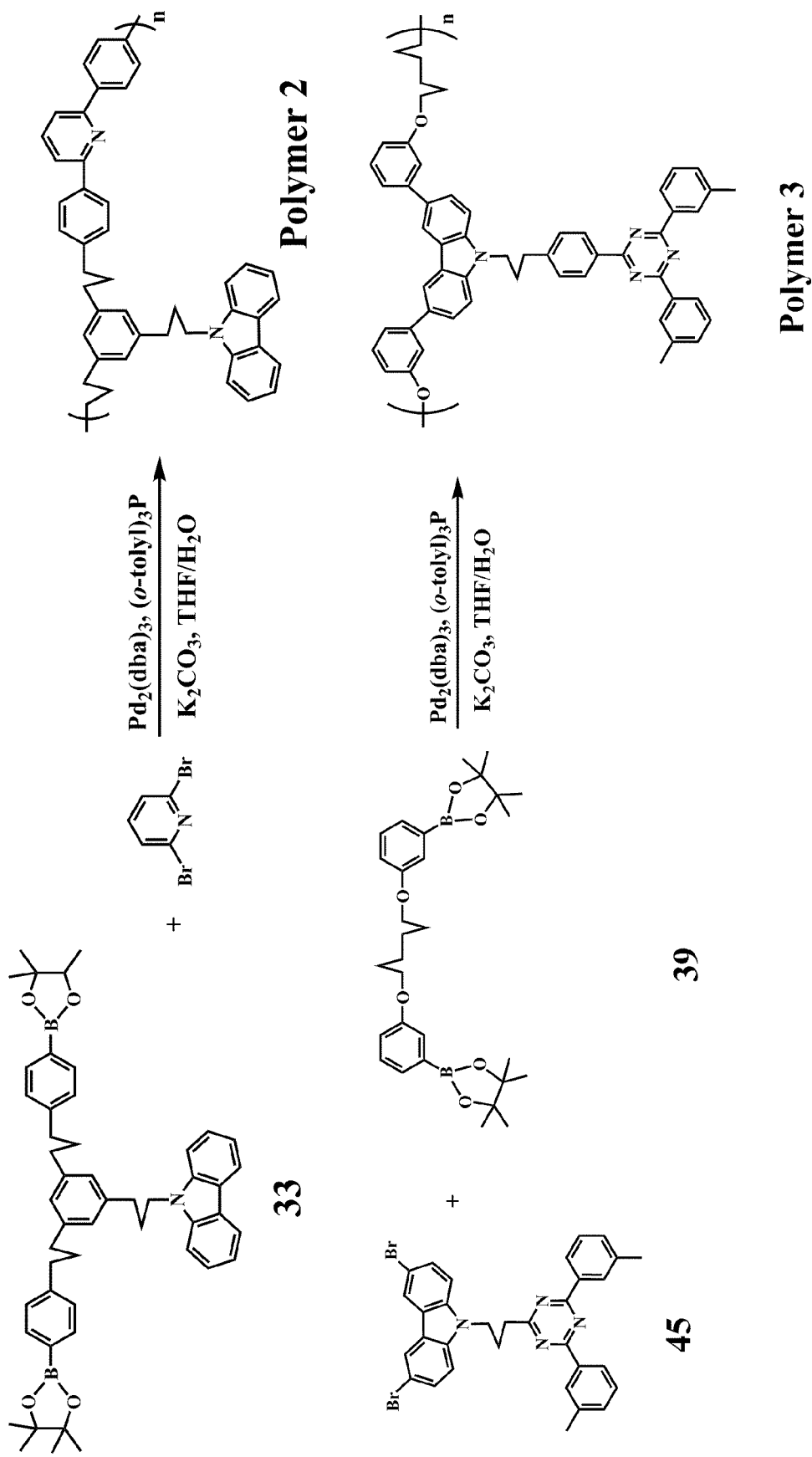
Figure 10:
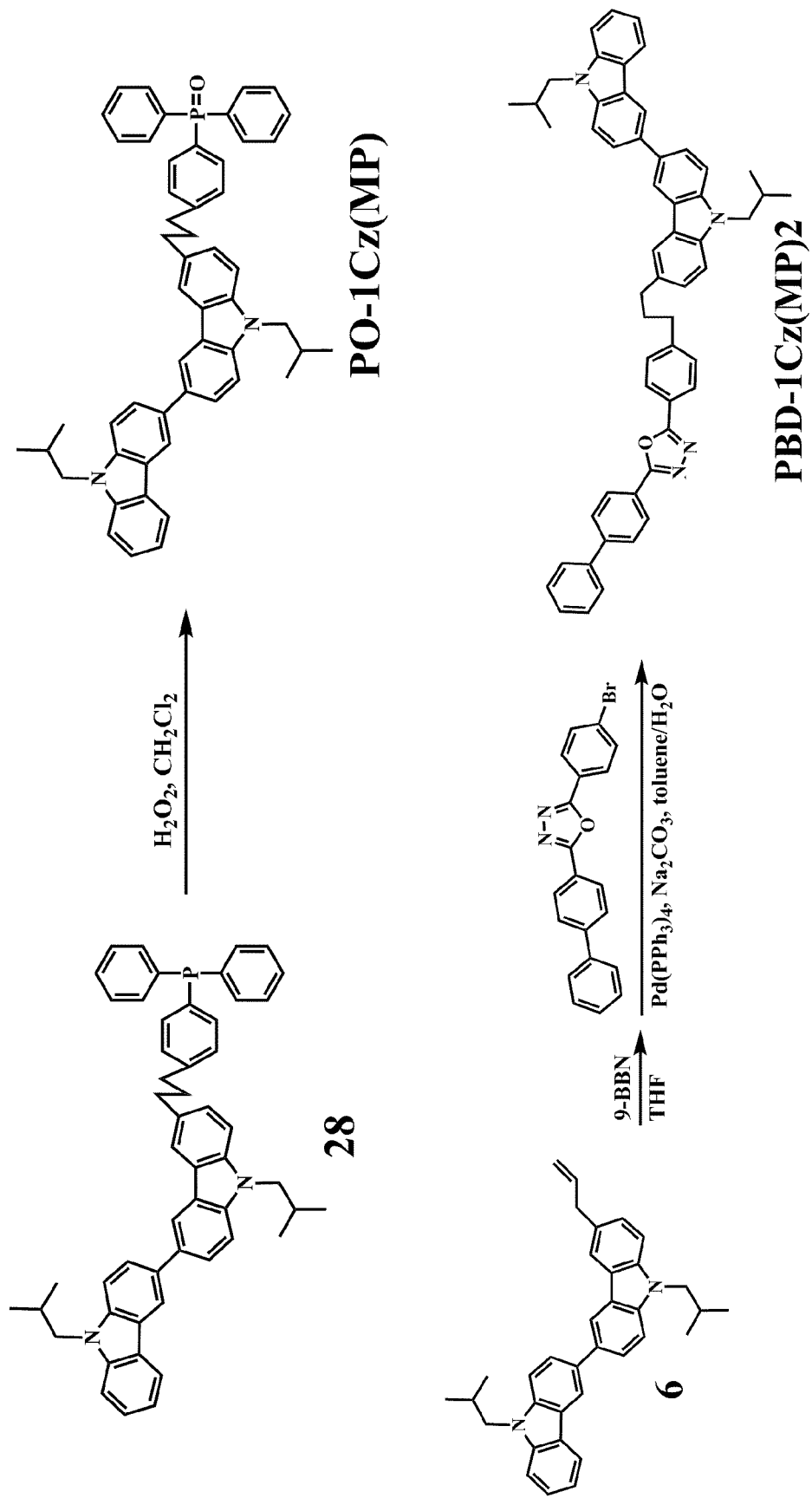
Figure 10:
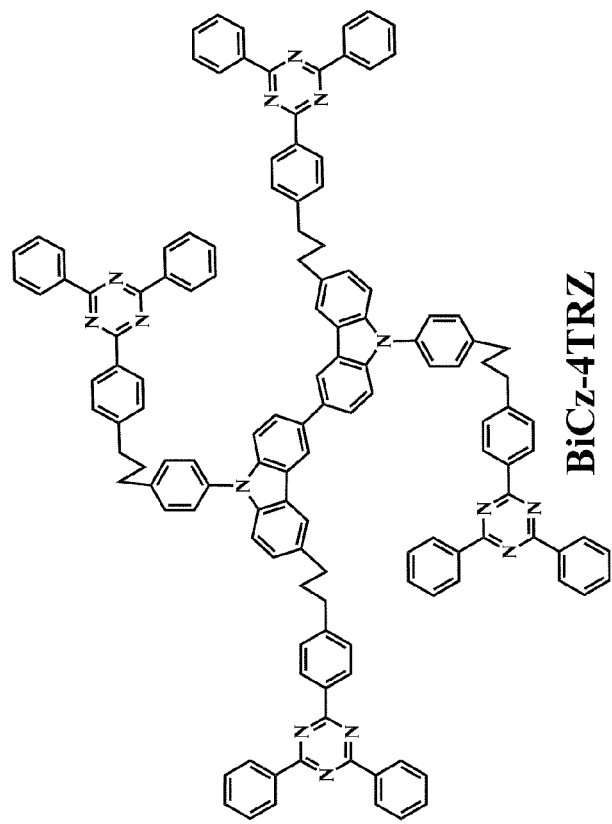
Figure 10:
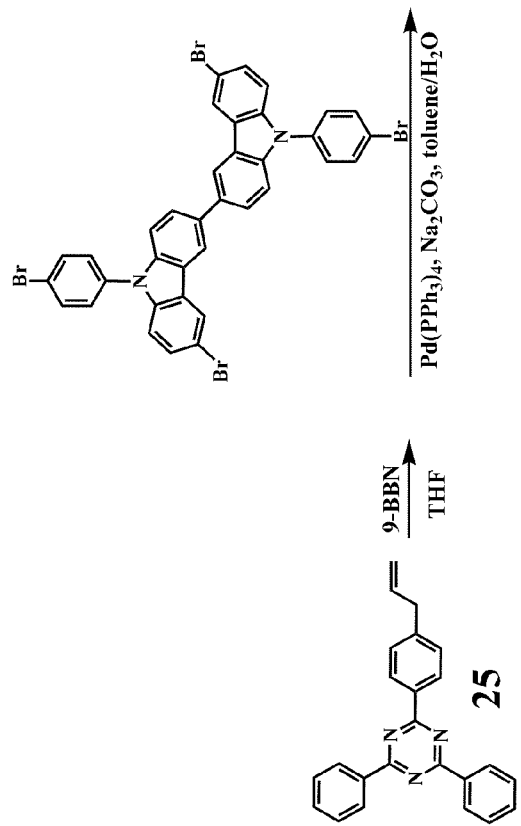
Figure 10:
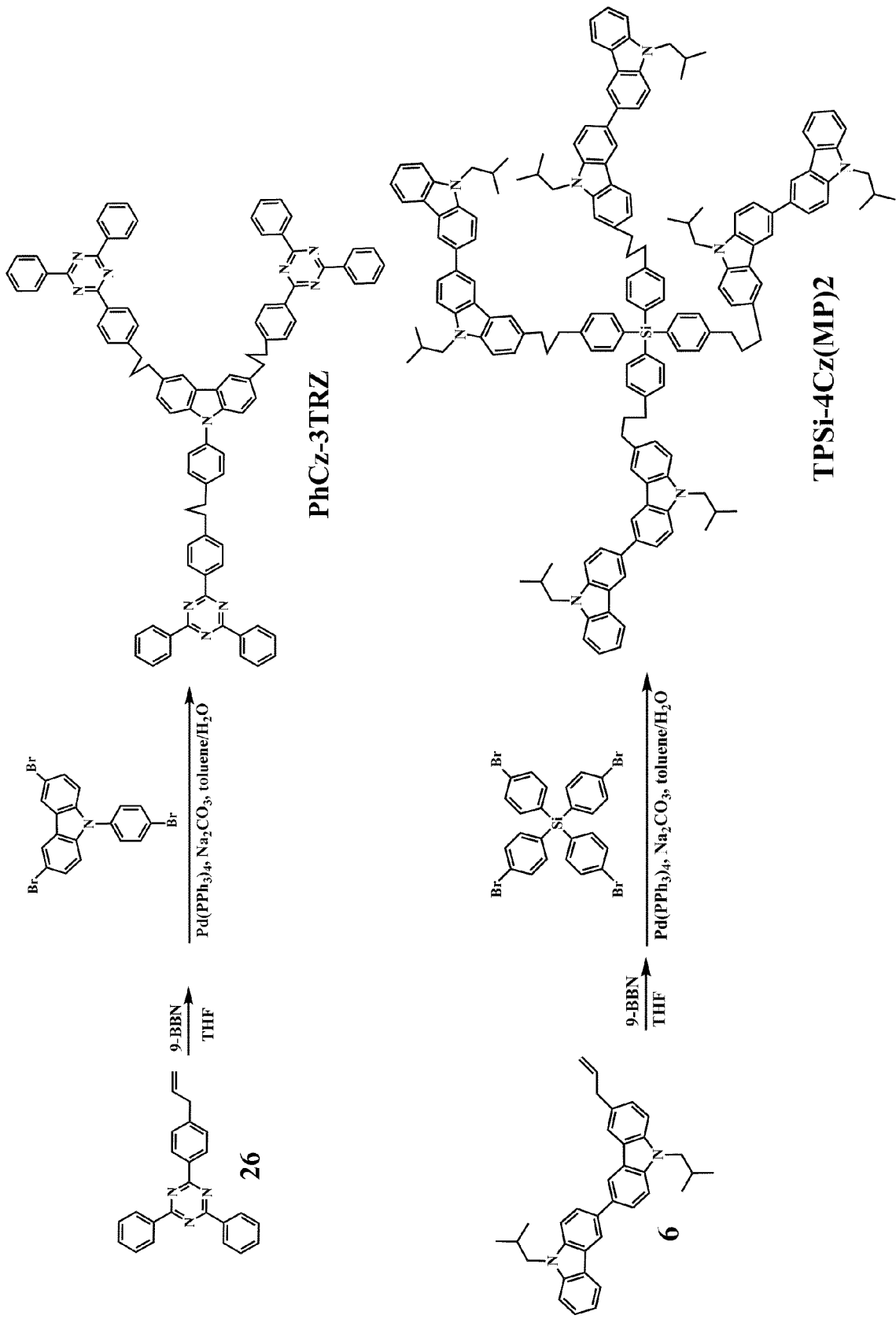
Figure 10:
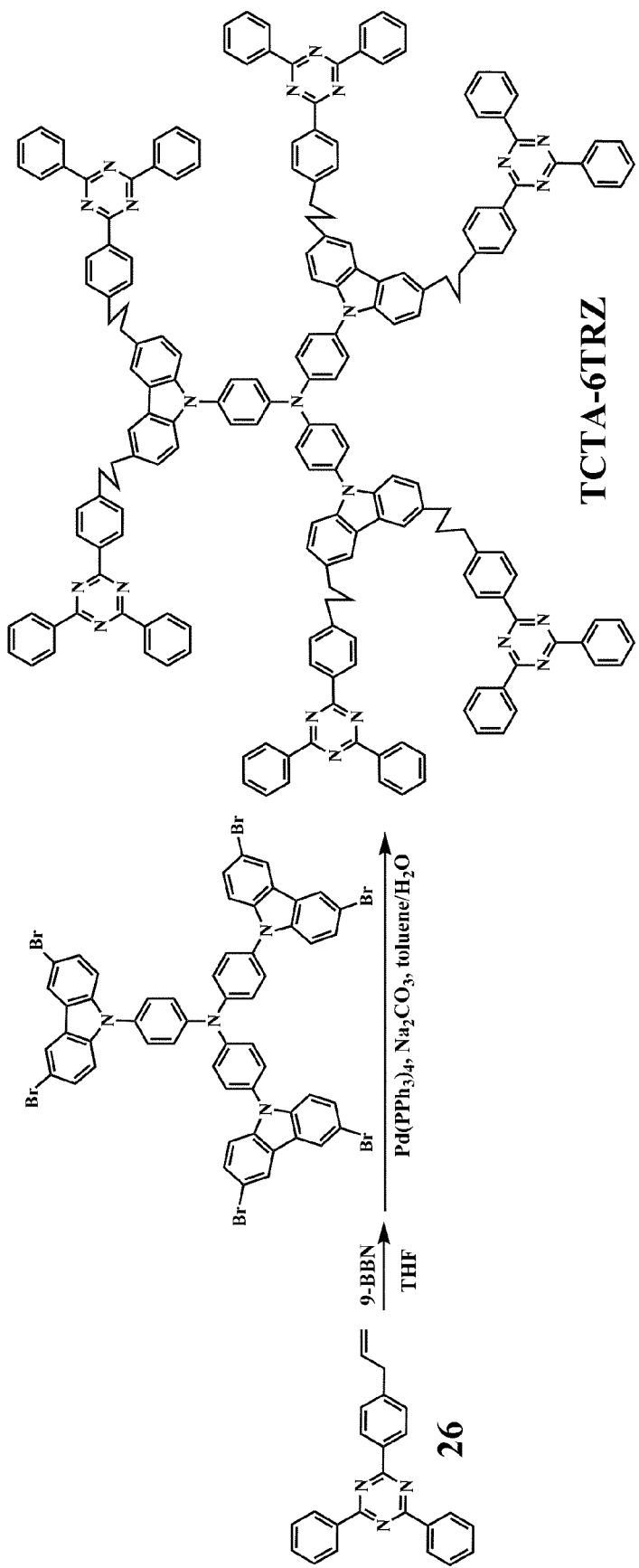

Examples of synthetic routes to these examples can be found in Example 1 and are depicted in FIG. 10.

The synthetic methodology used to prepare the compounds of the present invention can generally be described as convergent. This is true when x or y is greater than 1 in the general structures provided above. In a convergent synthesis the bond between the linker (L) and outer moiety (B or A, respectively, in the general structures provided above) is established first, and the bond between the linker of this structure (outer moiety-linker) and the central moiety (A or B, respectively, in the general structures above) is established second. When x or y is 1 in the general structures provided above, the bonds between the linker and A and B moieties can be established in any order.

The compounds of the present invention form amorphous (also referred to herein as isotropic) materials, including amorphous films, which are useful as bipolar charge-transport host materials. Formation of the compounds via chemical modification as described herein represents a viable solution to circumvent the phase-separation problem associated with physical mixing of charge-transport (electron/hole) materials. The hybrid materials of the present invention exhibit elevated $T_g$ and increased stability against crystallization compared to the ETMs and HTMs as separate entities.

In various embodiments, the compounds described herein exhibit a morphologically stable amorphous phase for at least 6 months, 12 months, 18 months, 2 years, 5 years and 10 years. In various embodiments, amorphous films (e.g. 10 nm to 1 micron thick films) of the compounds described herein are morphologically stable for at least 6 months, 12 months and 18 months, 2 years, 5 years, and 10 years.

In one embodiment, the present invention provides a host material composition comprising a compound or polymer described herein, or a combination thereof.

In another embodiment, the present invention provides an organic light emitting device comprising any of the compounds (or combination of the compounds) described herein, or an organic light emitting device comprising a host material comprising any of the compounds (or combination of the compounds) described herein.

For example, the present invention also provides an OLED device comprising the compounds of the present invention as host materials for triplet emitter materials. For example, 0.1-20% by weight of a triplet emitter can be doped into the host material. Generally, an OLED device comprises an emissive layer disposed between a cathode and an anode. In most cases, additional layers are disposed adjacent to the emissive layer to facilitate charge injection. The electron and hole fluxes through the emissive layer should preferably be balanced without accumulation of charges or excitons at interfaces to maximize OLED device performance. For example, host materials comprising the compounds of the present invention doped with a triple emitter material are suitable for use as the emissive layer in the aforementioned OLED device. This strategy is expected to result in optimized charge injection and transport while preventing phase separation and crystallization, thereby substantially improving OLED device efficiency and lifetime over the state of the art.

The hybrid host materials comprising compounds of the present invention exhibit stability against phase separation, elevated glass transition temperature ($T_g$ from 50 to 200° C.), morphological stability against crystallization, and isolation of the π-systems. They are designed to spread out excitons across the emitter layer by balancing electron and hole fluxes so that the OLED device efficiency and lifetime can be substantially improved. These are improved properties relative to those obtained by physical blending and other chemical modification approaches directed to tunable charge injection and transport properties and prevention of charge and exciton accumulations at interfaces.

The following examples are presented to illustrate the present invention. They are not intended to be limiting in any manner.

EXAMPLE 1

Synthesis and Characterization of Specific Compounds of the Present Invention

Material Synthesis and Characterization. $^1$H NMR spectra were acquired in $CDCl_3$ with an Avance-400 spectrometer (400 MHz) at 298° K. using trimethylsilane (TMS) as an internal standard. Elemental analysis was carried out by Quantitative Technologies, Inc. All chemicals, reagents, and solvents were used as received from commercial sources without further purification except toluene and tetrahydrofuran (THF) that had been distilled over sodium and benzophenone. All reactions were carried out under argon atmosphere and anhydrous conditions unless noted otherwise. Intermediates 9-(2-methylpropyl)carbazole (1), 2-bromo-7-methoxy-9-methylcarbazole (14), 3,6-bis(carbazol-9-yl)carbazole (16), 2,4,6-tris(4-bromophenyl)-1,3,5-triazine, 2-(4-bromophenyl)-4,6-biphenyl-1,3,5-triazine, 1,3,5-tris(4-bromophenyl)benzene, 1,3-bis(5-(4-bromophenyl)-1,3,4-oxadiazole-2-yl)benzene, and 3,5-bis(4-bromophenyl)-4-phenyl-1,2,5-triazol were synthesized according to known procedures.

3,6-dibromo-9-(2-methylpropyl)carbazole (2). Into a suspension of 9-(2-methylpropyl)carbazole (1) (10.0 g, 44.8 mmol) and silica gel (230-400 mesh, 100 g) in methylene chloride (400 ml) was added n-bromosuccinimide (NBS) powder (15.9 g, 89.6 mmol) portionwise at room temperature. The reaction mixture was stirred in the dark and ambient atmosphere for 3 hours before silica gel was removed by filtration. The filtrate was washed with water and dried over $MgSO_4$. Upon evaporating off the solvent, the crude product was purified by column chromatography with hexane as the eluent to yield 2 (16.9 g, 99%) as white crystals. $^1$H NMR (400 MHz, $CDCl_3$, 298 K): δ(ppm) 8.14-8.13 (d, 2H), 7.55-7.53 (m, 2H), 7.27-7.25 (m, 2H), 4.04-4.02 (d, 2H), 2.32-2.30 (m, 1H), 0.97-0.94 (d, 6H).

3-bromo-9-(2-methylpropyl)carbazole (3). The procedure for the synthesis of 2 was followed (1 eq. NBS was used) to prepare 3 from 1 as white crystals in an 84% yield. $^1$H NMR (400 MHz, $CDCl_3$, 298 K): δ(ppm) 8.20-8.19 (d, 1H), 8.05-8.03 (d, 1H), 7.53-7.38 (m, 3H), 7.28-7.21 (m, 2H), 4.04-4.02 (d, 2H), 2.32-2.30 (m, 1H), 0.97-0.94 (d, 6H).

2-(9-(2-methylpropyl)carbazol-3-yl)-4,4,5,5-tetramethyl-[1,3,2]-dioxaborolane (4). Into a solution of 3 (4.2 g, 13.9 mmol) in THF (80 ml) was added BuLi (2.5 M in hexane, 6.95 ml, 17.4 mmol) dropwise at −78° C. The mixture was stirred at this temperature for 3 hours before 2-isopropoxy-4,4,5,5-tetramethyl-[1,3,2]-dioxaborolane (4.05 g, 21.75 mmol) was added in one portion. The reaction mixture was allowed to warm up to room temperature over a period of 12 hours, quenched with water, and then extracted with ether. The organic extracts were combined, washed with brine and water, and dried over $MgSO_4$. Upon evaporating off the solvent, the crude product was purified by column chromatography on silica gel with hexane/methylene chloride 3:1 (v/v) as the eluent to yield 4 (3.95 g, 81%) as a white powder. $^1$H NMR (400 MHz, $CDCl_3$, 298 K): δ(ppm) 8.60 (s, 1H), 8.15-8.10 (d, 1H), 7.90-7.85 (d, 1H), 7.45-7.35 (m, 3H), 7.25-7.15 (m, 1H), 4.10-4.09 (d, 2H), 2.42-2.30 (m, 1H), 1.39 (s, 12H), 0.97-0.95 (d, 6H).

3-bromo-6-(9-(2-methylpropyl)carbazol-3-yl)-9-(2-methylpropyl) carbazole (5). Toluene (30 ml) and $H_2O$ (10 ml) were added into a mixture of 4 (1.2 g, 3.43 mmol), 2 (3.27 g, 8.59 mmol), $Pd(PPh_3)_4$ (0.22 g, 0.17 mmol) and $Na_2CO_3$ (3.43 g, 34 mmol). The reaction mixture was stirred at 90° C. for 12 hours, cooled to room temperature, and then extracted with methylene chloride. The organic extracts were combined, washed with water, and dried over $MgSO_4$. Upon evaporating off the solvent, the crude product was purified by gradient column chromatography on silica gel with hexane/methylene chloride 9:1 to 3:1 (v/v) to yield 5 (0.62 g, 34%) as a white powder. $^1$H NMR (400 MHz, $CDCl_3$, 298 K): δ(ppm) 8.40-8.33 (dd, 2H), 8.30-8.28 (d, 1H), 8.21-8.35 (d, 1H), 7.88-7.76 (m, 2H), 7.56-7.40 (m, 5H), 7.33-7.20 (m, 2H), 4.14-4.09 (m, 4H), 2.46-2.37 (m, 2H), 1.10-0.90 (m, 12H).

3-allyl-6-(9-(2-methylpropyl)carbazol-3-yl)-9-(2-methylpropyl)carbazole (6). THF (20 ml) was added into a mixture of 5 (0.62 g, 1.18 mmol), allyltributyltin (0.78 g, 2.36 mmol), $Pd(PPh_3)_4$ (0.068 g, 0.06 mmol) and LiCl (0.092 g, 3.54 mmol). The reaction mixture was stirred at 90° C. for 24 hours. After evaporating off the solvent, the crude product was purified by gradient column chromatography on silica gel with hexane/methylene chloride 9:1 to 4:1 (v/v) as the eluent to yield 6 (0.35 g, 61%) as a white powder. $^1$H NMR (400 MHz, $CDCl_3$, 298 K): δ(ppm) 8.40-8.38 (dd, 2H), 8.19-8.17 (d, 1H), 8.00 (s, 1H), 7.93-7.79 (m, 2H), 7.50-7.41 (m, 4H), 7.34-7.22 (m, 3H), 6.18-6.08 (m, 1H), 5.20-5.10 (m, 2H), 4.15-4.11 (m, 4H), 3.61-3.59 (d, 2H), 2.50-2.39 (m, 2H), 1.03-1.01 (m, 12H).

3,6-bis(9-(2-methylpropyl)carbazol-3-yl)carbazole (7). Toluene (10 ml) and $H_2O$ (1 ml) were added into a mixture of 4 (0.25 g, 0.72 mmol), 3,6-dibromocarbazole (0.12 g, 0.36 mmol), $Pd(PPh_3)_4$ (0.04 g, 0.036 mmol) and $Na_2CO_3$ (0.37 g, 3.6 mmol). The reaction mixture was stirred at 90° C. for 12 hours, cooled to room temperature, and then extracted with methylene chloride. The organic extracts were combined, washed with water, and dried over $MgSO_4$. Upon evaporating off the solvent, the crude product was purified by gradient column chromatography on silica gel with hexane/methylene chloride 9:1 to 2:1 (v/v) as the eluent to yield 7 (0.27 g, 61%) as a white powder. $^1$H NMR (400 MHz, $CDCl_3$, 298 K): δ (ppm) 8.49-8.44 (d, 4H), 8.21-8.19 (d, 2H), 8.10 (s, broad, 1H), 7.86-7.81 (m, 4H), 7.57-7.42 (m, 8H), 7.27-7.24 (m, 2H), 7.30-7.23 (m, 2H), 4.15-4.10 (m, 4H), 2.45-2.38 (m, 2H), 1.03-0.99 (m, 12H), 4.16-4.14 (d, 4H), 2.46-2.43 (m, 2H), 1.04-1.02 (d, 12H).

3,6-bis(9-(2-methylpropyl)carbazol-3-yl)-9-allylcarbazole (8). A mixture of NaOH (0.1 g, 2.58 mmol) and 7 (0.26 g, 0.43 mmol) in DMSO (20 ml) was stirred at room temperature for 10 minutes before allylbromide (0.26 g, 2.13 mmol) was added in one portion. The mixture was stirred for another 3 hours before quenching with water followed by extraction with methylene chloride. The organic extracts were combined, washed with water and dried over $MgSO_4$. Upon evaporating off the solvent, the crude product was purified by column chromatography on silica gel using hexane/methylene chloride 4:1 (v/v) as the eluent to yield 8 (0.14 g, 49%) as a white powder. $^1H$ NMR (400 MHz, $CDCl_3$, 298 K): δ(ppm) 8.52-8.44 (m, 4H), 8.21-8.19 (d, 2H), 7.87-7.84 (m, 4H), 7.52-7.42 (m, 8H), 7.27-7.25 (m, 2H), 6.15-6.02 (m, 1H), 5.28-5.12 (m, 2H), 5.02-5.01 (d, 2H), 4.16-4.14 (d, 4H), 2.50-2.40 (m, 2H), 1.04-1.03 (d, 12H).

2-bromo-7-(9-(2-methylpropyl)carbazol-3-yl)-9,9-bis(2-methylpropyl) fluorene (10). The procedure for the synthesis of 5 was followed to prepare 10 from 4 and 2,7-dibromo-9,9-bis(2-methylpropyl)fluorene (9) as a white powder in a 49% yield. $^1H$ NMR (400 MHz, $CDCl_3$, 298 K): δ(ppm) 8.34-8.33 (m, 1H), 8.19-8.17 (d, 1H), 7.74-7.67 (m, 4H), 7.60-7.58 (m, 1H), 7.51-7.44 (m, 5H), 7.28-7.24 (m, 1H), 4.15-4.13 (d, 2H), 2.48-2.38 (m, 1H), 2.10-1.95 (m, 4H), 1.02-0.92 (m, 8H), 0.45-0.43 (d, 12H).

2-(7-(9-(2-methylpropyl)carbazol-3-yl)-9,9-bis(2-methylpropyl)fluoren-2-yl)-4,4,5,5-tetramethyl-[1,3,2]-dioxaborolane (11). The procedure for the synthesis of 4 was followed to prepare 11 from 10 as a white powder in a 54% yield. $^1H$ NMR (400 MHz, $CDCl_3$, 298 K): δ(ppm) 8.35-8.34 (d, 1H), 8.19-8.17 (d, 1H), 7.84-7.67 (m, 7H), 7.49-7.41 (m, 3H), 7.28-7.23 (m, 1H), 4.15-4.13 (d, 2H), 2.48-2.38 (m, 1H), 2.12-2.02 (m, 4H), 1.39 (s, 12H), 1.26-1.24 (m, 2H), 1.03-0.87 (m, 6H), 0.42-0.39 (m, 12H).

3-bromo-6-(7-(9-(2-methylpropyl)-carbazol-3-yl)-9,9-bis(2-methylpropyl) fluoren-2-yl)-9-(2-methylpropyl)carbazole (12). The procedure for the synthesis of 5 was followed to prepare 12 from 11 and 2 as a white powder in a 67% yield. $^1H$ NMR (400 MHz, $CDCl_3$, 298 K): δ(ppm) 8.38-8.37 (d, 1H), 8.31-8.30 (m, 2H), 8.21-8.18 (d, 1H), 7.84-7.67 (m, 8H), 7.57-7.42 (m, 5H), 7.32-7.24 (m, 2H), 4.16-4.11 (m, 4H), 2.49-2.35 (m, 2H), 2.14-2.12 (d, 4H), 1.11-1.00 (m, 14H), 0.50-0.48 (m, 12H).

3-allyl-6-(7-(9-(2-methylpropyl)-carbazol-3-yl)-9,9-bis(2-methylpropyl) fluoren-2-yl)-9-(2-methylpropyl)carbazole (13). The procedure for the synthesis of 6 was followed to prepare 13 from 12 as a white powder in a 77% yield. $^1H$ NMR (400 MHz, $CDCl_3$, 298 K): δ(ppm) 8.37-8.35 (m, 2H), 8.21-8.19 (d, 1H), 8.01 (s, 1H), 7.83-7.70 (m, 8H), 7.51-7.24 (m, 7H), 6.07-6.17 (m, 1H), 5.18-5.10 (m, 2H), 4.18-4.10 (m, 4H), 3.62-3.60 (d, 2H), 2.49-2.38 (m, 2H), 2.14-2.12 (d, 4H), 1.11-1.00 (m, 14H), 0.50-0.48 (m, 12H).

2-methoxy-7-allyl-9-methylcarbazole (15). The procedure for the synthesis of 6 was followed to prepare 15 from 2-bromo-7-methoxy-9-methylcarbazole (14) as a yellow powder in a 91% yield. $^1H$ NMR (400 MHz, $CDCl_3$, 298 K): δ(ppm) 7.92-7.89 (m, 2H), 7.16 (s, 1H), 7.05-7.03 (d, 1H), 6.84-6.81 (m, 2H), 6.13-6.02 (m, 1H), 5.17-5.08 (m, 2H), 3.93 (s, 3H), 3.78 (s, 3H), 3.59-3.57 (d, 2H).

3,6-bis(carbazol-9-yl)-9-allylcarbazole (17). The procedure for the synthesis of 8 was followed to prepare 17 from 3,6-bis(carbazol-9-yl)carbazole (16) in a 78% yield. $^1H$ NMR (400 MHz, $CDCl_3$, 298 K): δ(ppm) 8.23 (s, 2H), 8.17-8.15 (d, 4H), 7.66 (s, 4H), 7.42-7.36 (m, 8H), 7.29-7.27 (m, 4H), 6.25-6.10 (m, 1H), 5.37-5.27 (m, 2H), 5.12-5.11 (d, 2H).

2-bromo-dibenzofuran (19). Bromine (7.41 g, 46.38 mmol) was added dropwise to a warm solution (50° C.) of dibenzofuran (18) (6.00 g, 35.67 mmol) in glacial acetic acid (36 ml) in ambient atmosphere. The reaction mixture was stirred at room temperature overnight. The yellow solid was isolated by filtration, and rinsed sequentially with HOAc (9 ml) and $H_2O$ (300 ml). Upon evaporating off the residual solvents, the crude product was purified by vacuum sublimation (80° C., 75 mtorr) to yield 2 (4.50 g, 60%) as a white powder. $^1H$ NMR (400 MHz, $CDCl_3$, 298 K): δ(ppm) 8.08-8.07 (d, J=2.00 Hz, 1H), 7.93-7.91 (d, J=8.00 Hz, 1H), 7.59-7.54 (m, 2H), 7.52-7.44 (m, 2H), 7.39-7.34 (m, 1H).

2,8-dibromo-dibenzofuran (20). The procedure for the synthesis of 19 was followed (1 eq. bromine was used) to prepare 20 from 19 as white crystals in a 50% yield. 1H NMR (400 MHz, $CDCl_3$, 298 K): δ(ppm) 8.04-8.03 (d, J=2.00 Hz, 2H), 7.60-7.59 (d, J=2.00 Hz, 1H), 7.58-7.57 (d, J=2.00 Hz, 1H), 7.47 (s, 1H), 7.44 (s, 1H).

2-(dibenzofuran-2-yl)-4,4,5,5-tetramethyl-[1,3,2]-dioxaborolane (21). The procedure for the synthesis of 4 was followed to prepare 21 from 19 as a white powder in a 59% yield. $^1H$ NMR (400 MHz, $CDCl_3$, 298 K): δ(ppm) 8.45 (s, 1H), 7.99-7.91 (m, 2H), 7.59-7.55 (m, 2H), 7.48-7.43 (m, 1H), 7.37-7.33 (m, 1H), 1.40(s, 12H).

2-bromo-8-(dibenzofuran-2-yl)dibenzofuran (22). The procedure for the synthesis of 5 was followed to prepare 22 from 21 and 20 as a white powder in a 60% yield. $^1H$ NMR (400 MHz, $CDCl_3$, 298 K): δ(ppm) 8.25-8.21 (m, 3H), 8.09-8.07 (m, 1H), 7.86-7.78 (m, 2H), 7.73-7.63 (m, 4H), 7.57-7.52 (m, 2H), 7.46-7.42 (m, 1H).

2-allyl-8-(dibenzofuran-2-yl)dibenzofuran (23). The procedure for the synthesis of 6 was followed to prepare 23 from 22 as a white powder in a 84% yield. $^1H$ NMR (400 MHz, $CDCl_3$, 298 K): δ(ppm) 8.22-8.20 (m, 2H), 8.05-8.02 (m, 1H), 7.85 (m, 1H), 7.77-7.73 (m, 2H), 7.67-7.60 (m, 3H), 7.54-7.47 (m, 2H), 7.41-7.37 (m, 1H), 7.33-7.31 (m, 1H), 6.14-6.01 (m, 1H), 5.19-5.11 (m, 2H), 3.59-3.57 (d, J=6.80 Hz, 2H).

2-allyl-dibenzofuran (24). The procedure for the synthesis of 6 was followed to prepare 24 from 19 as a viscous liquid in a yield of 73%. $^1H$ NMR (400 MHz, $CDCl_3$, 298 K): δ(ppm) 7.94-7.92 (m, 1H), 7.76-7.76 (d, J=1.2 Hz, 1H), 7.56-7.54 (d, J=8.4 Hz, 1H), 7.50-7.42 (m, 2H), 7.34-7.27 (m, 2H), 6.11-6.05 (m, 1H), 5.15-5.10 (m, 2H), 3.56-3.54 (d, J=6.8 Hz, 2H).

1-(3-(carbazol-9-yl)propyl)-3,5-dibromobenzene (30). 9-BBN (0.5 M in THF, 38 mL, 19 mmol) was added dropwise into a solution of 9-allylcarbazole (29) (3.0 g, 14.5 mmol) in THF (10 mL) at 0° C. The mixture was stirred at room temperature for 15 minutes and then at 35° C. for 4 hours before transferring into a mixture of 1,3,5-tribromobenzene (19.5 g, 60.3 mmol), $Pd(PPh_3)_4$ (0.84 g, 0.72 mmol), $K_2CO_3$ (10.0 g, 72.4 mmol), $H_2O$ (15 mL) and THF (15 mL). The reaction mixture was stirred at 90° C. overnight, cooled to room temperature, and then extracted with chloroform. The organic extracts were combined, washed with water and dried over $MgSO_4$. Upon evaporating off the solvent, the crude product was purified by column chromatography on silica gel with hexane/methlylene chloride 10:1 to 9:1 (v/v) as the eluent to yield 30 as a white crystals (5.4 g, 84%). $^1H$ NMR (400 MHz, $CDCl_3$, 298 K): 8.11-8.10 (d, 2H), 7.49-7.45 (m, 3H), 7.34-7.32 (m, 2H), 7.26-7.20 (m, 4H), 4.37-4.33 (t, 2H), 2.65-2.60 (d, J=7.6 Hz, 2H), 2.25-2.18 (m, 2H).

1-(3-(carbazol-9-yl)propyl)-3,5-diallylbenzene (31). The procedure for the synthesis of 6 was followed to prepare 31 from 30 and allyltributyltin (2.25 eq) as a viscous liquid in a 90% yield. $^1H$ NMR (400 MHz, $CDCl_3$, 298 K): δ(ppm) 8.11-8.09 (d, 2H), 7.46-7.42 (m, 2H), 7.33-7.31 (m, 2H), 7.24-7.20 (m, 1H), 6.87-6.85 (m, 3H), 6.00-5.90 (m, 2H), 5.10-5.04 (m, 4H), 4.33-4.29 (t, 2H), 3.34-3.33 (d, 4H), 2.70-2.67 (m, 2H), 2.26-2.20 (m, 2H).

1-(3-(carbazol-9-yl)propyl)-3,5-bis(3-(p-bromophenyl) propyl)benzene (32). The procedure for the synthesis of 30 was followed to prepare 32 from 31 and 1,4-dibromobenzene (5 eq) as a white crystals in a 74% yield. $^1H$ NMR (400 MHz, CDCl₃, 298 K): δ(ppm) 8.11-8.09 (d, 2H), 7.42-7.36 (m, 6H), 7.32-7.30 (m, 2H), 7.23-7.19 (m, 2H), 7.04-7.01 (m, 4H), 6.79 (s, 3H), 4.33-4.29 (t, 2H), 2.68-2.64 (t, J=7.6 Hz, 2H), 2.60-2.56 (q, 8H), 2.24-2.16 (m, 2H), 1.93-1.85 (m, 4H).

1-(3-(carbazol-9-yl)propyl)-3,5-bis(3-(p-(4,4,5,5-tetramethyl-[1,3,2]-dioxaborolan-2-yl)phenyl)propyl)benzene (33). The procedure for the synthesis of 4 was followed to prepare 33 from 32 as a white powder in a 70% yield. ¹H NMR (400 MHz, CDCl₃, 298 K): δ(ppm) 8.10-8.08 (d, 2H), 7.74-7.72 (d, 4H), 7.40-7.38 (m, 2H), 7.32-7.30 (m, 2H), 7.22-7.18 (m, 6H), 6.82-6.80 (m, 3H), 4.33-4.29 (t, 2H), 2.67-2.63 (t, 6H), 2.59-2.55 (t, 4H), 2.23-2.18 (m, 2H), 1.94-1.90 (m, 4H), 1.34 (s, 24H).

3,6-diallyl-9-(2-methylpropyl)carbazole (34). The procedure for the synthesis of 6 was followed to prepare 34 from 2 as a viscous liquid in a 81% yield. ¹H NMR (400 MHz, CDCl₃, 298 K): δ(ppm) 7.88-7.87 (d, 2H), 7.31-7.24 (m, 4H), 6.11-6.05 (m, 2H), 5.15-5.07 (m, 4H), 4.05-4.03 (d, 2H), 3.57-3.55 (d, 4H), 2.40-2.30 (m, 1H), 0.97-0.96 (d, 6H).

3,6-bis(3-(p-bromophenyl)propyl)-9-(2-methylpropyl)carbazole (35). The procedure for the synthesis of 30 was followed to prepare 35 from 34 and 1,4-dibromobenzene as a white powder in a 66% yield. ¹H NMR (400 MHz, CDCl₃, 298 K): δ (ppm) 7.85-7.84 (d, 2H), 7.41-7.37 (m, 4H), 7.30-7.22 (m, 4H), 7.09-7.06 (m, 4H), 4.05-4.03 (d, 2H), 2.83-2.79 (t, 4H), 2.67-2.63 (t, 4H), 2.40-2.30 (m, 1H), 2.06-2.00 (m, 4H), 0.98-0.96 (d, 6H).

3,6-bis(3-(p-(4,4,5,5-tetramethyl-[1,3,2]-dioxaborolan-2-yl)phenyl)propyl)-9-(2-methylpropyl)carbazole (36). The procedure for the synthesis of 4 was followed to prepare 36 from 35 as a white powder in a 69% yield. ¹H NMR (400 MHz, CDCl₃, 298 K): δ (ppm) 7.86 (d, 2H), 7.75-7.73 (m, 4H), 7.29-7.22 (m, 8H), 4.04-4.02 (d, 2H), 2.83-2.80 (t, 4H), 2.73-2.69 (t, 4H), 2.40-2.30 (m, 1H), 2.07-2.00 (m, 4H), 1.34 (s, 24H), 0.98-0.96 (d, 6H).

1,6-bis(3-bromophenoxyl)hexane (38). A suspension of 37 (7.13 g, 41.22 mmol) and NaOH (1.52 g, 38.10 mmol) in acetonitrile (309 ml) was stirred under reflux for 1 h before 1,6-dibromohexane (2.51 g, 10.31 mmol) was added in one portion. The reaction mixture was stirred under reflux for another 22 hours before the precipitates were removed by filtration. The filtrate was quenched with water and extracted with methylene chloride. The extracts were combined, washed with water and dried over MgSO₄. Upon evaporating off the solvent, the crude product was purified by gradient column chromatography on silica gel with hexanes/ethyl acetate 19:1 to 9:1 (v/v) as the eluent to yield 38 (4.02 g, 91%) as a white powder. ¹H NMR (400 MHz, CDCl₃, 298 K): δ(ppm) 7.15-7.11 (m, 2H), 7.07-7.04 (m, 4H), 6.83-6.80 (m, 2H), 3.96-3.93 (t, 4H), 1.82-1.79 (t, 4H), 1.55-1.51 (m, 4H).

1,6-bis(3-(4,4,5,5-tetramethyl-[1,3,2]-dioxaborolan-2-yl)phenoxyl)hexane (39). The procedure for the synthesis of 4 was followed to prepare 39 from 38 as a white powder in a 65% yield. ¹H NMR (400 MHz, CDCl₃, 298 K): δ(ppm) 7.39-7.37 (m, 2H), 7.33-7.26 (m, 4H), 7.01-6.98 (m, 2H), 4.02-3.98 (t, 4H), 1.83-1.79 (t, 4H), 1.56-1.52 (m, 4H), 1.34 (s, 24H).

2-chloro-4,6-di(3-methylphenyl)-1,3,5-triazine (41). A Grignard reagent, bromo(3-methylphenyl)-magnesium (40), prepared by reacting 1-bromo-3-methylbenzene (3.00 g, 17.54 mmol) with Mg (0.65 g, 26.84 mmol) and small amount of iodine in ether (11 ml), was added dropwise into a solution of 2,4,6-trichloro-1,3,5-triazine (1.25 g, 6.75 mmol) containing Pd(dppf)Cl₂ (0.33 g, 0.41 mmol) as a catalyst. The reaction mixture was stirred at room temperature overnight, quenched with 0.2M HCl, and extracted with chloroform. The organic extracts were combined, washed with brine and water, and dried over MgSO₄. Upon evaporating off the solvent, the crude product was purified by column chromatography on silica gel with hexanes/chloroform 5:1 (v/v) as the eluent to yield 43 (0.35 g, 18%) as a white powder. ¹H NMR (400 MHz, CDCl₃, 298 K): δ(ppm) 8.45-8.42 (m, 4H), 7.45-7.44 (d, 4H), 2.49 (s, 6H).

9-(3-(4-bromophenyl)propyl))carbazole (42) The procedure for the synthesis of 32 was followed to prepare 42 from 29 and 1,4-dibromobenzene (3 eq) as a white powder (75.68%). ¹H NMR (400 MHz, CDCl₃, 298 K): δ(ppm) 8.11-8.09 (d, 2H), 7.47-7.38 (m, 4H), 7.33-7.31 (m, 2H), 7.26-7.21 (m, 2H), 7.03-7.01 (d, 2H), 4.35-4.31 (t, 2H), 2.67-2.63 (t, 2H), 2.22-2.18 (m, 2H).

2-(4-(3-(carbazol-9-yl)propyl)phenyl)-4,4,5,5-tetramethyl-[1,3,2]-dioxaborolane (43). The procedure for the synthesis of 4 was followed to prepare 43 from 42 as a white powder in an 80% yield. ¹H NMR (400 MHz, CDCl₃, 298 K): δ(ppm) 8.11-8.09 (d, 2H), 7.76-7.74 (d, 2H), 7.47-7.41 (m, 2H), 7.34-7.32 (m, 2H), 7.24-7.18 (m, 4H), 4.35-4.29 (t, 2H), 2.76-2.72 (m, 2H), 2.28-2.20 (m, 2H), 1.34 (s, 12H).

2-(4-(3-(carbazol-9-yl)propyl)phenyl)-4,6-di(3-methylphenyl)-1,3,5-triazine (44) The procedure for the synthesis of 5 was followed to prepare 44 from 41 and 43 as a white powder in a 37% yield. ¹H NMR (400 MHz, CDCl₃, 298 K): δ(ppm) 8.71-8.70 (d, 2H), 8.58-8.57 (m, 4H), 8.12-8.10 (d, 2H), 7.49-7.36 (m, 10H), 7.26-7.22 (m, 2H), 4.41-4.37 (t, 2H), 2.86-2.83 (t, 2H), 2.53 (s, 6H), 2.33-2.30 (m, 2H).

2-(4-(3-(3,6-dibromocarbazol-9-yl)propyl)phenyl)-4,6-di(3-methylphenyl)-1,3,5-triazine (45) The procedure for the synthesis of 2 was followed to prepare 45 from 44 as a white powder in a 99% yield. ¹H NMR (400 MHz, CDCl₃, 298 K): δ(ppm) 8.71-8.69 (d, 2H), 8.59-8.57 (m, 4H), 8.15-8.14 (d, 2H), 7.57-7.54 (m, 2H), 7.49-7.42 (m, 4H), 7.36-7.34 (d, 2H), 7.22-7.20 (d, 2H), 4.36-4.30 (t, 2H), 2.81-2.77 (t, 2H), 2.53 (s, 6H), 2.29-2.25 (m, 2H).

2,4,6-tris(4-(3-(6-(9-(2-methylpropyl)carbazol-3-yl)-9-(2-methylpropyl)carbazol-3-yl)propyl)phenyl)-1,3,5-triazine (TRZ-3Cz(MP)2). 9-BBN (0.5 M in THF, 3.30 ml, 1.65 mmol) was added dropwise into a solution of 6 (0.21 g, 0.42 mmol) in THF (2 ml) at 0° C. The mixture was stirred at room temperature for 15 minutes and then at 35° C. for 18 hours before transferring into a mixture of 2,4,6-tris(4-bromophenyl)-1,3,5-triazine (0.07 g, 0.13 mmol), Pd(PPh₃)₄ (0.030 g, 0.026 mmol), Na₂CO₃ (3.82 g, 36.0 mmol), H₂O (18 ml) and toluene (30 ml). The reaction mixture was stirred at 85° C. for 40 hours, cooled to room temperature, and then extracted with chloroform. The organic extracts were combined, washed with water and dried over MgSO₄. Upon evaporating off the solvent, the crude product was purified by column chromatography on silica gel with hexane/methylene chloride 3:2 (v/v) as the eluent to yield TRZ-3Cz(MP)2 (0.147 g, 65%) as a pale yellow powder. ¹H NMR (400 MHz, CDCl₃, 298 K): δ(ppm) 8.69-8.67 (d, 6H), 8.40-8.39 (t, 6H), 8.18-8.16 (d, 3H), 8.01 (s, 3H), 7.82-7.78 (m, 6H), 7.47-7.30 (m, 27H), 4.12-4.09 (m, 12H), 2.92-2.82 (m, 12H), 2.48-2.35 (m, 6H), 2.19-2.11 (m, 6H), 1.03-0.99 (m, 36H). Calc. for C₁₂₆H₁₂₃N₉: C, 85.82; H, 7.03; N, 7.15. Found: C, 85.43; H, 7.01; N, 7.11.

2-(4-(3-(6-(9-(2-methylpropyl)carbazol-3-yl)-9-(2-methylpropyl)carbazol-3-yl)propyl)phenyl)-4,6-diphenyl-1,3,5-triazine (TRZ-1Cz(MP)2). The procedure for the synthesis of TRZ-3Cz(MP)2 was followed to prepare TRZ-1Cz(MP)2 from 6 and 2-(4-bromophenyl)-4,6-diphenyl-1,3,5-triazine as a yellow powder in a 63% yield. ¹H NMR (400 MHz, CDCl₃, 298 K): δ(ppm) 8.79-8.76 (m, 4H), 8.71-8.69 (d, 2H), 8.41-8.39 (m, 2H), 8.19-8.17 (d, 1H), 8.02 (s, 1H), 7.81-7.79 (m, 2H), 7.60-7.55 (m, 6), 7.49-7.42 (m, 6H), 7.35-7.33 (m, 2H), 7.25-7.20 (m, 1H), 4.14-4.11 (m, 4H), 2.93-2.82 (m, 4H), 2.44-2.40 (m, 2H), 2.20-2.10 (m, 2H), 1.03-1.01 (m, 12H). Calc. for $C_{56}H_{51}N_5$: C, 84.71; H, 6.47; N, 8.82. Found: C, 84.52; H, 6.39; N, 8.74.

Tris(4-(3-(6-(9-(2-methylpropyl)carbazol-3-yl)-9-(2-methylpropyl) carbazol-3-yl)propyl)phenyl)amine (TPA-3Cz (MP)2). 9-BBN (0.5 M in THF, 3.47 ml, 1.73 mmol) was added dropwise into a solution of 6 (0.28 g, 0.58 mmol) in THF (3 ml) at 0° C. The mixture was stirred at room temperature for 15 minutes and then at 35° C. for 18 hours before transferring into a mixture of tris(4-phenyl)amine (0.84 g, 0.17 mmol), Pd(PPh₃)₄ (0.033 g, 0.029 mmol), $K_2CO_3$ (0.60 g, 4.35 mmol), $H_2O$ (2 ml) and THF (5 ml). The reaction mixture was stirred at 85° C. for 40 hours, cooled to room temperature, and then extracted with chloroform. The organic extracts were combined, washed with water and dried over $MgSO_4$. Upon evaporating off the solvent, the crude product was purified by $^1H$ column chromatography on silica gel with hexane/chloroform 4:1 to 1:1 (v/v) as the eluent to yield TPA-3Cz(MP)2 (0.183 g, 56%) as a white powder. $^1H$ NMR (400 MHz, $CDCl_3$, 298 K): δ (ppm) 8.39-8.37 (dd, 6H), 8.17-8.16 (d, 3H), 7.99 (s, 3H), 7.81-7.77 (m, 6H), 7.47-7.39 (m, 12H), 7.33-7.21 (m, 9H), 7.08-6.99 (dd, 12H), 4.11-4.08 (m, 12H), 2.88-2.84 (t, 6H), 2.70-2.60 (m, 6H), 2.42-2.37 (m, 6H), 2.09-2.03 (m, 6H), 1.01-0.99 (m, 36H). Calc. for $C_{123}H_{123}N_9$: C, 86.93; H, 7.30; N, 5.77. Found: C, 86.65; H, 7.17; N, 5.65.

1,3,5-tris(4-(3-(6-(9-(2-methylpropyl)carbazol-3-yl)-9-(2-methylpropyl) carbazol-3-yl)propyl)phenyl)benzene (TPB-3Cz(MP)2). The procedure for the synthesis of TPA-3Cz(MP)2 was followed to prepare TPB-3Cz(MP)2 from 6 and 1,3,5-tris(4-bromophenyl)benzene as a white powder in a 67% yield. $^1H$ NMR (400 MHz, $CDCl_3$, 298 K): δ(ppm) 8.40-8.39 (dd, 6H), 8.18-8.16 (d, 3H), 8.02 (s, 3H), 7.82-7.78 (m, 6H), 7.75 (s, 3H), 7.63-7.61 (d, 5H), 7.48-7.20 (m, 28H), 4.12-4.10 (d, 12H), 2.92-2.76 (m, 12H), 2.48-2.35 (m, 6H), 2.18-2.10 (m, 6H), 1.02-0.99 (m, 36H). Calc. for $C_{129}N_{126}N_6$: C, 88.01; H, 7.21; N, 4.77. Found: C, 87.65; H, 7.24; N, 4.76.

2,4,6-tris(4-(3-(3,6-bis(9-(2-methylpropyl)carbazol-3-yl) carbazol-9-yl)propyl)phenyl)-1,3,5-triazine (TRZ-3Cz(N)Cz(MP)2). The procedure for the synthesis of TRZ-3Cz (MP)2 was followed to prepare TRZ-3Cz(N)Cz(MP)2 from 8 and 2,4,6-tris(4-bromophenyl)-1,3,5-triazine as a pale yellow powder in a 34% yield. $^1H$ NMR (400 MHz, $CDCl_3$, 298 K): δ(ppm) 8.72-8.870 (d, 6H), 8.50-8.43 (m, 12H), 8.19-8.17 (d, 6H), 7.86-7.82 (m, 12H), 7.49-7.38 (m, 30H), 7.25-7.21 (m, 3H), 4.47-4.43 (m, 6H), 4.12-4.10 (d, 12H), 2.90-2.86 (m, 6H), 2.44-2.36 (m, 12H), 1.01-0.99 (d, 36H). Calc. for $C_{162}H_{144}N_{12}$: C, 86.13; H, 6.43; N, 7.44. Found: C, 85.86; H, 6.38; N, 7.40.

2,4,6-tris(4-(3-(6-(7-(9-(2-methylpropyl)carbazol-3-yl)-9,9-bis(2-methylpropyl)fluoren-2-yl)-9-(2-methylpropyl) carbazol-3-yl)propyl)phenyl)-1,3,5-triazine (TRZ-3Cz(MP) 2F(MP)). The procedure for the synthesis of TRZ-3Cz(MP)2 was followed to prepare TRZ-3Cz(MP)2F(MP) from 13 and 2,4,6-tris(4-bromophenyl)-1,3,5-triazine as a pale yellow powder in a 35% yield. $^1H$ NMR (400 MHz, $CDCl_3$, 298 K): δ (ppm) 8.71-8.69 (d, 6H), 8.37-8.35 (m, 6H), 8.20-8.18 (d, 3H), 8.02 (s, 3H), 7.88-7.68 (m, 24H), 7.50-7.23 (m, 27H), 4.15-4.10 (m, 12H), 2.93-2.82 (m, 12H), 2.49-2.37 (m, 6H), 2.21-2.11 (m, 18H), 1.10-0.98 (m, 42H), 0.49-0.47 (d, 36H). Calc. for $C_{189}H_{195}N_9$: C, 87.56; H, 7.58; N, 4.86. Found: C, 87.64; H, 7.47; N, 4.66.

2,4,6-tris(4-(3-(7-methoxyl-9-methylcarbazol-2-yl)propyl)phenyl)-1,3,5-triazine (TRZ-3Cz(Me)OMe). The procedure for the synthesis of TRZ-3Cz(MP)2 was followed to prepare TRZ-3Cz(Me)OMe from 15 and 2,4,6-tris(4-bromophenyl)-1,3,5-triazine as a white powder in a 51% yield. $^1H$ NMR (400 MHz, $CDCl_3$, 298 K): δ(ppm) 8.69-8.67 (d, 6H), 7.92-7.89 (m, 6H), 7.41-7.39 (d, 6H), 7.16 (s, 3H), 7.08-7.06 (m, 3H), 6.83-6.81 (m, 6H), 3.93 (s, 9H), 3.78 (s, 9H), 2.90-2.81 (m, 12H), 2.18-2.10 (m, 6H) Calc. for $C_{72}H_{66}N_6O_3$: C, 81.33; H, 6.26; N, 7.90. Found: C, 80.90; H, 6.20; N, 7.74.

1,3-bis(5-(4-(3-(6-(9-(2-methylpropyl)carbazol-3-yl)-9-(2-methylpropyl)carbazol-3-yl)propyl)phenyl)-1,3,4-oxadiazol-2-yl)benzene (OXD-2Cz(MP)2). The procedure for the synthesis of TRZ-3Cz(MP)2 was followed to prepare OXD-2Cz(MP)2 from 6 and 1,3-bis(5-(4-bromophenyl)-1,3,4-oxadiazol-2-yl)benzene. The purification was carried out by column chromatography on silica gel with chloroform/ethyl acetate 50:1 (v/v) as the eluent to yield OXD-2Cz(MP)2 (44%) as a pale yellow powder. $^1H$ NMR (400 MHz, $CDCl_3$, 298 K): δ(ppm) 8.84 (s, 1H), 8.40-8.39 (dd, 4H), 8.32-8.30 (dd, 2H), 8.18-8.16 (d, 2H), 8.11-8.08 (d, 4H), 8.00 (s, 2H), 7.82-7.78 (m, 4H), 7.66-7.63 (t, 1H), 7.49-7.32 (m, 16H), 7.25-7.21 (t, 2H), 4.13-4.11 (m, 8H), 2.90-2.88 (t, 4H), 2.82-2.80 (t, 2H), 2.46-2.40 (m, 4H), 2.20-2.10 (m, 4H), 1.03-1.01 (m, 24H). Calc. for $C_{93}H_{88}N_8O_2$: C, 82.76; H, 6.57; N, 8.30. Found: C, 82.38; H, 6.42; N, 8.42.

1,3-bis(5-(4-(3-(3,6-bis(carbazol-9-yl)carbazol-9-yl)propyl)phenyl)-1,3,4-oxadiazol-2-yl)benzene (OXD-2Cz3). The procedure for the synthesis of OXD-2Cz(MP)2 was followed to prepare OXD-2Cz3 from 17 and 1,3-bis(5-(4-bromophenyl)-1,3,4-oxadiazol-2-yl)benzene as a pale yellow powder in a 52% yield. $^1H$ NMR (400 MHz, $CDCl_3$, 298 K): δ(ppm) 8.87 (s, 1H), 8.33-8.31 (dd, 2H), 8.23-8.22 (d, 4H), 8.16-8.14 (d, 12H), 7.71-7.60 (m, 9H), 7.46-7.37 (m, 20H), 7.36-7.25 (m, 8H), 4.59-4.56 (t, 4H), 2.99-2.95 (t, 4H), 2.50-2.46 (m, 4H). Calc. for $C_{100}H_{68}N_{10}O_2$: C, 83.31; H, 4.75; N, 9.72. Found: C, 82.98; H, 4.62; N, 9.76.

2-(4-(3-(dibenzofuran-2-yl)propyl)phenyl)-4,6-diphenyl-1,3,5-triazine (TRZ-1DBF1). The procedure for the synthesis of TRZ-3Cz(MP)2 was followed to prepare TRZ-1DBF1 from 24 and 2-(4-bromophenyl)-4,6-diphenyl-1,3,5-triazine as a white powder in a yield of 65%. $^1H$ NMR (400 MHz, $CDCl_3$, 298 K): δ(ppm) 8.80-8.77 (m, 4H), 8.72-8.70 (d, 2H), 7.95-7.93 (d, 1H), 7.78 (s, 1H), 7.63-7.55 (m, 7H), 7.51-7.49 (d, 1H), 7.46-7.40 (m, 3H), 7.35-7.30 (m, 2H), 2.86-2.83 (m, 4H), 2.20-2.05 (m, 2H). Calc. for $C_{36}H_{27}N_3O$: C, 83.53; H, 5.26; N, 8.12. Found: C, 83.89; H, 5.11; N, 8.14.

2,4,6-Tris(4-(3-(dibenzofuran-2-yl)propyl)phenyl)-1,3,5-triazine (TRZ-3DBF1). The procedure for the synthesis of TRZ-3Cz(MP)2 was followed to prepare TRZ-3DBF1 from 24 and 2,4,6-tris(4-bromophenyl)-1,3,5-triazine as a white powder in a 33% yield. $^1H$ NMR (400 MHz, $CDCl_3$, 298 K): δ(ppm) 8.70-8.68 (d, 6H), 7.95-7.93 (d, 3H), 7.78 (s, 3H), 7.56-7.54 (d, 3H), 7.50-7.48 (d, 3H), 7.46-7.39 (m, 9H), 7.35-7.28 (m, 6H), 2.86-2.83 (m, 12H), 2.20-2.05 (m, 6H). Calc. for $C_{66}H_{51}N_3O_3$: C, 84.86; H, 5.50; N, 4.50. Found: C, 84.46; H, 5.46; N, 4.42.

2-(4-(3-(8-(dibenzofuran-2-yl)dibenzofuran-2-yl)propyl)phenyl)-4,6-diphenyl-1,3,5-triazine (TRZ-1DBF2). The procedure for the synthesis of TRZ-3Cz(MP)2 was followed to prepare TRZ-1DBF2 from 23 and 2-(4-bromophenyl)-4,6-diphenyl-1,3,5-triazine as a white powder in a 55% yield. $^1H$ NMR (400 MHz, $CDCl_3$, 298 K): δ(ppm) 8.77-8.76 (m, 4H), 8.71-8.69 (m, 2H), 8.23-8.18 (m, 2H), 8.15-8.00 (m, 1H), 7.85-7.84 (m, 1H), 7.79-7.72 (m, 2H), 7.68-7.30 (m, 15H), 2.90-2.84 (m, 4H), 2.20-2.10 (m, 2H). Calc. for $C_{48}H_{33}N_3O_2$: C, 84.31; H, 4.86; N, 6.15. Found: C, 83.67; H, 4.81; N, 6.15.

2,4,6-tris(4-(3-(8-(dibenzofuran-2-yl)dibenzofuran-2-yl)propyl)phenyl)-1,3,5-triazine (TRZ-3DBF2). The procedure for the synthesis of TRZ-3Cz(MP)2 was followed to prepare TRZ-3DBF2 from 23 and 2,4,6-tris(4-bromophenyl)-1,3,5-triazine as a white powder in a 44% yield. $^1$H NMR (400 MHz, CDCl$_3$, 298 K): δ(ppm) 8.71-8.65 (m, 6H), 8.22-8.17 (m, 5H), 8.03-7.98 (m, 4H), 7.83 (s, 3H), 7.78-7.71 (m, 6H), 7.67-7.56 (m, 9H), 7.53-7.52 (m, 3H), 7.49-7.30 (m, 15H), 2.86-2.83 (m, 12H), 2.20-2.05 (m, 6H). Calc. for C$_{102}$H$_{69}$N$_3$O$_6$: C, 85.51; H, 4.85; N, 2.93. Found: C, 85.22; H, 4.74; N, 3.08.

3,5-Bis(4-(3-(8-(dibenzofuran-2-yl)dibenzofuran-2-yl)propyl)phenyl)-4-phenyl-1,2,5-triazole (TAZ-2DBF2). The procedure for the synthesis of TRZ-3Cz(MP)2 was followed to prepare TAZ-2DBF2 from 23 and 3,5-bis(4-bromophenyl)-4-phenyl-1,2,5-triazole. Purification was carried out by column chromatography on silica gel with chloroform/ethyl acetate 25:1 to 9:1 (v/v) as the eluent to yield the product as a white powder (35%). $^1$H NMR (400 MHz, CDCl$_3$, 298 K): δ (ppm) 8.21-8.18 (m, 4H), 8.03-8.01 (d, 2H), 7.80 (s, 2H), 7.63-7.72 (m, 4H), 7.67-7.59 (m, 6H), 7.50-7.47 (m, 4H), 7.42-7.33 (m, 9H), 7.28-7.26 (m, 1H), 7.16-7.11 (m, 6H), 2.81-2.77 (t, 4H), 2.69-2.65 (t, 4H), 2.09-2.00 (m, 4H). Calc. for C$_{74}$H$_{51}$N$_3$O$_4$: C, 84.95; H, 4.91; N, 4.02. Found: C, 84.61; H, 4.76; N, 3.86.

1,3-Bis(4-(3-(8-(dibenzofuran-2-yl)dibenzofuran-2-yl)propyl)phenyl)-1,3,4-oxadiazol-2-yl)benzene (OXD-2DBF2). The procedure for the synthesis of TRZ-3Cz(MP)2 was followed to prepare OXD-2DBF2 from 23 and 1,3-bis(5-(4-bromophenyl)-1,3,4-oxadiazol-2-yl)benzene as a white powder in a 35% yield. $^1$H NMR (400 MHz, CDCl$_3$, 298 K): δ(ppm) 8.83 (s, 1H), 8.33-8.30 (m, 2H), 8.21-8.19 (m, 4H), 8.12-8.09 (d, 4H), 8.02-8.00 (d, 2H), 7.80 (s, 2H), 7.76-7.58 (m, 10H), 7.35-7.46 (m, 4H), 7.41-7.30 (m, 8H), 2.81-2.77 (t, 4H), 2.69-2.65 (t, 4H), 2.09-2.00 (m, 4H). Calc. for C$_{77}$H$_{52}$N$_4$O$_6$: C, 81.90; H, 4.64; N, 4.96. Found: C, 81.49; H, 4.52; N, 4.95.

Polymer 1—poly(iso-butylcarbazole-co-biphenylpyridine). Into a mixture of 36 (0.200 g, 0.281 mmol), 2,6-dibromopyridine (0.067 g, 0.281 mmol), Pd$_2$(dba)$_3$ (6.4 mg, 7.0 μmol), tri(o-tolyl)phosphine (8.6 mg, 28 μmol) and K$_2$CO$_3$ (0.387 g, 2.81 mmol) was added THF (4.2 mL) and H$_2$O (1.4 mL). The reaction mixture was stirred at 85° C. under dark for 48 hours before cooling to room temperature. The aqueous solution was removed with a pipette. The organic phase was diluted with chloroform, and washed with 5% aqueous NaCN solution till no further bleaching occurs. The organic solution was concentrated and precipitated in methanol and then in hexane. The collected solid was subjected to Soxhlet extraction with methanol, hexane and acetone to yield Polymer 1 as a white solid (0.11 g, 69%). $^1$H NMR (400 MHz, CDCl$_3$, 298 K): δ(ppm) 8.05-8.03 (d, J=8 Hz, 4H), 7.88 (s, 1H), 7.71-7.66 (m, 1H), 7.58-7.57 (m, 2H), 7.36-7.20 (m, 7H), 4.01-3.99 (d, 2H), 2.85-2.81 (t, 4H), 2.76-2.72 (t, 4H), 2.35-2.28 (m, 1H), 2.11-2.02 (m, 4H), 0.95-0.93 (d, 6H). M$_W$=80,100, M$_n$=21,900.

Polymer 2—poly(carbazolylphenylene-co-biphenylpyridine). The procedure for the synthesis of Polymer 1 was followed to prepare Polymer 2 from 33 and 2,6-dibromopyridine as a white solid in a yield of 61%. $^1$H NMR (400 MHz, CDCl$_3$, 298 K): δ(ppm) 8.06-8.02 (m, 6H), 7.71-7.65 (m, 1H), 7.61-7.56 (m, 2H), 7.41-7.15 (m, 10H), 4.32-4.25 (m, 2H), 2.75-2.55 (m, 10H), 2.20 (br, s, 2H), 1.96 (br, s, 4H). M$_W$=26,800, M$_n$=8,410.

Polymer 3—poly(triazinylcarbazole). The procedure for the synthesis of Polymer 1 was followed to prepare Polymer 3 from 45 and 39 as a yellow-green solid in a yield of 81%. $^1$H NMR (400 MHz, CDCl$_3$, 298 K): δ(ppm) 8.72-8.50 (m, 6H), 8.29 (br, s, 2H), 7.70-7.64 (m, 2H), 7.45-7.22 (m, 14H), 6.83-6.80 (m, 2H), 4.30 (br, s, 2H), 3.99 (br, s, 4H), 2.75 (br, s, 2H), 2.53-2.46 (m, 6H), 2.25 (br, s, 2H), 1.82 (br, s, 4H), 1.54 (br, s, 4H). M$_W$=38,300, M$_n$=11,900.

EXAMPLE 2

Properties of Specific Compounds of the Present Invention

Morphology, Thermal Stability, and Phase Transition Temperatures. Thermogravimetric analysis was performed in a TGA/DSC system (SDT Q600, TA Instruments) at a ramping rate of 10° C./min under a nitrogen flow of 50 ml/minute. Thermal transition temperatures were determined by differential scanning calorimetry (Perkin-Elmer DSC-7) with a continuous N$_2$ purge at 20 ml/minute. Samples were preheated to above T$_m$ and then cooled down to −30° C. at −100° C./minute before the reported second heating and cooling scans were recorded at 20° C./minute. The nature of phase transition was characterized by hot-stage polarizing optical microscopy (DMLM, Leica, FP90 central processor and FP82 hotstage, Mettler Toledo). Absorption spectra of dilute solutions in chloroform at a concentration of 10$^{-7}$ to 10$^{-6}$ M were acquired on a UV-Vis-NIR spectrophotometer (Lambda-900, Perkin-Elmer).

Electrochemical Characterization. Cyclic voltammetry was conducted on an EC-Epsilon potentiostat (Bioanalytical Systems Inc.) at a concentration of 10$^{-3}$ M in acetonitrile/toluene (1:1 by volume) containing 0.1 M tetraethylammonium tetrafluoroborate as the supporting electrolyte. A silver/silver chloride (Ag/AgCl) wire, a platinum wire, and a glassy carbon disk (3-mm diameter) were used as the reference, counter, and working electrodes, respectively, to complete a standard 3-electrode cell. The supporting electrolyte was purified as described previously, and the solvents acetonitrile and toluene were distilled over calcium hydride and sodium/benzophenone, respectively. The dilute sample solutions in acetonitrile:toluene (1:1 by volume) exhibit reversible reduction and oxidation waves against the Ag/AgCl reference electrode. The reduction and oxidation potentials were adjusted to ferrocene serving as an internal standard with an oxidation potential of 0.51±0.02 V over Ag/AgCl. The resultant reduction and oxidation potentials, E$_{1/2}$(red) and E$_{1/2}$(oxd), relative to (Fc/Fc+) were used to calculate the LUMO and HOMO levels as −4.8 eV-qE$_{1/2}$(red) and −4.8 eV-qE$_{1/2}$(oxd), respectively, where q is the electron charge.

Triplet Energy Measurement. Phosphorescence spectra were gathered using a Fluorolog-3 spectrofluorometer (Jobin Yvon, Horiba) and were corrected for the efficiency of the monochromator and the spectral response of the photomultiplier tube. Samples (10$^{-4}$ M) were dissolved in ethyl acetate in NMR tubes and inserted into a small liquid nitrogen Dewar to measure the phosphorescence spectra at 77 °K. As has been customary, the maximum of highest-energy 0-0 vibronic band in the phosphorescence spectrum was assigned as energy of the lowest triplet state. Phosphorescence measurements were also carried out with 10% butyl iodide added to the ethyl acetate to enhance the 0-0 vibronic transition and to help differentiate between phosphorescence and fluorescence.

Thin Film Preparation and Characterization. Films of hybrid compounds and mixtures were prepared by spin coating from 2 wt % chlorobenzene solutions at 2500 rpm on microscope glass slides followed by drying under vacuum overnight. The thicknesses of the resultant films were determined by optical interferometry (Zygo New Views 5000). Thermal annealing was performed under argon at elevated temperatures. The film morphology, including melting points where applicable, was characterized by hot-stage polarizing optical microscopy. Photoluminescence was characterized using a spectrofluorimeter (Quanta Master C-60SE, Photon Technology International) with a liquid light guide directing excitation at 360 nm onto the sample film at normal incidence.

Phosphorescent OLED Device Fabrication and Characterization. Glass substrates coated with patterned ITO were thoroughly cleaned and treated with oxygen plasma prior to deposition of a 10-nm-thick $MoO_3$ layer by thermal evaporation at 0.1 nm/second. The emitting layers comprising host: Ir(m-ppy)$_3$ at a mass ratio of 10:1 was then prepared by spin-coating from 2.0 wt % toluene solutions at 4000 rpm for 2 minutes in a nitrogen-filled glove box with oxygen level less than 1 ppm. The resultant film thickness was 40~50 nm determined by optical interferometry (Zygo NewView 5000). Layers of TPBI (30 nm) and CsF (1 nm) were then consecutively deposited 0.1 nm/s and 0.02 nm/s, respectively. The devices were completed by thermal evaporation of Al (100 nm) at 1 nm/s through a shadow mask to define an active area of 0.1 cm$^2$. All evaporation processes were carried out at a base pressure less than $4 \times 10^{-6}$ Ton. All devices were encapsulated with cover glass and glue for characterization with a source-measure unit (Keithley 2400) and a spectroradiometer (PhotoResearch PR650). Only the front-view performance data were collected.

In addition to precluding phase separation, the flexible linkages connecting the two charge-transport moieties in the non-conjugated bipolar hybrid molecules serve to increase entropy because of the more abundant conformations, which is conducive to solubility in benign solvents to facilitate materials purification and solution processing. Furthermore, the increased entropy with flexible linkages presents a higher free energy barrier to crystallization from glassy state, thereby improving morphological stability against crystallization over relatively rigid conjugated and non-conjugated bipolar hybrid molecules without flexible linkages. Depicted in FIG. 1 are three representative non-conjugated bipolar hybrid compounds with propylene linkages, TRZ-1Cz(MP)2, TRZ-3Cz(MP)2, and OXD-2Cz(MP)2 that were synthesized for an investigation of their thermal, morphological, electrochemical, fluorescence, and phosphorescence properties. These hybrid compounds consist of a hole-transport moiety Cz(MP)2 and an electron-transport moiety TRZ or OXD.

Figure 2:
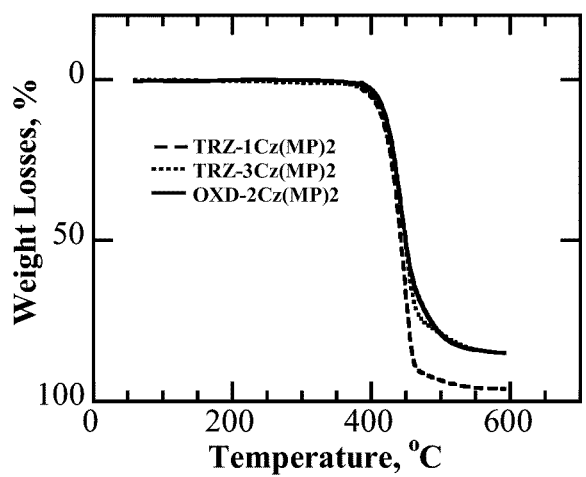
FIG. 2. TGA thermograms of hybrid compounds recorded at a heating rate of 10° C./min under nitrogen atmosphere. The decomposition temperatures at a weight loss of 5% are 399, 403 and 407° C. for TRZ-1Cz(MP)2, TRZ-3Cz(MP)2 and OXD-2Cz(MP)2, respectively.
Figure 3:
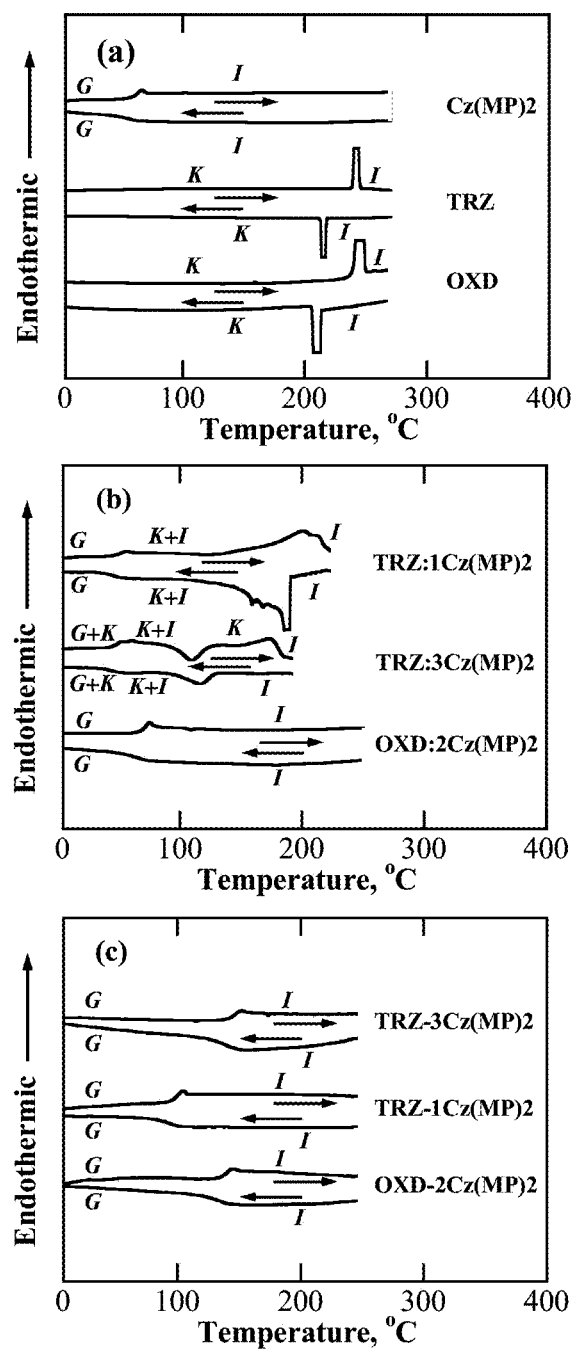
FIG. 3. DSC heating and cooling scans at ±20° C./min of samples comprising (a) hole- and electron-transport moieties, (b) mixtures thereof, and (c) non-conjugated bipolar compounds that have been preheated to beyond their melting points followed by quenching to −30° C. Symbols: G, glassy; K, crystalline; I, isotropic.

The results from thermogravimetric analysis compiled in FIG. 2 reveal their thermal stability to 400° C. at about 5 wt % weight loss. Solid morphologies of the three independent building blocks, three bipolar compounds, and their corresponding mixtures, TRZ:1Cz(MP)2, TRZ:3Cz(MP)2, and OXD:2Cz(MP)2 were characterized by differential scanning calorimetry and hot-stage polarizing optical microscopy. The DSC thermograms compiled in FIG. 3 indicate that the building blocks and their mixtures are crystalline, semicrystalline or amorphous with a glass transition temperature, $T_g$, below 65° C., while all the hybrid compounds are amorphous with a $T_g$ near or above 100° C.

Table 1: Electrochemical properties of compounds determined by the oxidation and reduction scans presented in FIG. 5.

| Compound | | $E_{1/2}(red)^{[a,b]}$ vs Ag/AgCl (V) | $E_{1/2}(red)^{[c]}$ vs Fc/Fc$^+$ (V) | $E_{1/2}(oxd)^{[a,b]}$ vs Ag/AgCl (V) | $E_{1/2}(oxd)[c]$ vs Fc/Fc$^+$ (V) | HOMO$^{[d]}$ (eV) | LUMO$^{[e]}$ (eV) |
|---|---|---|---|---|---|---|---|
| TRZ | TRZ | −1.67 | −2.18 | | | | −2.6 |
| OXD | OXD | −1.86 | −2.37 | | | | −2.4 |
| Cz(MP)2 | Cz(MP)2 | | | 0.92 | 0.41 | −5.2 | |
| TRZ-1Cz(MP)2 | TRZ | −1.69 | −2.20 | | | | −2.6 |
| | Cz(MP)2 | | | 0.92 | 0.41 | −5.2 | |
| TRZ-3Cz(MP)2 | TRZ | −1.72 | −2.23 | | | | −2.6 |
| | Cz(MP)2 | | | 0.89 | 0.38 | −5.2 | |
| OXD-2Cz(MP)2 | OXD | −1.83 | −2.34 | | | | −2.5 |
| | Cz(MP)2 | | | 0.88 | 0.37 | −5.2 | |

[a]Half-wave potentials, $E_{1/2}$, determined as the average of forward and reverse reduction or oxidation peaks.
[b]Reduction and oxidation scans of 10$^{-3}$ M solutions in acetonitrile/toluene (1:1 by volume) with 0.1 M tetrabutylammonium tetrafluoroborate as the supporting electrolyte.
[c]Relative to ferrrocene/ferrocenium (Fc/Fc$^+$) with an oxidation potential at 0.51 ± 0.02 V vs Ag/AgCl
[d]Calculated using the equation HOMO = −4.8 eV − qE$_{1/2}$(oxd) eV, where q is the electron charge and E$_{1/2}$(oxd) is the oxidation potential over Fc/Fc$^+$.
[e]Calculated using the equation LUMO = −4.8 eV − qE$_{1/2}$(red) eV, where q is the electron charge and E$_{1/2}$(red) is the reduction potential over Fc/Fc$^+$.

Figure 4:
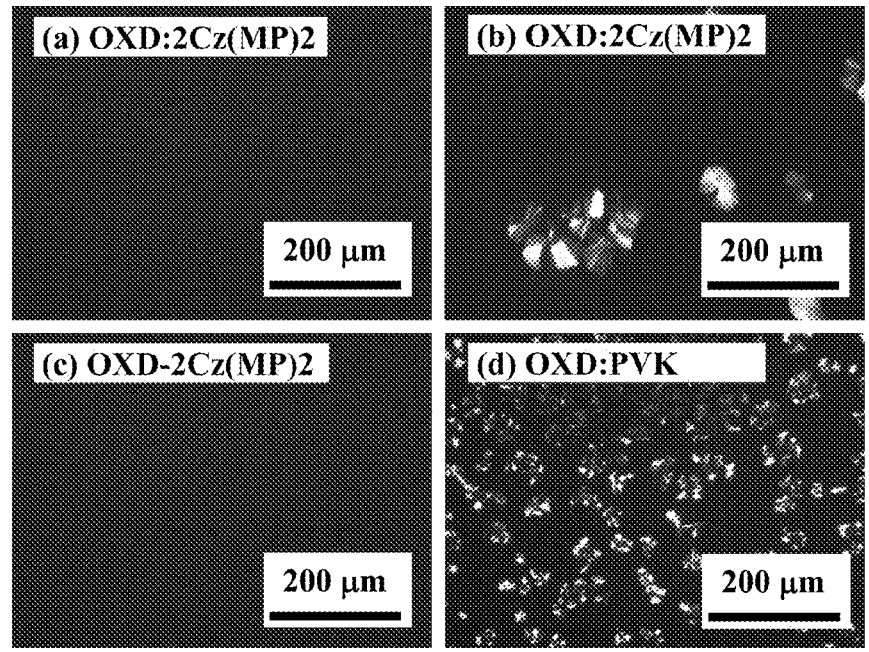
FIG. 4. Polarizing optical micrographs of films from spin-cast chlorobenzene of OXD:2Cz(MP)2 mixture (a) before and (b) after thermal annealing at 32° C. for 3 days; (c) that of an OXD-2Cz(MP)2 film before and after thermal annealing at 100° for 3 days; and (d) that of an OXD:PVK mixture at 30:70 mass ratio after thermal annealing at 100° C. for 3 days.

The amorphous OXD:2Cz(MP)2 mixture observed under differential scanning calorimetry and polarizing optical microscopy was further evaluated for phase separation via thermal annealing at 32° C., viz. a reduced temperature, $T/T_g$=0.91, for three days. While the pristine, spin-cast film of OXD:2Cz(MP)2 was amorphous under polarizing optical microscopy (FIG. 4a), phase separation and/or crystallization occurred upon thermal annealing at 32° C. for 3 days (FIG. 4b). The thermally annealed film was further characterized by polarizing optical microscopy to yield melting points at 150 and 185° C., which fall between the melting points of Cz(MP)2 (144° C.) and OXD (240° C.) also determined by polarizing optical microscopy for spin-cast films left at room temperature for 2 to 3 days. These results suggest a complex phase behavior of the OXD:2Cz(MP)2 mixture. As shown in FIG. 4c, the amorphous character persisted in the OXD-2Cz(MP)2 film upon thermal annealing at 100° C., i.e., the same reduced temperature and annealing time as for OXD:2Cz(MP)2, indicating that the hybrid compound is not vulnerable to phase separation and that it is resistant to thermally activated crystallization. Poly(N-vinylcarbazole), PVK, mixed with OXD at a 70:30 mass ratio was employed as the host for iridium(III) bis[2-(4,6-difluorophenyl)-pyridinato-N, C2] picolinate (FIrpic). The pristine, spin-cast film of this bipolar host material was found to be amorphous with the same optical micrograph as shown in FIG. 4a or c, but phase separation and/or crystallization emerged in FIG. 4d upon thermal annealing at 100° C. for 3 days. Moreover, the crystallites observed under polarizing optical microscopy were found to melt at 230° C., close to the melting point of OXD.

Figure 5:
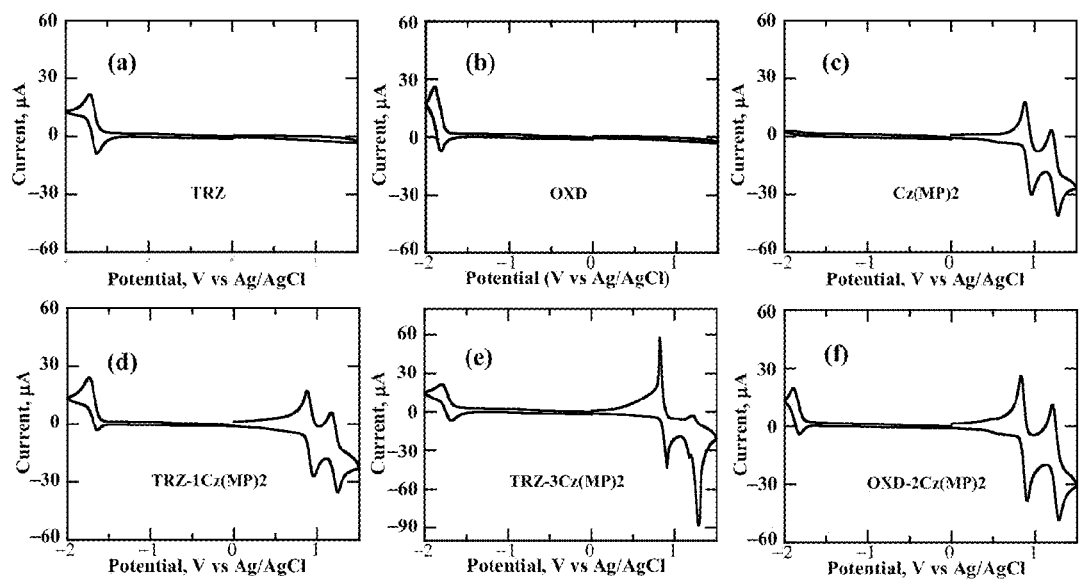
FIG. 5. Cyclic voltammetric scans of compounds in acetonitrile/toluene (1:1 by volume) at $10^{-3}$ M with 0.1 M tetrabutylammonium tetrafluoroborate as the supporting electrolyte.

The electrochemical properties of the non-conjugated bipolar compounds and their building blocks are characterized by cyclic voltammetry. The results presented in FIG. 5 illustrate that the oxidation and reduction scans of the hybrids are essentially the composites of those of their constituent hole- and electron-transport moieties. The key data summarized in Table 1 indicates that the HOMO levels of TRZ-1Cz(MP)2, TRZ-3Cz(MP)2 and OXD-2Cz(MP)2 are placed at −5.2 eV, a value identical to that of the hole-transporting Cz(MP)2. The LUMO levels of −2.6 eV for TRZ-1Cz(MP)2 and TRZ-3Cz(MP)2, and −2.5 eV for OXD-2Cz(MP)2, are also equal within error to those of the electron-transporting TRZ and OXD, respectively. With a HOMO level at −5.2 eV, which is close to the work function of PEDOT:PSS at 5.1 eV, and a LUMO level at −2.5 to −2.6 eV, which is relatively close to the work function of LiF/Al at 2.9 eV, these non-conjugated bipolar compounds are expected to facilitate hole and electron injection in phosphorescent OLED devices. With an interruption of π-conjugation between the two moieties by a propylene linkage, the HOMO and LUMO levels of non-conjugated bipolar hybrid compounds are essentially imported from those of the hole- and electron-transport moieties as independent chemical entities. The LUMO and HOMO levels in conjugated bipolar hybrid compounds, however, are generally affected by the finite extent of π-conjugation between the two moieties.

Figure 6:
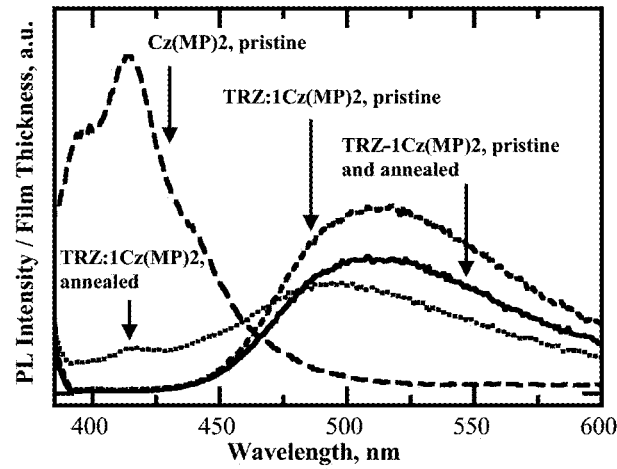
FIG. 6. Fluorescence spectra with excitation at 360 nm of approximately 45-nm-thick, spin-cast films of Cz(MP)2, TRZ-1Cz(MP)2, and TRZ:1Cz(MP)2; thermal annealing was performed at 20° C. above $T_g$ under argon for ½ hour FIG. 7. (a) UV-vis absorption spectra in molecular extinction coefficients, ε, of OXD-2Cz(MP)2, Cz(MP)2 and OXD. Phosphorescence spectra of (b) Cz(MP)2, (c) OXD, and (d) OXD-2Cz(MP)2 at 77 K in ethyl acetate at $10^{-4}$ M, for which the $E_T$ values were determined by the 0-0 transitions as indicated by arrows.

In addition to phase separation detected by microscopy (see FIG. 4), fluorescence spectroscopy was employed to uncover molecular aggregation in non-conjugated bipolar compounds and their equivalent mixtures. To facilitate data interpretation, TRZ-1Cz(MP)2 was used along with TRZ:1Cz(MP)2 based on the facts that TRZ was found to be essentially nonemissive and that OXD showed fluorescence in the 400 to 450 nm region largely overlapping with that of Cz(MP)2. Approximately 45-nm-thick amorphous films of TRZ-1Cz(MP)2, TRZ:1Cz(MP)2, and Cz(MP)2 prepared by spin-coating from chlorobenzene were photoexcited at 360 nm, and their fluorescence spectra normalized with film thickness are presented in FIG. 6. The pristine TRZ-1Cz(MP)2 and TRZ:1Cz(MP)2 films exhibited similar fluorescence in the same spectral range from 450 to 600 nm, representing a red-shift from that of Cz(MP)2 by about 90 nm. These broad and red-shifted fluorescence peaks at 2.4 eV originated from exciplex formation between TRZ and Cz(MP)2 moieties in the hybrid compound and their equimolar mixture, as expected of the offset between the HOMO level of Cz(MP)2 and the LUMO level of TRZ in addition to the Coulomb attraction energy. The lower fluorescence intensity from the pristine film of TRZ-1Cz(MP)2 than that of TRZ:1Cz(MP)2 could have arisen from the less extent of inter- and/or intra-molecular exciplex formation in the former caused by steric hindrance in the presence of a propylene spacer. Thermal annealing of the TRZ-1Cz(MP)2 film at 20° C. above its $T_g$ for ½ hour did not result in any change in the amorphous character and the fluorescence spectrum. Upon thermal annealing under the same condition, polycrystalline domains emerged from the pristine TRZ:1Cz(MP)2 film with a melting point at 178° C., which is distinct from those of TRZ and Cz(MP)2 at 242 and 144° C., respectively as noted above. The polarizing optical micrographs of thermally annealed TRZ-1Cz(MP)2 and TRZ:1Cz(MP)2 films were obtained. As shown in FIG. 6, phase separation accompanied by crystallization led to much reduced, blue-shifted exciplex emission as well as weak emission between 400 and 450 nm attributable to Cz(MP)2. Thus, the hybrid compound is preferable over its equivalent mixture from the standpoint of morphological stability, but the issue of exciplex formation in both material systems must be addressed. Whereas exciplex emission involving bipolar mixed hosts is frequently observed in photoluminescence, it is absent in electroluminescence where triplet emitters serve as charge traps with improved device efficiencies at lower driving voltages compared to the constituent unipolar hosts. To ensure effective charge trapping on the emitter, its LUMO level must be lower than that of the electron-transport component, while its HOMO level higher than that of the hole-transport component, an idea to be incorporated in the design of non-conjugated bipolar hybrid compounds.

Figure 7:
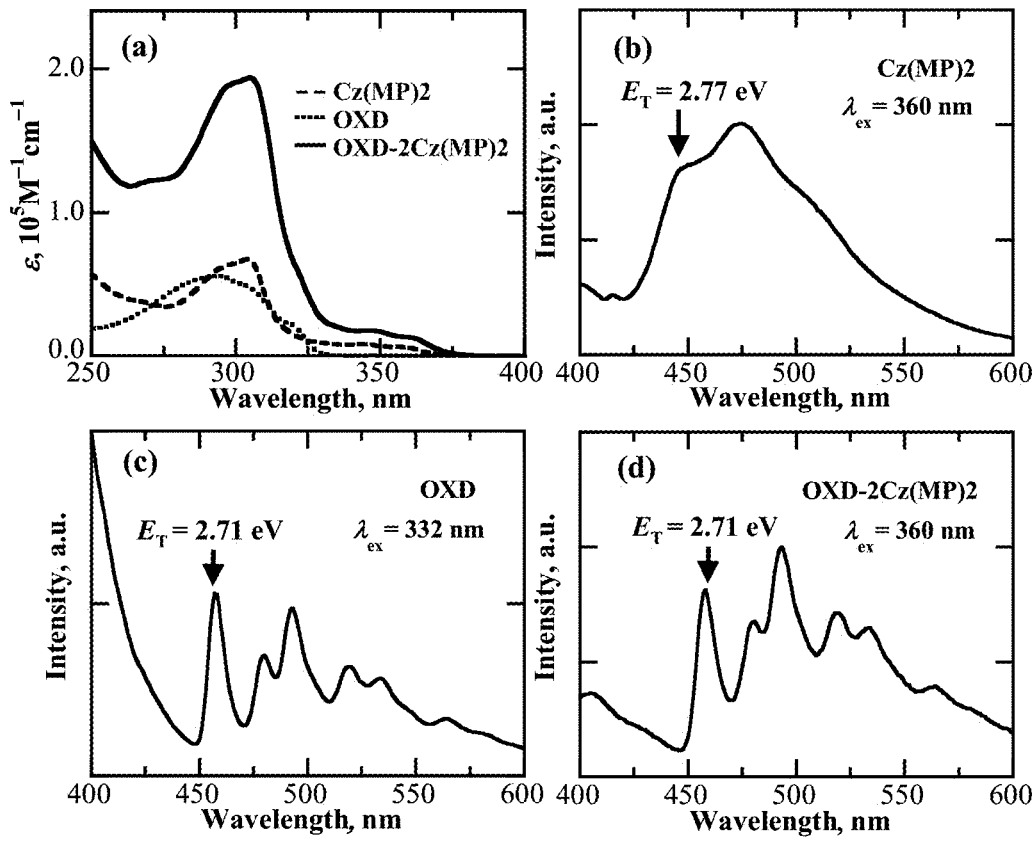

The absorption spectra of Cz(MP)2, OXD, and OXD-2Cz(MP)2 at $10^{-7}$ to $10^{-6}$ M in chloroform are presented in FIG. 7a, serving to identify selective photoexcitation wavelengths for the determination of their lowest triplet energies, $E_T$, to within ±0.02 eV through phosphorescence measurements. Phosphorescence spectra were obtained for Cz(MP)2, OXD, and OXD-2Cz(MP)2 at $10^{-4}$ M in ethyl acetate at −196° C. (or 77 K). As illustrated in FIG. 7b, Cz(MP)2 shows a 0,0-phosphorescence band corresponding to an $E_T$ at 2.77 eV upon excitation at 360 nm. The OXD moiety shows only very weak phosphorescence due largely to inefficient intersystem crossing. Thus, butyl iodide was added at 10 wt % to the OXD and OXD-2Cz(MP)2 solutions to enhance phosphorescence, particularly the 0,0-vibronic transition, 6 and to help confirm the identity of the emitting state. With photoexcitation at 332 nm, the relatively sharp highest-energy 0,0-vibronic band shown in FIG. 7c establishes an $E_T$ of 2.71 eV for OXD. When the hybrid compound OXD-2Cz(MP)2 is excited at 360 nm (FIG. 7d), its phosphorescence spectrum is identical to that of OXD (FIG. 7c) even though OXD is not excitable at 360 nm. These results indicate highly efficient triplet energy transfer from Cz(MP)2 ($E_T$=2.77 eV) to OXD ($E_T$=2.71 eV) in OXD-2Cz(MP)2 and further suggest that the two moieties retain their energy levels as independent entities and that the effective $E_T$ of the hybrid equals that of the lower-$E_T$ moiety due to efficient intramolecular triplet energy transfer. Phosphorescence spectra were also collected for TRZ and TRZ-3Cz(MP)2 to arrive at $E_T$=3.03 and 2.75 eV, respectively, an observation also consistent with highly efficient triplet energy transfer from TRZ to the lower energy Cz(MP)2 moiety. Furthermore, the $E_T$ value of a non-conjugated bipolar hybrid compound is determined by the lower value of the two independent moieties. The $E_T$ value of a conjugated bipolar compound, however, is consistently less than those of the two independent moieties because of the finite π-conjugation between them.

Assessment of another merit of non-conjugated bipolar compounds can be achieved by comparison to their conjugated counterparts. In a conjugated bipolar compound, the $E_T$ value is consistently less than $E_G$, the LUMO-HOMO energy gap, by the sum of singlet-triplet splitting, $\Delta_{ST}$, and exciton binding energy, $E_B$. For example, CzOXD has its HOMO/LUMO levels at −5.6/−2.4 eV based on the reported half-wave potentials with an $E_T$ at 2.5 eV, 29 which is 0.7 eV less than $E_G$ (see FIG. 8a).

Figure 8:
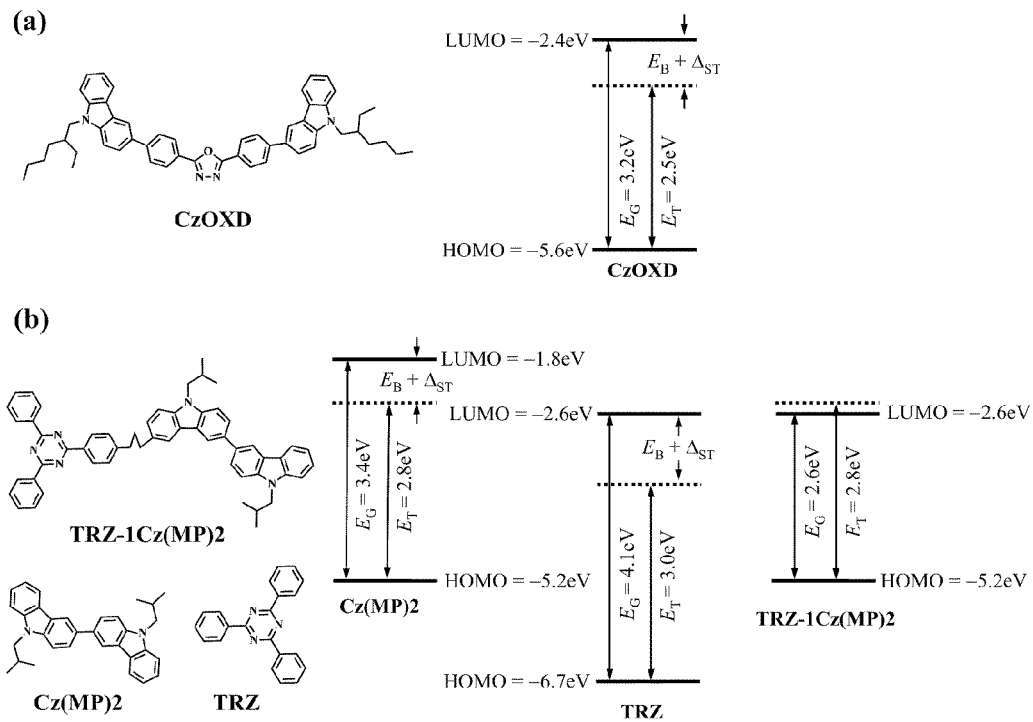
FIG. 8. (a) Molecular structure and energy diagram of a conjugated bipolar compound CzOXD, and (b) Molecular structure and energy diagram of a non-conjugated bipolar compound TRZ-1Cz(MP)2 accompanied by those of Cz(MP)2 and TRZ.

On the other hand, the $E_T$ value of a non-conjugated bipolar compound, such as TRZ-1Cz(MP)2, is not limited by its $E_G$. The oxidation potentials of TRZ and OXD and the reduction potential of Cz(MP)2 are beyond our CV measurement range. Their optical bandgaps were estimated at the onset of their absorption spectra in dilute solutions to yield HOMO levels at −6.7 and −6.2 eV for TRZ and OXD, respectively, and LUMO level at −1.8 eV for Cz(MP)2. As shown in FIG. 8b, the $E_T$s of independent electron- and hole-transport moieties are less than their respective $E_G$s as in a typical conjugated system. The Cz(MP)2 moiety is characterized by an $E_T$ and HOMO/LUMO levels at 2.8 eV, and −5.2/−1.8 eV, respectively, while the TRZ moiety carries an $E_T$ and HOMO/LUMO levels at 3.0 eV, and −6.7/−2.6 eV, respectively (see FIG. 8b). The hybrid TRZ-1Cz(MP)2 has an $E_T$ at 2.8 eV, as verified by low temperature phosphorescence spectroscopy, and HOMO/LUMO levels at −5.2/−2.6 eV by cyclic voltammetry. In contrast to CzOXD, TRZ-1Cz(MP)2 has an $E_T$ greater than its $E_G$ and its HOMO/LUMO levels corresponding to the hole- and electron-transport moieties without modification in the absence of inter-moiety conjugation. The caveat here is that the $E_T$s of both the electron- and hole-transport moieties must be greater than the hybrid's $E_G$ to arrive at a non-conjugated bipolar compound with an $E_T$ greater than its $E_G$, as is also applicable to TRZ-3Cz(MP)2 and OXD-2Cz(MP)2.

Bipolar hybrid TRZ-3Cz(MP)2 and TRZ-1Cz(MP)2 and hole-transporting Cz(MP)2 were employed as hosts for the fabrication of bilayer phosphorescent OLEDs in the device architecture, ITO/MoO$_3$ (10 nm)/emitting layer (40~50 nm)/1,3,5-tris(N-phenylbenzimidazol-2-yl)benzene (TPBI)(30 nm)/CsF(1 nm)/Al 100 nm). Prepared by spin casting, the emitting layer consisted of a host doped with green-emitting tris(2-(p-methylphenyl)pyridine)iridium, Ir(mppy)$_3$, at a 10:1 mass ratio. While MoO$_3$ and CsF were applied as the hole- and electron-injection layers, respectively, TPBI was applied as the electron-transporting and hole-blocking layer. A typical electroluminescence spectrum is shown as the inset in FIG. 9a, consistent with the triplet emission of Ir(mppy)3, suggesting effective confinement of triplet excitons on the emitter. This is expected of the higher $E_T$s of all three hosts than that of 1r(mppy)$_3$, 2.8 eV for Cz(MP)2 over 2.4 eV for Ir(mppy)$_3$. Furthermore, Ir(mppy)$_3$ has a HOMO level at −5.0 eV, 0.2 eV higher than those of the hosts, thus serving as a hole trap to preclude exciplex formation between the TRZ and Cz(MP)2 moieties.

Figure 9:
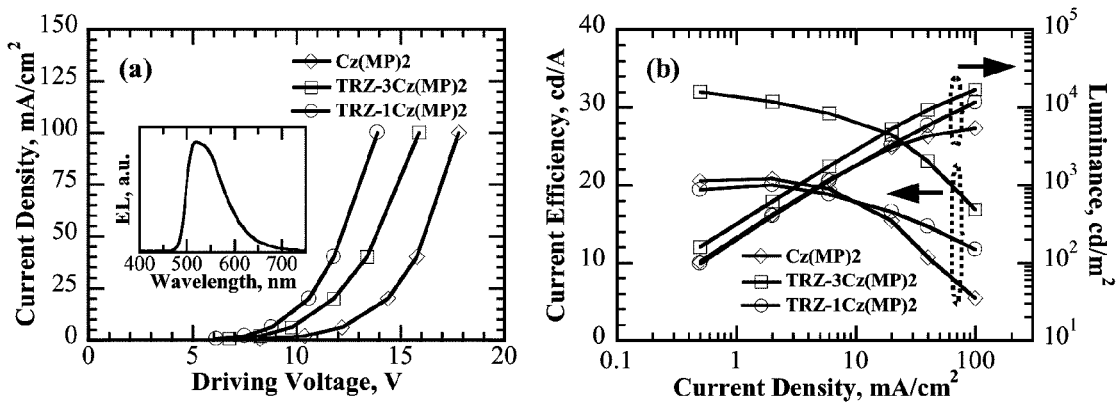
FIG. 9. (a) Current density as a function of driving voltage for phosphorescent OLEDs with emitting layers comprising Cz(MP)2, TRZ-3Cz(MP)2, and TRZ-1Cz(MP)2 doped with Ir(mppy)$_3$ at a 10:1 mass ratio. Inset: electroluminescence (EL) spectrum with TRZ-3Cz(MP)2 as the host. (b) Luminance and current efficiency as functions of current density for the same phosphorescent OLEDs as described in (a).

It is also shown in FIG. 9a that driving voltage decreases with an increasing TRZ content in the hybrid hosts, suggesting improved electron injection from the adjacent TPBI into the emitting layer. Current efficiency and luminance as functions of current density are shown in FIG. 9b. Compared to Cz(MP)2, the higher efficiency with TRZ-3Cz(MP)2 as the host is attributable to the more balanced electron and hole fluxes through the emitting layer, which leads to the more efficient electron-hole recombination. Furthermore, the presence of electron-transporting TRZ in TRZ-3Cz(MP)2 generates a broader charge recombination zone to alleviate efficiency roll-off at high current densities. As shown in FIG. 9b, at the current density of 0.5 mA/cm$^2$, the device with Cz(MP)2 as the host has a luminance of 105 cd/m$^2$, corresponding to current efficiency of 21 cd/A and external quantum efficiency of 5.9%, which diminish to 5.4 cd/A and 1.5% at 100 mA/cm$^2$, respectively, representing a 74% loss in efficiencies. In contrast, at the current density of 0.5 mA/cm$^2$, the device with TRZ-3Cz(MP)2 as the host has a luminance of 160 cd/m$^2$, corresponding to current efficiency of 32 cd/A and external quantum efficiency of 9.2%, which roll off to 16.8 cd/A and 4.9% at 100 mA/cm$^2$, respectively, representing a 47% loss in efficiencies. The efficiencies achieved with TRZ-3Cz(MP)2 as the host are among the best known solution-processed phosphorescent OLEDs using bipolar hosts. Implemented in more sophisticated device architectures, optimum non-conjugated bipolar hybrids can be expected to yield much higher efficiencies than the bilayer device architecture as presently reported. With a further increase in the TRZ content, however, TRZ-1Cz(MP)2 resulted in current efficiencies comparable to those with Cz(MP)2 as the host, presumably because of exciton quenching by MoO$_3$ as the recombination zone is shifted toward the anode at an increased electron transport. The results obtained to date have demonstrated the potential of non-conjugated bipolar hybrid hosts with flexible linkages for substantially improving PhOLED device performance through optimization of change injection into and transport through the emitting layer.

Potentially useful as the host materials for the fabrication of efficient and stable, single-layer phosphorescent OLEDs for information display and solid-state lighting, a new class of non-conjugated bipolar compounds have been synthesized and characterized for their thermal, morphological, electrochemical, fluorescence, and phosphorescence properties. Comprising hole- and electron-transport moieties chemically bonded by an aliphatic spacer, the potential of these materials has been demonstrated for solution processing and for the formation of thin films with elevated glass transition temperatures with superior stability against phase separation and thermally activated crystallization. Because of the absence of π-conjugation between the two charge-carrier moieties, the LUMO/HOMO levels and the triplet energies of the two moieties as independent entities are retained in the resultant non-conjugated bipolar compounds. Furthermore, the flexibility in molecular design is enhanced by the fact that the triplet energy of a non-conjugated bipolar compound is not constrained by its electrochemical energy gap. Exciplex formation may occur in neat films between the hole- and electron-transport moieties, but its adverse effects on spectral purity and device efficiency can be prevented by having triplet emitters serve as charge traps. All these material traits are conducive to the optimization of properties for intended device applications. The current efficiencies of PhOLEDs consisting of 1r(mppy)$_3$ doped in Cz(MP)2, TRZ-3Cz(MP)2, and TRZ-1Cz(MP)2 at an increasing TRZ content reach the maximum at 32 cd/A with TRZ-3Cz(MP)2, which is among the best of solution processed devices using bipolar hosts. The driving voltage, however, decreases monotonically with an increasing TRZ content, suggesting improved electron injection from the adjacent TPBI layer into the emitting layer.

In one embodiment, the present invention is an organic light emitting device comprising a host material and a triplet emitter, wherein the host material comprises any of the compounds disclosed herein or a combination thereof.

What is claimed is:
1. A compound having the following structure:
2,4,6-tris(4-(3-(6-(9-(2-methylpropyl)carbazol-3-yl)-9-(2-methylpropyl)carbazol-3-yl)propyl)phenyl)-1,3,5-triazine (TRZ-3Cz(MP)2);
2-(4-(3-(6-(9-(2-methylpropyl)carbazol-3-yl)-9-(2-methylpropyl)carbazol-3-yl)propyl)phenyl)-4,6-diphenyl-1,3,5-triazine (TRZ-1Cz(MP)2);
2,4,6-tris(4-(3-(3,6-bis(9-(2-methylpropyl)carbazol-3-yl)carbazol-9-yl)propyl)phenyl)-1,3,5-triazine (TRZ-3Cz(N)Cz(MP)2);
2,4,6-tris(4-(3-(6-(7-(9-(2-methylpropyl)carbazol-3-yl)-9,9-bis(2-methylpropyl)fluoren-2-yl)-9-(2-methylpropyl)carbazol-3-yl)propyl)phenyl)-1,3,5-triazine (TRZ-3Cz(MP)2F(MP));
Tris(4-(3-(6-(9-(2-methylpropyl) carbazol-3-yl)-9-(2-methylpropyl) carbazol-3-yl)propyl)phenyl)amine (TPA-3Cz(MP)2); or
1,3,5-tris(4-(3-(6-(9-(2-methylpropyl)carbazol-3-yl)-9-(2-methylpropyl)carbazol-3-yl)propyl)phenyl)benzene (TPB-3Cz(MP)2).

2. A compound having the following structure:
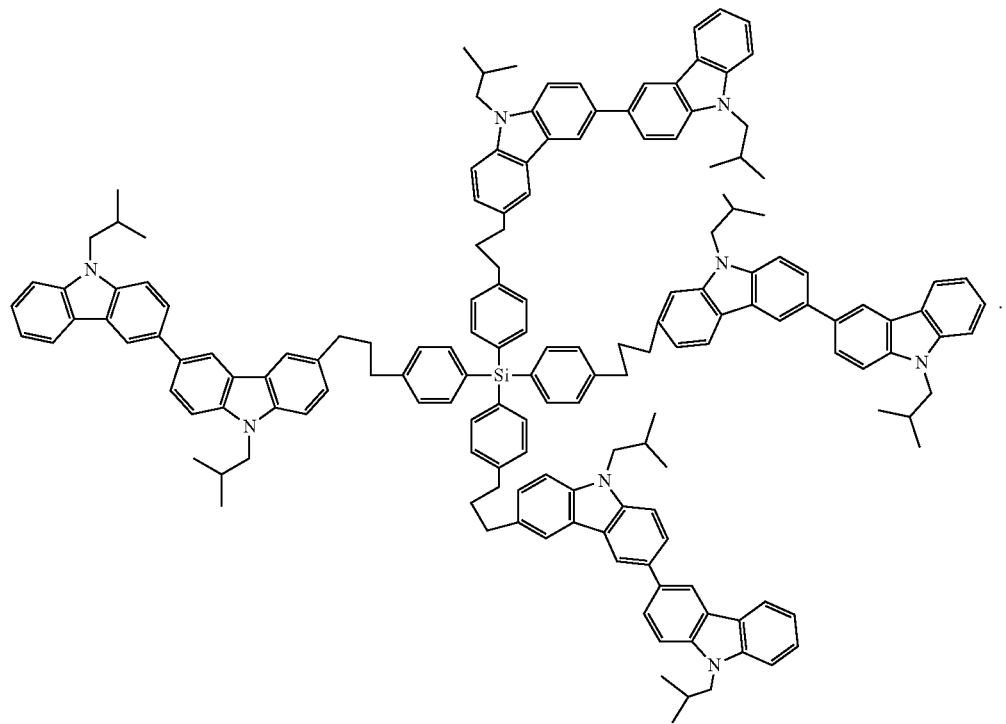 [SMILES: CC(C)Cn1c2ccccc2c2cc(-c3ccc4c(c3)c3cc(CCCc5ccc([Si](c6ccc(CCCc7ccc8c(c7)c7cc(-c9ccc%10c(c9)c9ccccc9n%10CC(C)C)ccc7n8CC(C)C)cc6)(c6ccc(CCCc7ccc8c(c7)c7cc(-c9ccc%10c(c9)c9ccccc9n%10CC(C)C)ccc7n8CC(C)C)cc6)c6ccc(CCCc7ccc8c9cc(-c%10ccc%11c(c%10)c%10ccccc%10n%11CC(C)C)ccc9n(CC(C)C)c8c7)cc6)cc5)ccc3n4CC(C)C)ccc21]
* * * * *